United States Patent
Studer et al.

(10) Patent No.: US 8,507,726 B2
(45) Date of Patent: *Aug. 13, 2013

(54) PHOTOINITIATOR MIXTURES

(75) Inventors: Katia Studer, Rixheim (FR); Sébastien Villeneuve, Huningue (FR); Akira Matsumoto, Amagasaki (JP); Hisatoshi Kura, Takarazuka (JP); Jan Sültemeyer, Village Neuf (FR)

(73) Assignee: BASF SE, Ludwigshafen (DE)

( * ) Notice: Subject to any disclaimer, the term of this patent is extended or adjusted under 35 U.S.C. 154(b) by 86 days.

This patent is subject to a terminal disclaimer.

(21) Appl. No.: 13/127,068

(22) PCT Filed: Oct. 23, 2009

(86) PCT No.: PCT/EP2009/063963
§ 371 (c)(1),
(2), (4) Date: May 24, 2011

(87) PCT Pub. No.: WO2010/060702
PCT Pub. Date: Jun. 3, 2010

(65) Prior Publication Data
US 2011/0218266 A1    Sep. 8, 2011

(30) Foreign Application Priority Data
Nov. 3, 2008 (EP) .................... 08168145

(51) Int. Cl.
*C07C 259/00* (2006.01)

(52) U.S. Cl.
USPC .............. 564/254; 564/253; 522/33; 522/39; 522/65; 522/9; 522/8; 522/11; 522/49; 522/57; 522/71; 522/74; 522/81; 522/113; 522/114; 522/100; 522/101; 522/150; 522/153; 522/154; 522/178; 522/181; 522/182; 522/183; 359/891

(58) Field of Classification Search
USPC .............. 522/33, 39, 65, 9, 8, 11, 49, 57, 71, 522/74, 81, 113, 114, 100, 101, 150, 153, 522/154, 178, 181, 182, 183
See application file for complete search history.

(56) References Cited

U.S. PATENT DOCUMENTS

| | | |
|---|---|---|
| 2009/0041922 A1 | 2/2009 | Kuhnle et al. |
| 2009/0136433 A1 | 5/2009 | Subkowski et al. |
| 2010/0086881 A1 | 4/2010 | Matsumoto |
| 2010/0136467 A1 | 6/2010 | Matsumoto |
| 2010/0136491 A1 | 6/2010 | Matsumoto |
| 2010/0166627 A1 | 7/2010 | Baus et al. |
| 2010/0170142 A1 | 7/2010 | Posselt et al. |
| 2010/0240774 A1 | 9/2010 | Subkowski |
| 2011/0134554 A1 | 6/2011 | Matsumoto |
| 2011/0159050 A1 | 6/2011 | Hafner et al. |
| 2011/0170209 A1* | 7/2011 | Matsumoto et al. .......... 359/891 |

FOREIGN PATENT DOCUMENTS

| | | |
|---|---|---|
| WO | 2007/071497 A | 6/2007 |
| WO | 2009/147031 A2 | 12/2009 |

OTHER PUBLICATIONS

Copending U.S. Appl. No. 11/887,282, filed Aug. 17, 2007.
Copending U.S. Appl. No. 13/127,068, filed May 2, 2011.

* cited by examiner

*Primary Examiner* — Sanza McClendon
(74) *Attorney, Agent, or Firm* — Shruti Costales

(57) ABSTRACT

Photoinitiators mixture comprising (i) at least one compound selected from the group consisting of alpha-hydroxy ketones, monoacylphosphine oxides, bisacylphosphine oxides, ketosulfones, benzil ketals, benzoin ether, phenylglyoxylates, borates and titanocenes; and (ii) at least one compound of the formula (I) or (I') $R_1$, $R'_1$, $R_2$ and $R_2'R'_9$ independently of each other for example are hydrogen or $C_1$-$C_{12}$alkyl $R_7$, $R_8$, $R_9$, $R'_8$ and $R'_9$ independently of each other for example are hydrogen, $C_1$-$C_{12}$alkyl which optionally is substituted or phenyl which optionally is substituted, exhibit excellent photoinitiating properties.

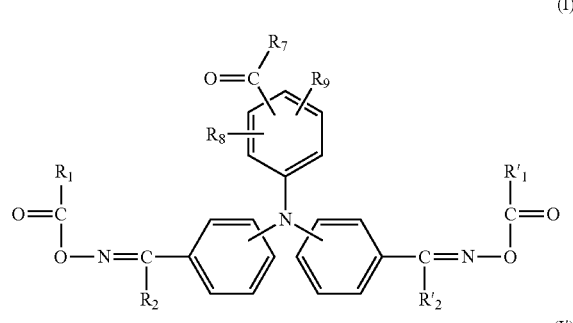

(I)

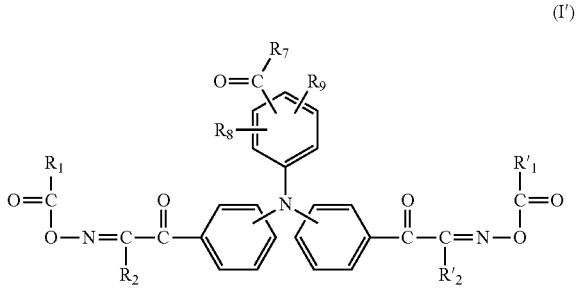

(I')

16 Claims, No Drawings

PHOTOINITIATOR MIXTURES

The invention pertains to photoinitiator mixtures of alpha-hydroxyketone, mono- or bisacylphosphine oxides, benzophenones, thioxanthones, ketosulfones, benzil ketals, phenylglyoxylates, borates or titanocenes photoinitiators and specific oxime ester compounds and their use as photoinitiators in photopolymerizable compositions.

Alpha-hydroxyketones are known to be photoinitiators, as for example disclosed in U.S. Pat. Nos. 4,347,111, 4,321,118, WO 04/092287, U.S. Pat. Nos. 4,672,079, 4,987,159 or WO 02/85832. Mono- or bisacylphosphine oxides also are known from e.g. U.S. Pat. No. 4,324,744, EP 40721 (=Derwent 91349 D/50), U.S. Pat. No. 4,737,593, GB 2259704 or U.S. Pat. No. 6,020,528. Ketosulfone photoinitiators are for example known from WO 00/031030. In WO 06/120212, U.S. Pat. Nos. 6,048,660, 4,475,999 and 4,038,164 phenylglyoxylates are described as photoinitiators. Borates as photoinitiators are for example shown in U.S. Pat. No. 51,766,984 or GB 2307474 and titanocenes are for example disclosed in U.S. Pat. Nos. 5,008,302 and 5,340,701.

Further, a wide variety of oxime ester compounds is used as photoinitiator, in particular in electronic applications as for example in color filter resists, also the color filter black matrix, etc. as disclosed for example in WO 02/100903.

In photopolymerization technology there still exists a need for highly reactive, easy to prepare and easy to handle photoinitiators. For example in color filter resist applications, highly pigmented resists are required for the high color quality property. With the increase of the pigment content, the curing of color resists becomes more difficult. The same applies for the curing of inks, for example offset inks, which also are loaded with pigments. Further, the curing of adhesives affords appropriate photoinitiators, Hence, a photoinitiator having a higher sensitivity and excellent resolution properties than current initiation systems is required. In addition, also such new photoinitiators must meet the high requirements of the industry regarding properties like, for example, high solubility, thermal stability and storage stability.

Surprisingly, it now has been found, that a mixture of above mentioned photoinitiators and selected oxime ester compounds perfoms unexpectedly better than the known photoinitiator compounds alone.

Subject of the invention therefore is a photoinitiator mixture comprising
(i) at least one compound selected from the group consisting of alpha-hydroxy ketones, monoacylphosphine oxides, bisacylphosphine oxides, ketosulfones, benzil ketals, benzoin ether, phenylglyoxylates, borates and titanocenes; and
(ii) at least one compound of the formula (I) and (I')

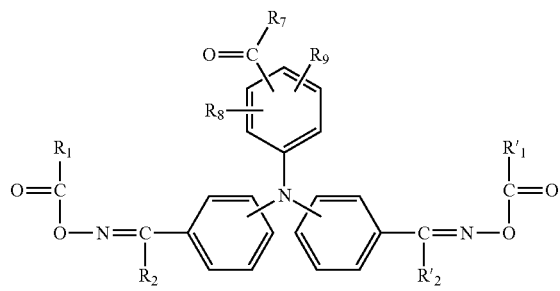
(I)

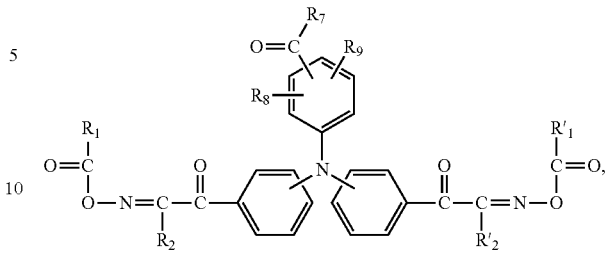
(I')

wherein
$R_1$ and $R'_1$ independently of one another are hydrogen, $C_3$-$C_8$cycloalkyl or $C_1$-$C_{12}$alkyl which is unsubstituted or substituted by one or more halogen, phenyl and/or CN; or
$R_1$ and $R'_1$ are $C_2$-$C_5$alkenyl; or
$R_1$ and $R'_1$ are phenyl which is unsubstituted or substituted by one or more $C_1$-$C_6$alkyl, halogen, CN, $OR_3$, $SR_4$ and/or $NR_5R_6$; or
$R_1$ and $R'_1$ are $C_1$-$C_8$alkoxy, benzyloxy; or phenoxy which is unsubstituted or substituted by one or more $C_1$-$C_6$alkyl and/or halogen;
$R_2$ and $R_2'$ independently of one another are hydrogen; unsubstituted $C_1$-$C_{20}$alkyl or $C_1$-$C_{20}$alkyl substituted by one or more halogen, $OR_3$, $SR_4$, $C_1$-$C_{20}$heteroaryl, $C_8$-$C_{20}$-phenoxycarbonyl, $C_1$-$C_{20}$heteroaryloxycarbonyl, $NR_5R_6$, $COOR_3$, $CONR_5R_6$,

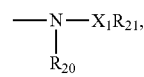

phenyl and/or by phenyl which is substituted by $OR_3$, $SR_4$ and/or $NR_5R_6$, wherein the unsubstituted or substituted $C_1$-$C_{20}$alkyl optionally contains one or more C—C multiple bonds; or
$R_2$ and $R_2'$ are $NR_5R_6$,

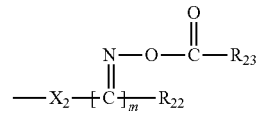

or $C_3$-$C_{20}$cycloalkyl;
or are $C_2$-$C_{20}$alkyl which is interrupted by one or more O and which optionally is substituted by one or more halogen, $OR_3$, phenyl and/or phenyl substituted by $OR_3$, $SR_4$ and/or $NR_5R_6$; or
$R_2$ and $R_2'$ are phenyl which is unsubstituted or substituted by one or more $C_1$-$C_6$alkyl, phenyl, halogen, $OR_3$, $SR_4$ and/or $NR_5R_6$; or
$R_2$ and $R_2'$ are $C_2$-$C_{20}$alkanoyl or benzoyl which is unsubstituted or substituted by one or more $C_1$-$C_6$alkyl, phenyl, $OR_3$, $SR_4$ and/or $NR_5R_6$; or
$R_2$ and $R_2'$ are $C_2$-$C_{12}$alkoxycarbonyl which is optionally interrupted by one or more O and/or optionally substituted by one or more hydroxyl groups; or
$R_2$ and $R_2'$ are phenoxycarbonyl which is unsubstituted or substituted by $C_1$-$C_6$alkyl, halogen, phenyl, $OR_3$, $SR_4$ and/or $NR_5R_6$; or $R_2$ and $R_2'$ are CN, $CONR_5R_6$, $NO_2$, $S(O)_m$—$C_1$-$C_6$alkyl; $S(O)_m$-phenyl which optionally is substituted by $C_1$-$C_{12}$alkyl or $SO_2$—$C_1$-$C_6$alkyl; or are $SO_2O$-phenyl which optionally is substituted by $C_1$-$C_{12}$alkyl;

or are diphenyl phosphinoyl or di-($C_1$-$C_4$alkoxy)-phosphinoyl; or $R_2$ and $R_2'$ are

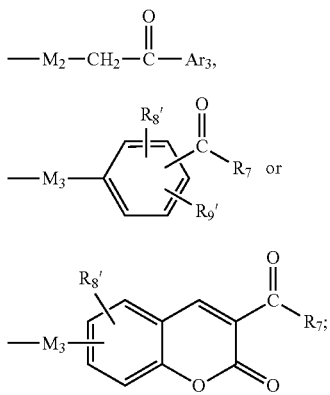

m is 1 or 2;

$Ar_3$ is phenyl, naphthyl or coumarinyl, each of which is substituted once or more times by halogen, $C_1$-$C_{12}$alkyl, $C_3$-$C_8$cycloalkyl, benzyl and/or phenoxycarbonyl; or each of which is substituted by phenyl or by phenyl which is substituted by one or more $OR_3$, $SR_4$ and/or $NR_5R_6$; or each of which is substituted by $C_2$-$C_{12}$alkoxycarbonyl optionally interrupted by one or more O and/or optionally substituted by one or more hydroxyl groups; or each of which is substituted by $OR_3$, $SR_4$, $SOR_4$, $SO_2R_4$ and/or $NR_5R_6$;

$M_2$ is a direct bond, cyclohexylene or $C_1$-$C_{10}$alkylene or $C_1$-$C_{10}$alkylene-X—, which $C_1$-$C_{10}$alkylene or $C_1$-$C_{10}$alkylene-X— is optionally interrupted by one or more O and/or optionally substituted by one or more halogen, $OR_3$, phenyl or phenyl substituted by $OR_3$, $SR_4$ and/or $NR_5R_6$; or $M_2$ is phenylene, naphthylene or phenylene-X—, each of which is unsubstituted or substituted by one or more $C_1$-$C_6$alkyl, phenyl, halogen, $OR_3$, $SR_4$ or $NR_5R_6$; or $M_2$ is $C_1$-$C_{10}$alkylene-C(O)—X—, $C_1$-$C_{10}$alkylene-X—C(O)—, phenylene-C(O)—X— or $C_1$-$C_{10}$alkylene-phenylene-X—;

$M_3$ is a direct bond, cyclohexylene, $C_1$-$C_{10}$alkylene or $C_1$-$C_{10}$alkylene-X—, which $C_1$-$C_{10}$alkylene or $C_1$-$C_{10}$alkylene-X— is optionally interrupted by one or more O and/or optionally substituted by one or more halogen, $OR_3$, phenyl or phenyl substituted by $OR_3$, $SR_4$ and/or $NR_5R_6$; or $M_3$ is phenylene, naphthylene or phenylene-X—, each of which is unsubstituted or substituted by one or more $C_1$-$C_6$alkyl, phenyl, halogen, $OR_3$, $SR_4$ and/or $NR_5R_6$; or $M_3$ is $C_1$-$C_{10}$alkylene-C(O)—X—, $C_1$-$C_{10}$alkylene-X—C(O)—, phenylene-C(O)—X—, $C_1$-$C_{10}$alkylene-phenylene-X— or phenylene-(CO)-phenylene;

X is O, S or $NR_5$;

$X_1$ is O, S, SO or $SO_2$;

$X_2$ is a direct bond, $C_1$-$C_{20}$alkylene which optionally is interrupted by O, CO or $NR_5$, and which uninterrupted or interrupted $C_1$-$C_{20}$alkylene is unsubstituted or substituted by one or more halogen, $OR_3$, $COOR_3$, $NR_5R_6$, $C_1$-$C_{20}$heteroaryl, $C_1$-$C_{20}$heteroaryl-(CO)O, $C_1$-$C_{20}$heteroaryl-S, $CONR_5R_6$,

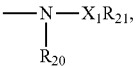

phenyl or ray phenyl substituted by halogen, $C_1$-$C_{20}$alkyl, $C_1$-$C_4$haloalkyl, $SR_4$, $OR_3$, or $NR_5R_6$, and which unsubstituted or substituted, interrupted or non-interrupted $C_1$-$C_{20}$alkylene optionally contains one or more C—C multiple bonds;

$R_3$ is hydrogen, $C_1$-$C_{20}$alkyl or phenyl-$C_1$-$C_3$alkyl; or $R_3$ is $C_1$-$C_{20}$alkyl which is substituted by OH, SH, —CN, $C_3$-$C_6$alkenoxy, $OCH_2CH_2CN$, $OCH_2CH_2(CO)O(C_1$-$C_4$alkyl), O(CO)—($C_1$-$C_4$alkyl), O(CO)-phenyl, (CO)OH and/or (CO)O($C_1$-$C_4$alkyl); or $R_3$ is $C_2$-$C_{20}$alkyl which is interrupted by one or more O; or $R_3$ is $(CH_2CH_2O)_{n+1}H$, $(CH_2CH_2O)_n(CO)$—($C_1$-$C_8$alkyl), $C_1$-$C_8$alkanoyl, $C_2$-$C_{12}$alkenyl, $C_3$-$C_6$alkenoyl or $C_3$-$C_{20}$cycloalkyl which optionally is interrupted by O, S, CO, $NR_5$; or $R_3$ is benzoyl which is unsubstituted or substituted by one or more $C_1$-$C_6$alkyl, halogen, OH and/or $C_1$-$C_4$alkoxy; or $R_3$ is phenyl, naphthyl or $C_1$-$C_{20}$heteroaryl, each of which is unsubstituted or substituted by halogen, OH, $C_1$-$C_{12}$alkyl, $C_1$-$C_{12}$alkoxy, CN, $NO_2$, phenyl-$C_1$-$C_3$alkyloxy, phenoxy, $C_1$-$C_{12}$alkylsulfanyl, phenylsulfanyl, $N(C_1$-$C_{12}$alkyl$)_2$, diphenylamino and/or

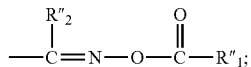

n is 1-20;

$R_4$ is hydrogen, $C_1$-$C_{20}$alkyl, $C_2$-$C_{12}$alkenyl, $C_3$-$C_{20}$cycloalkyl, phenyl-$C_1$-$C_3$alkyl, wherein the $C_1$-$C_{20}$alkyl, $C_2$-$C_{12}$alkenyl, $C_3$-$C_{20}$cycloalkyl, phenyl-$C_1$-$C_3$alkyl optionally is interrupted by O, S, CO, $NR_5$; or $R_4$ is $C_1$-$C_8$alkyl which is substituted by OH, SH, CN, $C_3$-$C_6$alkenoxy, $OCH_2CH_2CN$, $OCH_2CH_2(CO)O(C_1$-$C_4$alkyl), O(CO)—($C_1$-$C_4$alkyl), O(CO)-phenyl, (CO)OH or (CO)O($C_1$-$C_4$alkyl); or $R_4$ is $(CH_2CH_2O)_{n+1}H$, $(CH_2CH_2O)_n(CO)$—($C_1$-$C_8$alkyl), $C_1$-$C_8$alkanoyl, $C_2$-$C_{12}$alkenyl, $C_3$-$C_6$alkenoyl; or $R_4$ is benzoyl which is unsubstituted or substituted by one or more $C_1$-$C_6$alkyl, halogen, —OH, $C_1$-$C_4$alkoxy or $C_1$-$C_4$alkylsulfanyl; or $R_4$ is phenyl, naphthyl or $C_1$-$C_{20}$heteroaryl, each of which is unsubstituted or substituted by halogen, $C_1$-$C_{12}$alkyl, $C_1$-$C_{12}$alkoxy, CN, $NO_2$, phenyl-$C_1$-$C_3$alkyloxy, phenoxy, $C_1$-$C_{12}$alkylsulfanyl, phenylsulfanyl, $N(C_1$-$C_{12}$alkyl$)_2$, diphenylamino, (CO)O($C_1$-$C_8$alkyl), (CO)—$C_1$-$C_8$alkyl, (CO)N($C_1$-$C_8$alkyl$)_2$ or

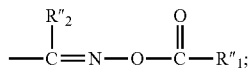

$R_5$ and $R_6$ independently of each other are hydrogen, $C_1$-$C_{20}$alkyl, $C_2$-$C_4$hydroxyalkyl, $C_2$-$C_{10}$alkoxyalkyl, $C_2$-$C_5$alkenyl, $C_3$-$C_{20}$cycloalkyl, phenyl-$C_1$-$C_3$alkyl, $C_1$-$C_8$alkanoyl, $C_3$-$C_{12}$-alkenoyl, benzoyl; or $R_5$ and $R_6$ are phenyl, naphthyl or $C_1$-$C_{20}$heteroaryl, each of which is unsubstituted or substituted by $C_1$-$C_{12}$alkyl, benzoyl or $C_1$-$C_{12}$alkoxy; or $R_5$ and $R_6$ together with the N-atom to which they are attached form a 5- or 6-membered saturated or unsaturated ring which optionally is interrupted by O, S or $NR_3$, and which ring is unsubstituted or substituted by one or more $C_1$-$C_{20}$alkyl, $C_1$-$C_{20}$alkoxy, =O, $SR_4$, $OR_3$ or $NR_{17}R_{18}$, $(CO)R_{19}$, $NO_2$, halogen, $C_1$-$C_4$haloalkyl, CN, phenyl,

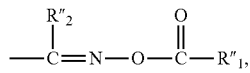

or by $C_3$-$C_{20}$cycloalkyl which optionally is interrupted by O, S, CO or $NR_3$; or $R_5$ and $R_6$ together with the N-atom to which they are attached form a heteroaromatic ring system, which heteroaromatic ring system is unsubstituted or substituted by one or more $C_1$-$C_{20}$alkyl, $C_1$-$C_4$haloalkyl, $C_1$-$C_{20}$alkoxy, =O, $SR_4$, $OR_3$, $NR_{17}R_{18}$, $(CO)R_{19}$,

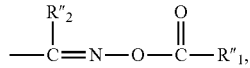

halogen, $NO_2$, CN, phenyl or by $C_3$-$C_{20}$cycloalkyl which optionally is interrupted by O, S, CO or $NR_3$;

$R''_1$ has one of the meanings as given for $R_1$;

$R''_2$ has one of the meanings as given for $R_2$;

$R_7$ is hydrogen, $C_1$-$C_{20}$alkyl; $C_1$-$C_8$alkyl which is substituted by halogen, phenyl, OH, SH, CN, $C_3$-$C_6$alkenoxy, $OCH_2CH_2CN$, $OCH_2CH_2(CO)O(C_1$-$C_4$alkyl), $O(CO)$—$(C_1$-$C_4$alkyl), $O(CO)$-phenyl, $(CO)OH$ or $(CO)O(C_1$-$C_4$alkyl); or $R_7$ is $C_2$-$C_{12}$alkyl which is interrupted by one or more O; or $R_7$ is $(CH_2CH_2O)_{n+1}H$, $(CH_2CH_2O)_n(CO)$—$(C_1$-$C_8$alkyl), $C_2$-$C_{12}$alkenyl or $C_3$-$C_8$cycloalkyl; or $R_7$ is phenyl, biphenylyl, naphthyl or $C_1$-$C_{20}$heteroaryl, each of which optionally is substituted by one or more $C_1$-$C_{20}$alkyl, halogen, $C_1$-$C_{12}$haloalkyl, CN, $NO_2$, $OR_3$, $SR_4$, $SOR_4$, $SO_2R_4$ or $NR_5R_6$, wherein the substituents $OR_3$, $SR_4$ or $NR_5R_6$ optionally form 5- or 6-membered rings via the radicals $R_3$, $R_4$, $R_5$ and/or $R_6$ with one of the carbon atoms of the phenyl, biphenylyl, naphthyl or $C_1$-$C_{20}$heteroaryl ring;

$R_8$ and $R_9$ and $R'_8$ and $R'_9$ independently of each other are hydrogen, $C_1$-$C_{12}$alkyl which optionally is substituted by one or more halogen, phenyl, CN, OH, SH, $C_1$-$C_{12}$alkoxy, $(CO)OH$ or $(CO)O(C_1$-$C_4$alkyl); or $R_8$ and $R_9$ and $R'_8$ and $R'_9$ are phenyl which optionally is substituted by one or more $C_1$-$C_6$alkyl, halogen, CN, $OR_3$, $SR_4$ or $NR_5R_6$; or $R_8$ and $R_9$ and $R'_8$ and $R'_9$ are halogen, CN, $OR_3$, $SR_4$, $SOR_4$, $SO_2R_4$ or $NR_5R_6$, wherein the substituents $OR_3$, $SR_4$ or $NR_5R_6$ optionally form 5- or 6-membered rings via the radicals $R_3$, $R_4$, $R_5$ and/or $R_6$ with one of the carbon atoms of the phenyl or with the substituent $R_7$ or one of the carbon atoms of the naphthylene or phenylene group of $M_3$; or $R_8$ and $R_9$ and $R'_8$ and $R'_9$ together are

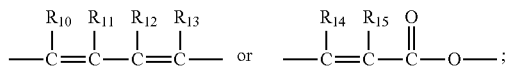

$R_{10}$, $R_{11}$, $R_{12}$ and $R_{13}$ independently of one another are hydrogen, $C_1$-$C_{12}$alkyl which optionally is substituted by one or more halogen, phenyl, CN, OH, SH, $C_1$-$C_4$alkoxy, $(CO)OH$ or $(CO)O(C_1$-$C_4$alkyl); or $R_{10}$, $R_{11}$, $R_{12}$ and $R_{13}$ are phenyl which optionally is substituted by one or more $C_1$-$C_6$alkyl, halogen, CN, $OR_3$, $SR_4$ or $NR_5R_6$; or $R_{10}$, $R_{11}$, $R_{12}$ and $R_{13}$ are halogen, CN, $OR_3$, $SR_4$ or $NR_5R_6$;

$R_{14}$ and $R_{15}$ independently of each other are hydrogen, $C_1$-$C_{12}$alkyl which optionally is substituted by one or more halogen, phenyl, CN, OH, SH, $C_1$-$C_4$alkoxy, $(CO)OH$ or $(CO)O(C_1$-$C_4$alkyl); or $R_{14}$ and $R_{15}$ are phenyl which optionally is substituted by one or more $C_1$-$C_6$alkyl, halogen, CN, $OR_3$, $SR_4$ or $NR_5R_6$;

$R_{17}$ and $R_{18}$ independently of each other are hydrogen, $C_1$-$C_{20}$alkyl, $C_1$-$C_4$haloalkyl, $C_3$-$C_{10}$cycloalkyl or phenyl; or $R_{17}$ and $R_{18}$ together with N-atom to which they are attached form a 5- or 6-membered saturated or unsaturated ring, which optionally is interrupted by O, S or $NR_{24}$;

or $R_{17}$ and $R_{18}$ independently of one another are $C_2$-$C_5$alkylene or $C_2$-$C_5$alkenylene which is attached to one of the C-atoms of the phenyl or naphthyl ring to which the $NR_{17}R_{18}$ is attached, wherein said $C_2$-$C_5$alkylene or $C_2$-$C_5$alkenylene optionally is interrupted by O, CO or $NR_{24}$, and to which $C_2$-$C_5$alkylene or $C_2$-$C_5$alkenylene optionally a benzene ring is condensed;

$R_{19}$ is hydrogen, OH, $C_1$-$C_{20}$alkyl, $C_1$-$C_4$haloalkyl, $C_2$-$C_{20}$alkyl which is interrupted by O, CO or $NR_{24}$, $C_3$-$C_{20}$cycloalkyl which optionally is interrupted by O, S, CO or $NR_{24}$, or is phenyl, naphthyl, phenyl-$C_1$-$C_4$alkyl, $SR_4$, $OR_3$ or $NR_{17}R_{18}$;

$R_{20}$ is $COOR_3$, $CONR_5R_6$, $(CO)R_1$;

or $R_{20}$ has one of the meanings as given for $R_5$ and $R_6$;

$R_{21}$ is $COOR_3$, $CONR_5R_6$, $(CO)R_1$;

or $R_{21}$ has one of the meanings as given for $R_3$;

$R_{22}$ is hydrogen, $C_1$-$C_{20}$alkyl; $C_2$-$C_{20}$alkenyl; $C_3$-$C_{20}$cycloalkyl which optionally is interrupted by O, S, CO or $NR_{24}$, or is $C_3$-$C_{10}$cycloalkenyl; or is $C_1$-$C_{20}$alkyl which is substituted by one or more halogen, $SR_4$, $OR_3$, $COOR_3$, $NR_5R_6$, $C_1$-$C_{20}$heteroaryl, $C_1$-$C_{20}$heteroaryl-$(CO)O$, $CONR_5R_6$,

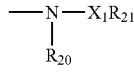

or phenyl; or $R_{22}$ is $C_2$-$C_{20}$alkyl which is interrupted by one or more O and/or optionally is substituted by one or more halogen, $SR_4$, $OR_3$, $COOR_3$, $NR_5R_6$, $C_1$-$C_{20}$heteroaryl, $C_1$-$C_{20}$heteroaryl-$(CO)O$, $CONR_5R_6$,

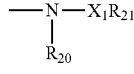

or phenyl;

or $R_{22}$ is phenyl, naphthyl, coumarinyl or $C_1$-$C_{20}$heteroaryl, each of which optionally is substituted by one or more $C_1$-$C_{12}$alkyl, phenyl, halogen, $C_1$-$C_4$haloalkyl, CN, $NO_2$, $SR_4$, $OR_3$, $NR_5R_6$ or by $C_3$-$C_{20}$cycloalkyl which optionally is interrupted by O, CO or $NR_5$;

or $R_{22}$ is $C_2$-$C_{20}$alkanoyl, or benzoyl which is unsubstituted or substituted by one or more $C_1$-$C_6$alkyl, halogen, phenyl, $SR_4$, $OR_3$ or $NR_5R_6$;

or $R_{22}$ is $C_2$-$C_{12}$alkoxycarbonyl which optionally is interrupted by one or more O and/or optionally is substituted by one or more OH;

or $R_{22}$ is phenoxycarbonyl which is unsubstituted or substituted by one or more $C_1$-$C_6$alkyl, $C_1$-$C_4$haloalkyl, halogen, phenyl, $SR_4$, $OR_3$ or $NR_5R_6$;

or $R_{22}$ is $NR_5R_6$;

or $R_{22}$ forms a ring with one of the C-atoms of the phenyl ring to which the group

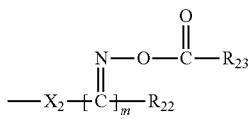

is attached, wherein said formed ring is unsubstituted or substituted;

$R_{23}$ has one of the meanings as given for $R_1$; and $R_{24}$ is hydrogen, $C_1$-$C_{20}$alkyl, $C_1$-$C_4$haloalkyl, $C_2$-$C_{20}$alkyl which is interrupted by O, S or CO, or is phenyl-$C_1$-$C_4$alkyl, $C_3$-$C_{20}$cycloalkyl which optionally is interrupted by O, S or CO, or is phenyl.

Further subject of the invention is a photopolymerizable composition comprising (a) at least one ethylenically unsaturated photopolymerizable compound and (b) a photoinitiator mixture as defined above, as well as a photopolymerizable composition comprising (a) at least one ethylenically unsaturated photopolymerizable aminoacrylate compound or at least one ethylenically unsaturated photopolymerizable acrylate and a H-donor and (b1) a photoinitiator mixture consisting of at least one compound of the formula I or I' as defined above and a benzophenone compound or a thioxanthone compound; and optionally (d) other additives.

To be used in the photopolymerizable composition, each component of the photoinitiator mixture, that is the compound of the formula (I) or (I') and the compound selected from the group consisting of alpha-hydroxy ketones (HK), monoacylphosphine oxides (MPO), bisacylphosphine oxides (BPO), benzophenones (BP), thioxanthones (TX), ketosulfones (KS), benzil ketals (BK), benzoin ether (BK), phenylglyoxylates (PG), borates (BT) and titanocenes (TI) can be added in a stepwise manner to the formulation. It is, however, also possible to make a mixture of the oxime ester (I) or (I') and (HK), (MPO), (BPO), (BP), (TX), (KS), (BK), (PG), (BT) and/or (TI) by various methods prior to the use in the photopolymerizable composition. Methods to prepare such mixtures are known to the person skilled in the art. For example, every component is dissolved in a solvent to make a homogeneous solution, which is concentrated to dryness to give a mixture, or, filtration of a dispersion, wherein every component is dispersed in a poor solvent or a reactive diluent, gives the desired mixture. It is also possible to mix every component by using a blender. Another method is, for example, to dissolve the oxime ester compound(s) (I) or (I') in melted alpha-hydroxy keton compound(s) (HK), (MPO), (BPO), (BP), (TX), (KS), (BK), (PG), (BT) and/or (TI) at a temperature, that is higher than its melting point, or the other way around. Cooling the liquid to room temperature gives a mixture according to the present invention.

The ratio of the compound of the formula (I) or (I') and the compound of the formula (HK), (MPO), (BPO), (BP), (TX), (KS), (BK), (PG), (BT) and/or (TI) is for example from 0.1:99.9 to 50:50, especially 0.5:99.5 to 40:60, in particular 1:99 to 20:80.

Oxime esters of formula (I) or (I') are prepared from the corresponding oximes by methods described in the literature, for example by reaction of the corresponding oximes with an acyl halide, in particular a chloride, or an anhydride in an inert solvent such as for example diethyl ether, t-butyl methyl ether, tetrahydrofurane (THF), ethyl acetate, toluene, xylenes, acetone, methyl ethyl ketone, dichloromethane, chloroform, chlorobenzene, dimethylacetoamide or dimethylformamide in the presence of a base, for example triethylamine, diisopropylethyl-amine, potassium hydroxide, sodium hydroxide, sodium hydride, 2,6-lutidine or pyridine, or in a basic solvent such as pyridine. For example:

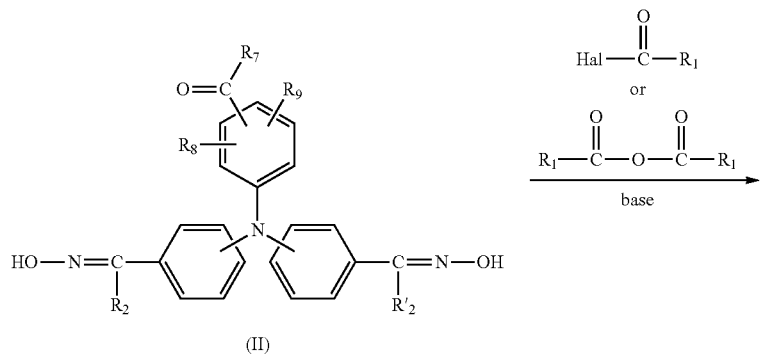

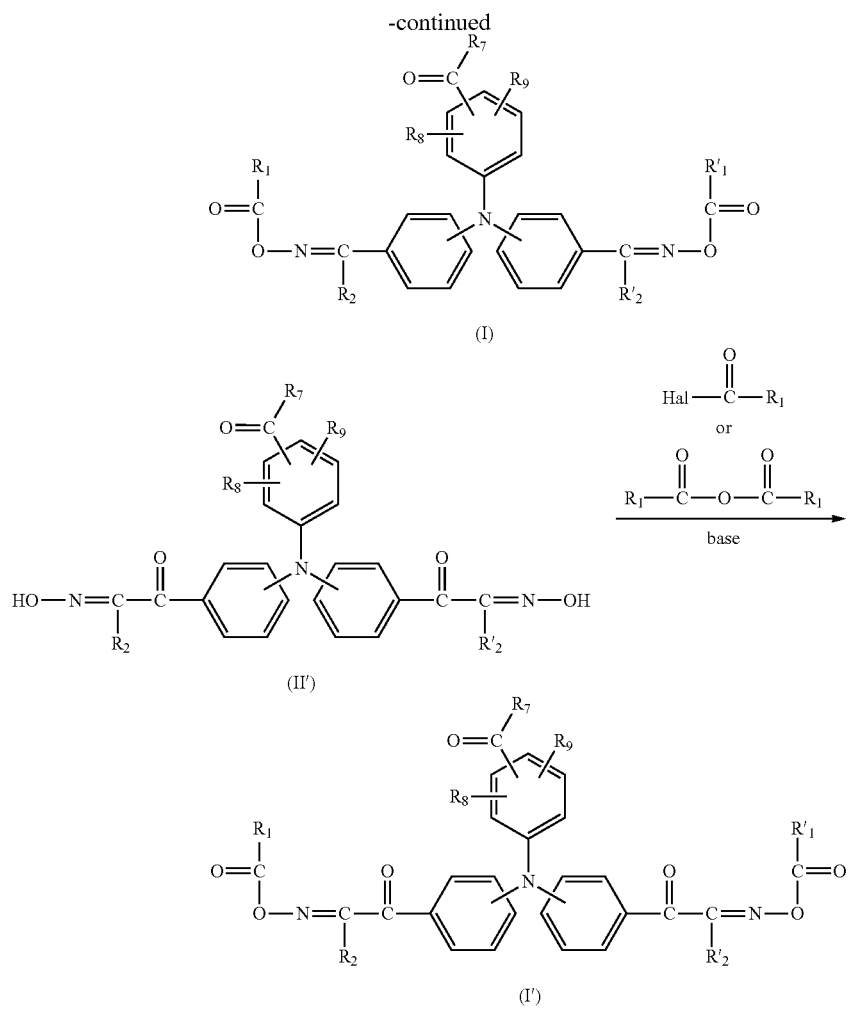

$R_1$, $R_2$, $R'_1$, $R'_2$, $R_7$, $R_8$ and $R_9$ are as defined above, Hal means a halogen atom, in particular Cl. Compounds of the formula I or I', wherein $R_1$ and $R'_1$ are not identical, can be prepared by using a mixture of the corresponding acyl halides, or by stepwise esterification. Such reactions are well known to those skilled in the art, and are generally carried out at temperatures of −15 to +50° C., preferably 0 to 25° C.

The compounds of formula (II) or (II') can be for example synthesized from the corresponding ketones in a selective manner according to the scheme below.

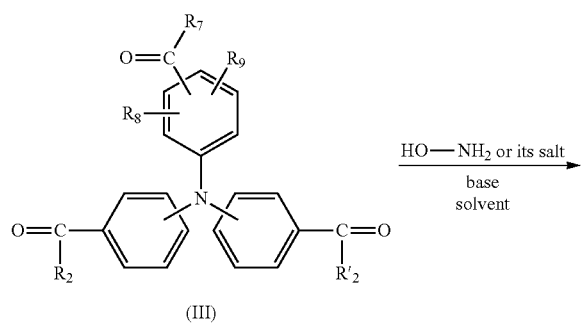

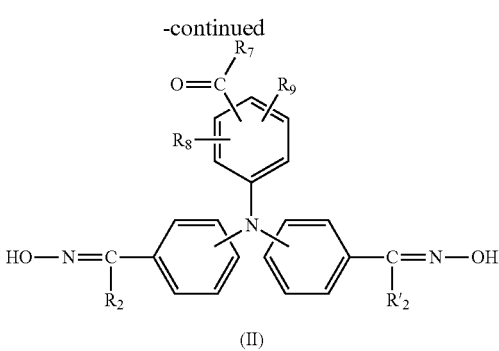

$R_2$, $R'_2$, $R_7$, $R_8$ and $R_9$ are as defined above.

Another convenient synthesis of oximes is the nitrosation of "active" methylene groups with nitrous acid or an alkyl nitrite. Both alkaline conditions, as described for example in Organic Syntheses coll. Vol. VI (J. Wiley & Sons, New York, 1988), pp 199 and 840, and acidic conditions, as described, for example, in Organic Synthesis coll. vol V, pp 32 and 373, coll. vol. III, pp 191 and 513, coll. vol. II, pp. 202, 204 and 363, are suitable for the preparation of the oximes used as starting materials in the invention. Nitrous acid is usually generated from sodium nitrite. The alkyl nitrite can be for example methyl nitrite, ethyl nitrite, isopropyl nitrite, butyl nitrite, or isoamyl nitrite.

Every oxime ester group can exist in two configurations, (Z) or (E). It is possible to separate the isomers by conventional methods, but it is also possible to use the isomeric mixture as such as photoinitiating species. Therefore, the invention also relates to photoinitiator mixtures as oxime ester component comprising mixtures of configurational isomers of compounds of the formula (I) or (I').

Interesting are compounds of the formula (I) or (I'), wherein the group $CO(R_7)$ is bound in para-position to the N-phenyl bond, i.e. a compound of the formula (Ia) or (I'a):

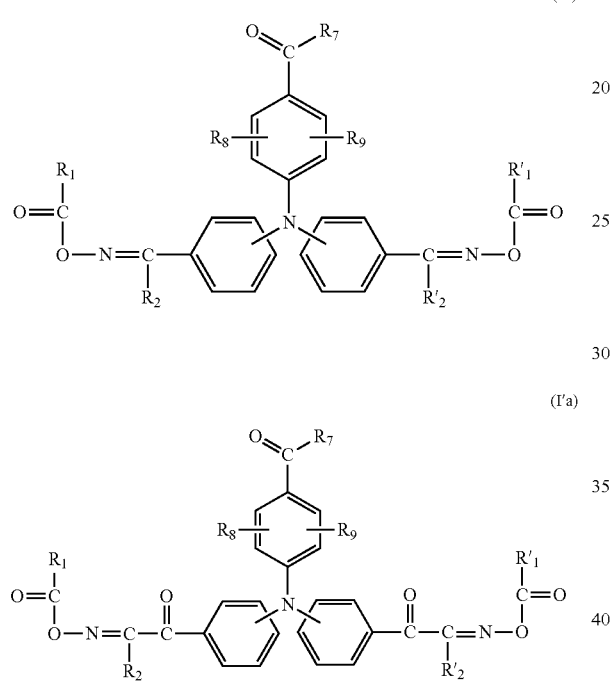

(Ia)

(I'a)

wherein $R_1$, $R'_1$, $R_2$, $R'_2$, $R_7$, $R_8$ and $R_9$ are as defined above.

Interesting are compounds of the formula (I) or (I'), wherein the bond of the central N-atom is in para-position of the phenyl ring to the bond of the oxime ester group, i.e. a compound of the formula (Ib) or (I'b):

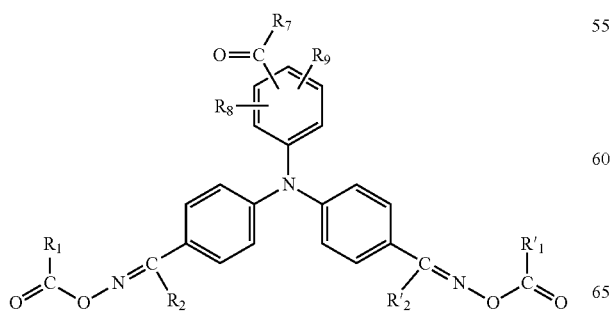

(Ib)

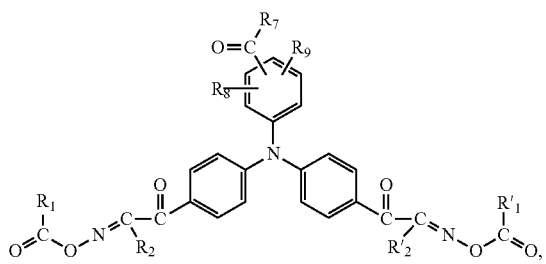

(I'b)

wherein $R_1$, $R'_1$, $R_2$, $R'_2$, $R_7$, $R_8$ and $R_9$ are as defined above.

Preferred are compounds of the formula (I) or (I'), wherein the group $CO(R_7)$ is bound in para-position to the N-phenyl bond and wherein the bond of the central N-atom is in para-position of the phenyl ring to the bond of the oxime ester group, i.e. a compound of the formula (Ic) or (I'c):

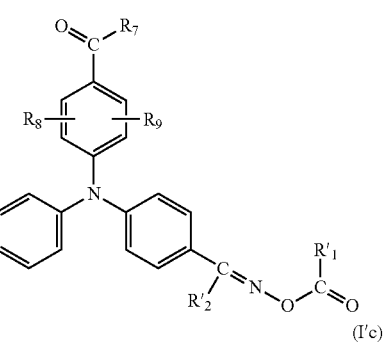

(Ic)

(I'c)

wherein $R_1$, $R'_1$, $R_2$, $R'_2$, $R_7$, $R_8$ and $R_9$ are as defined above.

$R_1$ and $R'_1$ are for example hydrogen, $C_3$-$C_8$cycloalkyl, unsubstituted $C_1$-$C_{12}$alkyl or $C_1$-$C_{12}$alkyl which is substituted as indicated above; or are phenyl which is unsubstituted or substituted by one or more $C_1$-$C_6$alkyl, halogen, CN, $OR_3$, $SR_4$ and/or $NR_5R_6$; in particular $R_1$ and $R'_1$ are $C_3$-$C_8$cycloalkyl, $C_1$-$C_{12}$alkyl or phenyl, preferably $C_1$-$C_{12}$alkyl, in particular $C_1$-$C_4$alkyl, especially methyl.

Preferably $R_2$ and $R'_2$ are $C_1$-$C_{20}$alkyl which is unsubstituted or substituted by halogen, $OR_3$, $COOR_3$, $SR_4$, phenyl, $NR_5R_6$ or

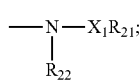

or are unsubstituted phenyl or phenyl which is substituted by one or more $C_1$-$C_6$alkyl, $SR_4$, $OR_3$ or $NR_5R_6$. In particular $R_2$ and $R'_2$ are $C_1$-$C_{20}$alkyl which is unsubstituted or is substituted by $COOR_3$ or

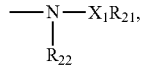

or are especially $C_1$-$C_8$alkyl which is unsubstituted or is substituted by $COOR_3$ or

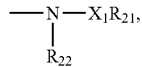

or are for example methyl, butyl or heptyl.

$X_1$ preferably is O.

$R_{21}$ and $R_{22}$ preferably are $(CO)R_1$.

$R_3$ is for example $C_1$-$C_{20}$alkyl, $C_1$-$C_8$alkanoyl, phenyl-$C_1$-$C_3$alkyl, $C_3$-$C_{20}$cycloalkyl which is uninterrupted or interrupted by O, or is phenyl, $C_1$-$C_{20}$heteroaryl. Preferably $R_3$ is $C_1$-$C_{20}$alkyl or $C_3$-$C_8$cycloalkyl which optionally is interrupted by one or more O, in particular it is $C_1$-$C_8$alkyl or $C_3$-$C_6$cycloalkyl which is interrupted by O.

$R_4$ is preferably $C_1$-$C_{20}$alkyl, $C_1$-$C_8$alkanoyl, phenyl-$C_1$-$C_3$alkyl, $C_1$-$C_{20}$heteroaryl, unsubstituted phenyl or phenyl substituted by $C_1$-$C_{20}$alkyl, halogen,

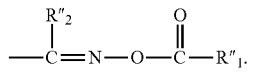

$R_5$ and $R_6$ are for example hydrogen, $C_1$-$C_{20}$alkyl, $C_2$-$C_4$hydroxyalkyl, $C_2$-$C_{10}$alkoxyalkyl, phenyl-$C_1$-$C_3$alkyl, phenyl, or together with the N-atom to which they are attached form a 5- or 6-membered saturated or unsaturated ring which optionally is interrupted by O, or preferably hydrogen, phenyl, $C_1$-$C_{20}$alkyl; or together with the N-atom to which they are attached form a heteroaromatic ring system, in particular carbazolyl.

$R_7$ in particular denotes phenyl, naphthyl or $C_1$-$C_{20}$heteroaryl, phenyl substituted by one or more $SR_4$, $OR_3$, $NR_5R_6$, halogen, $C_1$-$C_8$alkyl or CN; especially unsubstituted phenyl, phenyl substituted by $SR_4$, $NR_5R_6$, $C_1$-$C_8$alkyl, CN or one or more $OR_3$ or halogen, naphthyl or $C_1$-$C_{20}$heteroaryl (for example thienyl).

$R_8$ and $R_9$ preferably are hydrogen.

Preferred are compounds of the formula (I), (Ia), (Ib) and (Ic).

In particular preferred in the photoinitiator mixture as described above are as oxime compounds of formula (I) or (I')

(1)

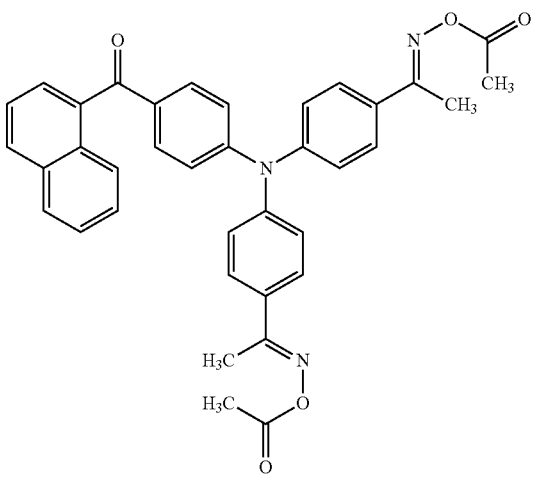

(2)

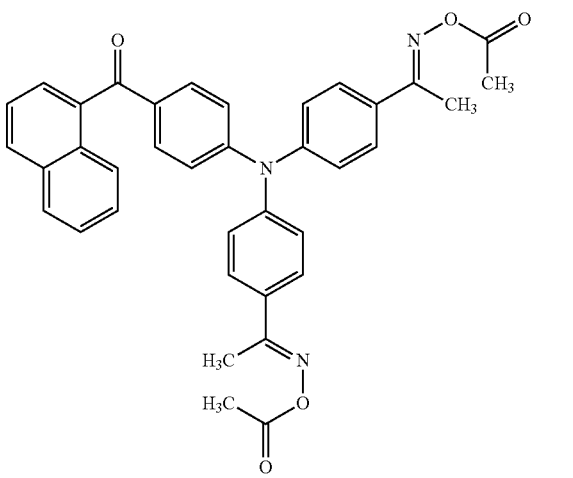

(3)

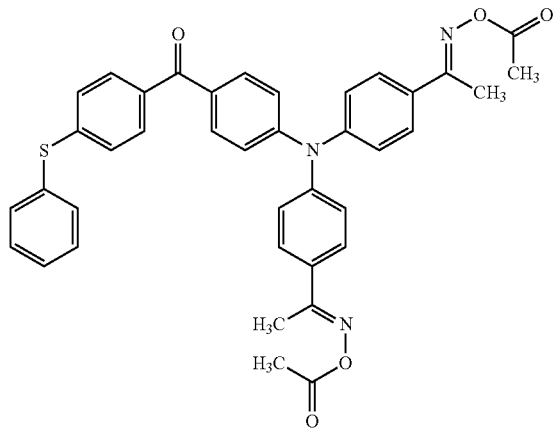

(4)

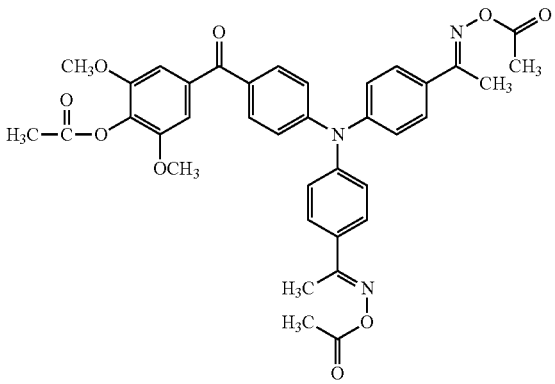

-continued
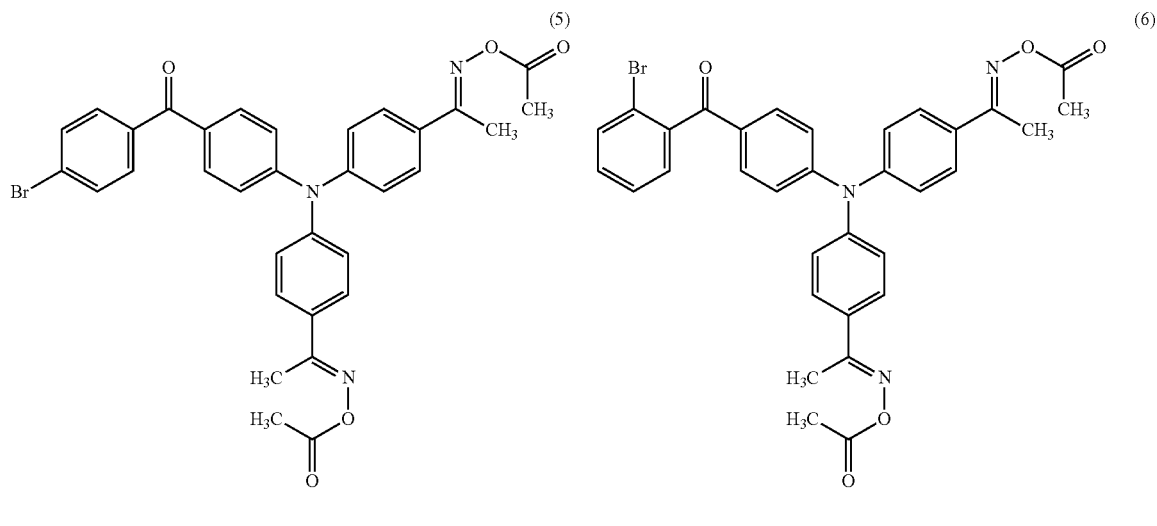 [SMILES: CC(=O)O/N=C(\C)c1ccc(N(c2ccc(C(=O)c3ccc(Br)cc3)cc2)c2ccc(/C(C)=N/OC(C)=O)cc2)cc1 ; CC(=O)O/N=C(\C)c1ccc(N(c2ccc(C(=O)c3ccccc3Br)cc2)c2ccc(/C(C)=N/OC(C)=O)cc2)cc1]
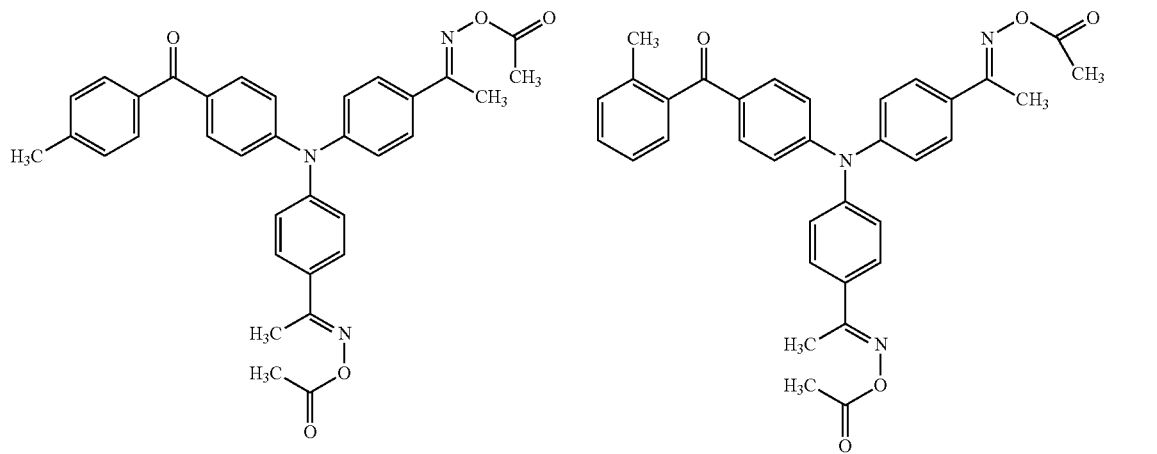
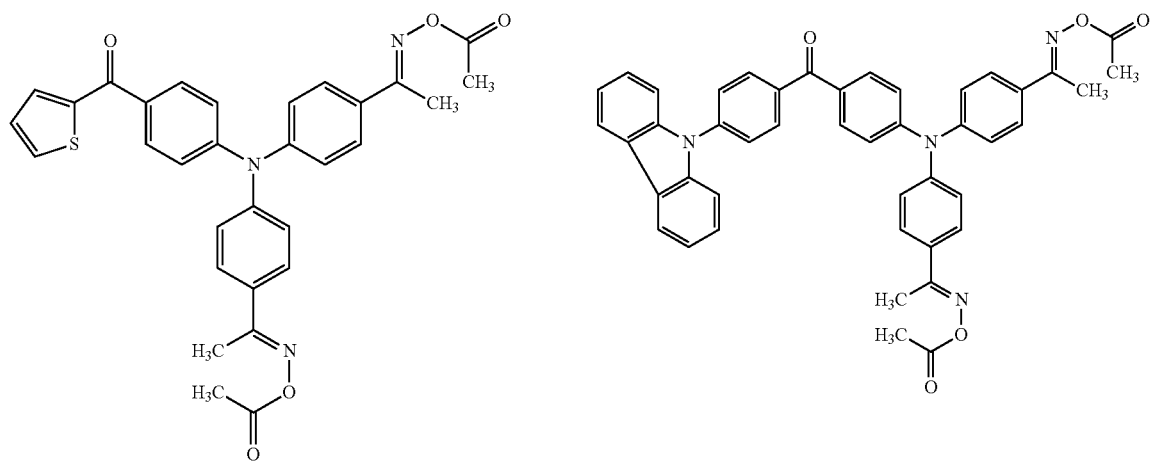

-continued
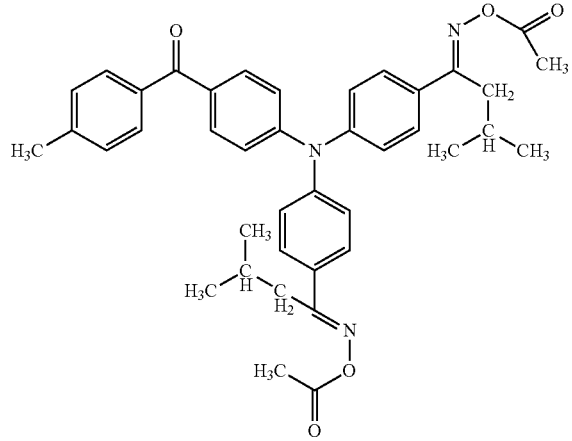
(11)
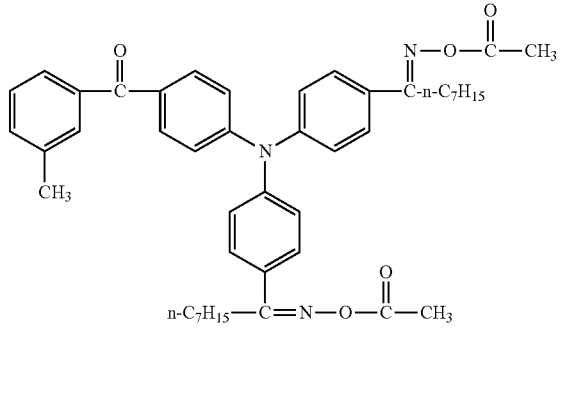
(12)
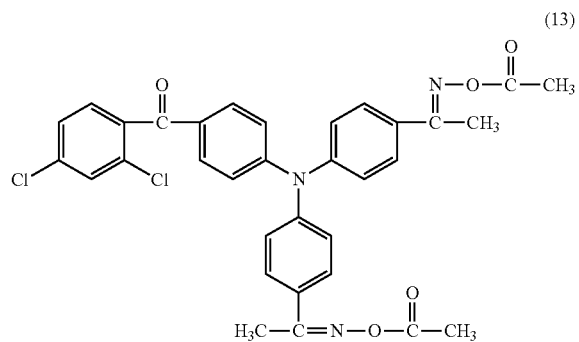
(13)
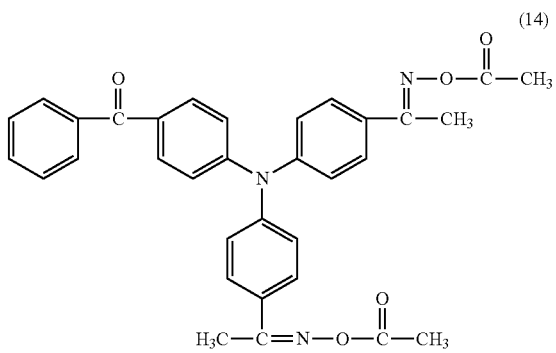
(14)
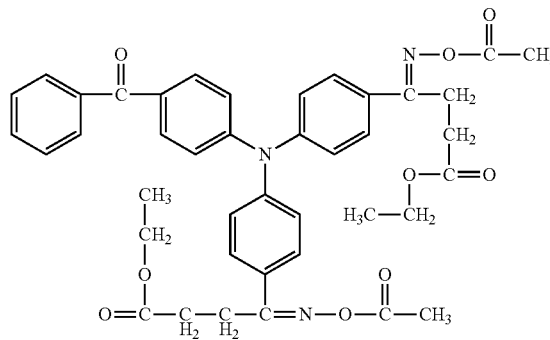
(15)
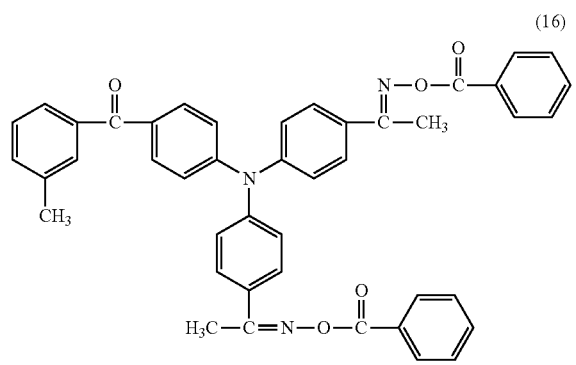
(16)
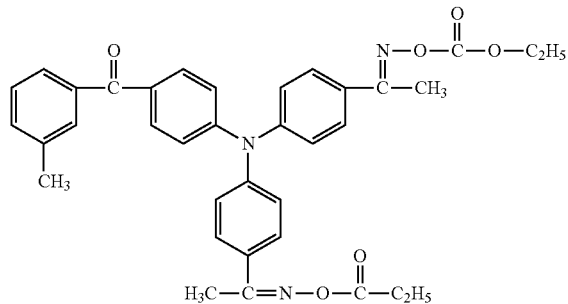
(17)
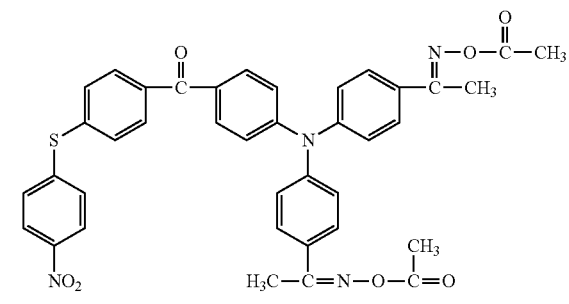
(18)

-continued
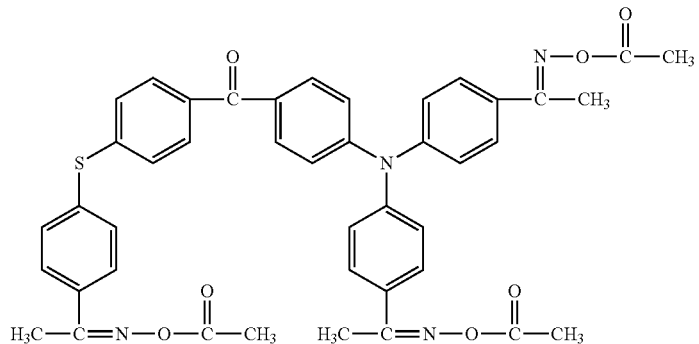
(19)
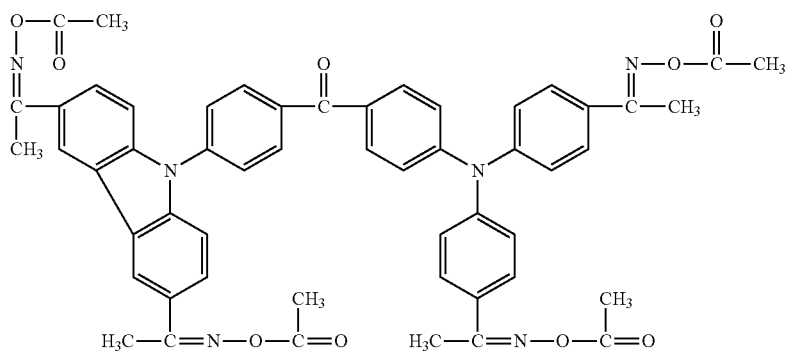
(20)
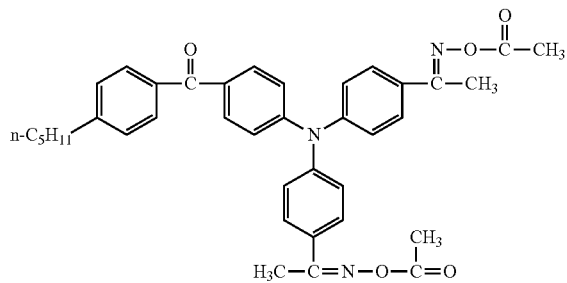
(21)
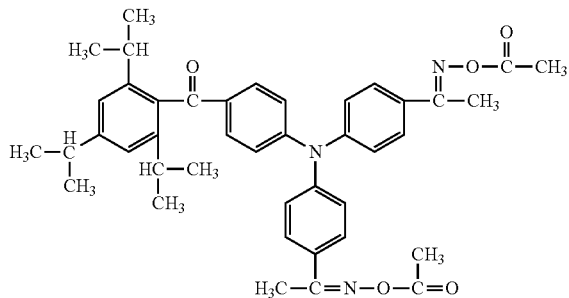
(22)
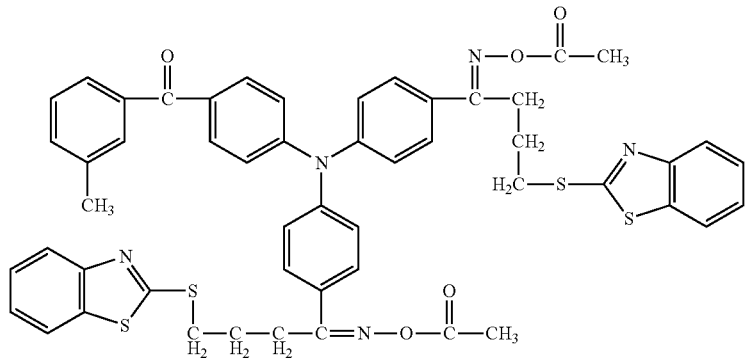
(23)

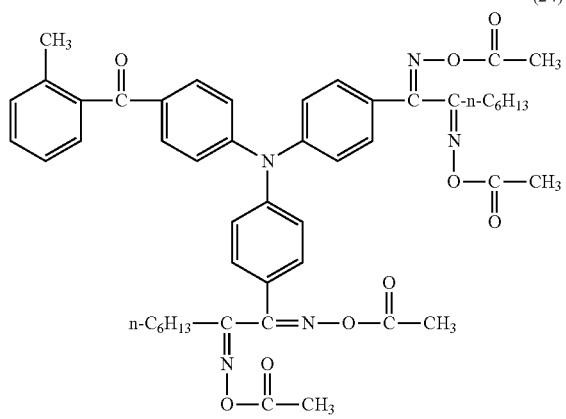

(24)

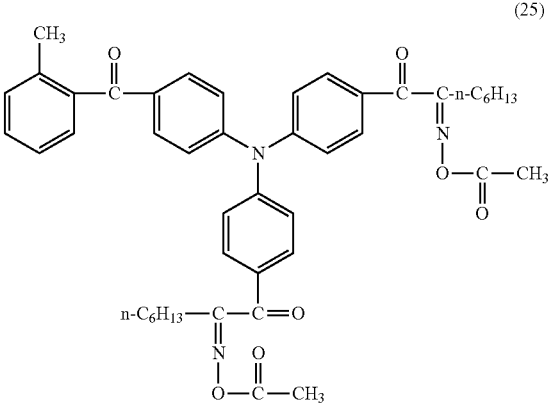

(25)

Especially preferred are the above compounds of formula (I), that is the compounds of the above structures (1)-(24).

In particular preferred are the compounds (1), (2), (7), (8), (9), (12) and (14).

In accordance with the invention a combination of the compounds of the formula I or I' and the known photoinitiator compounds selected from the group consisting of alpha-hydroxy ketones, monoacylphosphine oxides, bisacylphosphine oxides, ketosulfones, benzil ketals, phenylglyoxylates, borates and titanocenes is used as a photoinitiator mixture for the polymerization of ethylenically unsaturated components and a combination of compounds of the formula I and benzophenones or thioxanthones is used for the polymerization of (1) at least one ethylenically unsaturated photopolymerizable aminoacrylate compound or (2) an ethylenically unsaturated component in the presence of a co-initiator. The co-initiator is for example a tertiary amine, triethanolamine, N-methyldiethanolamine, p-dimethylamino-benzoate or Michler's ketone; other coinitiators are for example thiols, thioethers, disulfides, phosphonium salts, phosphine oxides or phosphines, as described, for example, in EP 438123, in GB 2180358 and in JP Kokai Hei 6-68309.

The alpha-hydroxy ketone compound in the photoinitiator mixture as described above for example is of the formula (HK),

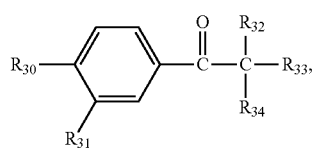

(HK)

wherein
$R_{31}$ is hydrogen or $C_1$-$C_{18}$-alkoxy;
$R_{30}$ is hydrogen, $C_1$-$C_{18}$-alkyl, $C_1$-$C_{12}$hydroxyalkyl, $C_1$-$C_{18}$-alkoxy, —O(CH$_2$CH$_2$O)$_q$—R$_{35}$, $C_1$-$C_{18}$alkyl-S—, H$_2$C=CH—, H$_2$C=C(CH$_3$)—, NR$_{36}$R$_{37}$,

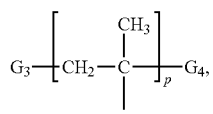

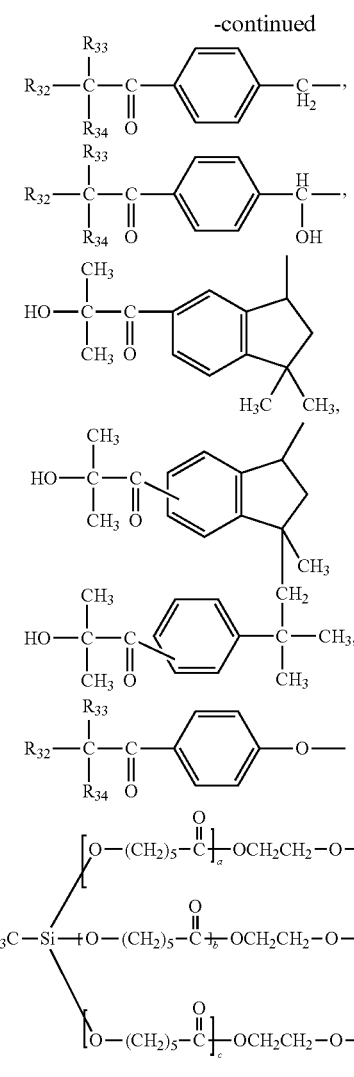

a, b and c are 1-3;
p is 2-10;
q is 1-20;
$G_3$ and $G_4$ independently of one another are end groups of the polymeric structure, preferably hydrogen or methyl;

$R_{32}$ is hydroxy, $C_1$-$C_{16}$-alkoxy, or —O(CH$_2$CH$_2$O)$_q$—$C_1$-$C_{16}$-alkyl;

$R_{33}$ and $R_{34}$ independently of one another are hydrogen, $C_1$-$C_6$-alkyl, $C_1$-$C_{16}$-alkoxy or —O(CH$_2$CH$_2$O)$_q$—$C_1$-$C_{16}$-alkyl; or unsubstituted phenyl or benzyl; or phenyl or benzyl substituted by $C_1$-$C_{12}$-alkyl; or $R_{33}$ and $R_{34}$ together with the carbon atom to which they are attached form a cyclohexyl ring;

with the proviso that $R_{32}$, $R_{33}$ and $R_{34}$ not all together are $C_1$-$C_{16}$-alkoxy or —O(CH$_2$CH$_2$O)$_q$—$C_1$-$C_{16}$-alkyl;

$R_{35}$ is hydrogen,

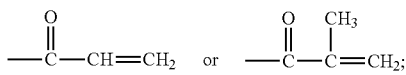

$R_{36}$ and $R_{37}$ independently of each other are hydrogen, $C_1$-$C_{20}$alkyl, $C_1$-$C_{20}$hydroxyalkyl, $C_1$-$C_{20}$alkyl interrupted by one or more O or NR$_{38}$, wherein the interrupted $C_1$-$C_{20}$alkyl optionally is substituted by one or more OH; and $R_{38}$ is hydrogen $C_1$-$C_{20}$alkyl or $C_1$-$C_{20}$alkyl interrupted by one or more O.

Preferred are compounds of the formula (HK), wherein $R_{31}$ is hydrogen or $C_1$-$C_{18}$-alkoxy;

$R_{30}$ is hydrogen, $C_1$-$C_{18}$-alkyl, $C_1$-$C_{12}$hydroxyalkyl, $C_1$-$C_{18}$-alkoxy, —O(CH$_2$CH$_2$O)$_q$—$R_{35}$, NR$_{36}$R$_{37}$,

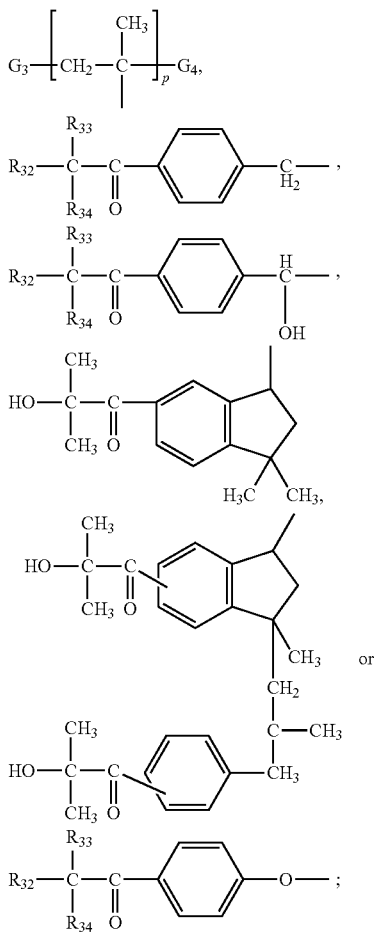

p is 2-10;

q is 1-20;

$G_3$ and $G_4$ independently of one another are end groups of the polymeric structure, preferably hydrogen or methyl;

$R_{32}$ is hydroxy or —O(CH$_2$CH$_2$O)$_q$—$C_1$-$C_{16}$-alkyl;

$R_{33}$ and $R_{34}$ independently of one another are $C_1$-$C_6$-alkyl, or $R_{33}$ and $R_{34}$ together with the carbon atom to which they are attached form a cyclohexyl ring;

$R_{35}$ is hydrogen,

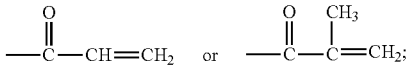

$R_{36}$ and $R_{37}$ independently of each other are hydrogen, $C_1$-$C_{20}$alkyl, $C_1$-$C_{20}$hydroxyalkyl, $C_1$-$C_{20}$alkyl interrupted by one or more O or NR$_{38}$, wherein the interrupted $C_1$-$C_{20}$alkyl optionally is substituted by one or more OH; and $R_{38}$ is hydrogen $C_1$-$C_{20}$alkyl or $C_1$-$C_{20}$alkyl interrupted by one or more O.

Specific examples are:

1-Hydroxy-cyclohexyl-phenyl-ketone,

1-[4-(2-hydroxyethoxy)-phenyl]-2-hydroxy-2-methyl-1-propan-1-one, 2-hydroxy-2-methyl-1-phenyl-propan-1-one, 2-hydroxy-1-{4-[4-(2-hydroxy-2-methyl-propionyl)-benzyl]-phenyl}-2-methyl-propan-1-one, 2-hydroxy-1-{4-[4-(2-hydroxy-2-methyl-propionyl)-phenoxy]-phenyl}-2-methyl-propan-1-one,

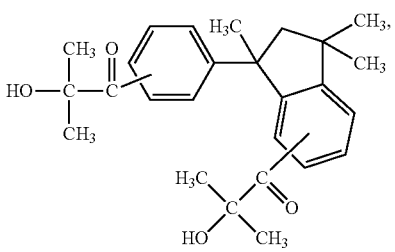

oligo[2-hydroxy-2-methyl-1[4-(1-methylvinyl)phenyl]propanone], 2-hydroxy-1-{1-[4-(2-hydroxy-2-methyl-propionyl)-phenyl]-1,3,3-trimethyl-indan-5-yl}-2-methyl-propan-1-one.

Compounds of the formula (HK) are known in the art and the compounds as well as their preparation are for example described in U.S. Pat. Nos. 4,347,111, 4,321,118, WO 04/092287, U.S. Pat. Nos. 4,672,079, 4,987,159 and WO 02/85832, the disclosure of which hereby is incorporated by reference. The person skilled in the art is well aware of such compounds, as a host of the compounds also is commercially available, for example under the trademarks IRGACURE® and DAROCUR®, provided by Ciba Inc.; ESACURE®, provided by Lamberti SPA.

The monoacylphosphine oxide compound in the photoinitiator mixture as described above for example is of the formula (MPO),

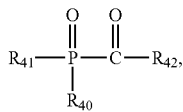

(MPO)

wherein $R_{40}$ and $R_{41}$ independently of one another are unsubstituted $C_1$-$C_{20}$-alkyl, cyclohexyl, cyclopentyl, phenyl, naphthyl or biphenylyl; or $C_1$-$C_{20}$-alkyl, cyclohexyl, cyclopentyl, phenyl, naphthyl or biphenylyl substituted by one or more halogen, $C_1$-$C_{12}$-alkyl, $C_1$-$C_{12}$-alkoxy, $C_1$-$C_{12}$alkylthio or $NR_{43}R_{44}$; or are $OC_1$-$C_{12}$alkyl;

$R_{42}$ is unsubstituted cyclohexyl, cyclopentyl, phenyl, naphthyl or biphenylyl, or cyclohexyl, cyclopentyl, phenyl, naphthyl or biphenylyl substituted by one or more halogen, $C_1$-$C_4$-alkyl or $C_1$-$C_4$-alkoxy; or $R_{42}$ is a 5- or 6-membered heterocyclic ring comprising an S atom or N atom; and $R_{43}$ and $R_{44}$ independently of one another are hydrogen, unsubstituted $C_1$-$C_{12}$-alkyl or $C_1$-$C_{12}$-alkyl substituted by OH or SH wherein the alkyl chain optionally is interrupted by one to four oxygen atoms; or $R_{43}$ and $R_{44}$ independently of one another are $C_2$-$C_{12}$-alkenyl, cyclopentyl, cyclohexyl, benzyl or phenyl.

Preferred are compounds of the formula (MPO), wherein $R_{40}$ and $R_{41}$ independently of one another are unsubstituted phenyl or $OC_1$-$C_8$alkyl; and $R_{42}$ is phenyl substituted by one or more halogen, $C_1$-$C_4$-alkyl or $C_1$-$C_4$-alkoxy; or $R_{42}$ is a 5- or 6-membered heterocyclic ring comprising an S atom or N atom; and Specific examples are:

2,4,6-trimethylbenzoyl-diphenyl-phosphine oxide;

ethyl(2,4,6 trimethylbenzoyl phenyl)phosphinic acid ester.

Compounds of the formula (MPO) are known in the art and the compounds as well as their preparation is for example described in U.S. Pat. No. 4,324,744 and EP 40721 (=Derwent 91349 D/50). The person skilled in the art is familiar with such compounds and several of the compounds also are commercially available, for example under the trademarks DAROCUR® and IRGACURE® provided by Ciba Inc.

The bisacylphosphine oxide compound in the photoinitiator mixture as described above for example is of the formula (BPO),

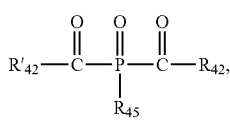

(BPO)

wherein $R_{42}$ and $R'_{42}$ independently of one another are unsubstituted cyclohexyl, cyclopentyl, phenyl, naphthyl or biphenylyl, or are cyclohexyl, cyclopentyl, phenyl, naphthyl or biphenylyl substituted by one or more halogen, $C_1$-$C_4$-alkyl or $C_1$-$C_4$-alkoxy; or $R_{42}$ is a 5- or 6-membered heterocyclic ring comprising an S atom or N atom; and $R_{45}$ is unsubstituted $C_1$-$C_{20}$-alkyl, $C_2$-$C_{20}$-alkenyl, $C_1$-$C_{20}$-alkyl substituted by one or more halogen, $C_1$-$C_{12}$-alkoxy, $C_1$-$C_{12}$alkylthio, $NR_{43}R_{44}$ or $(CO)OR_{46}$, or $R_{45}$ is unsubstituted cyclohexyl, cyclopentyl, phenyl, naphthyl or biphenylyl; or is cyclohexyl, cyclopentyl, phenyl, naphthyl or biphenylyl substituted by one or more halogen, $C_1$-$C_{12}$-alkyl, $C_2$-$C_{20}$-alkenyl, $C_1$-$C_{12}$-alkoxy, $C_1$-$C_{12}$alkylthio or $NR_{43}R_{44}$;

$R_{43}$ and $R_{44}$ independently of one another are hydrogen, unsubstituted $C_1$-$C_{12}$-alkyl or $C_1$-$C_{12}$-alkyl substituted by OH or SH wherein the alkyl chain optionally is interrupted by one to four oxygen atoms; or $R_{43}$ and $R_{44}$ independently of one another are $C_2$-$C_{12}$-alkenyl, cyclopentyl, cyclohexyl, benzyl or phenyl; and $R_{46}$ is $C_1$-$C_{20}$-alkyl or $C_2$-$C_{20}$-alkenyl.

Preferred are compounds of the formula (BPO), wherein $R_{42}$ and $R'_{42}$ independently of one another are phenyl substituted by one or more halogen, $C_1$-$C_4$-alkyl or $C_1$-$C_4$-alkoxy;

$R_{45}$ is unsubstituted $C_1$-$C_{20}$-alkyl, $C_1$-$C_{20}$-alkyl substituted by $(CO)OR_{46}$, or $R_{45}$ is unsubstituted phenyl or phenyl, substituted by one or more $C_1$-$C_{12}$-alkoxy; and $R_{46}$ is $C_1$-$C_{20}$-alkyl.

Specific examples are bis(2,4,6-trimethylbenzoyl)-phenylphosphine oxide;

bis(2,4,6-trimethylbenzoyl)-2,4-dipentoxyphenylphosphine oxide, bis(2,6-dimethoxybenzoyl)-2,4,4-trimethylpentylphosphine oxide.

Compounds of the formula (BPO) are known in the art and the compounds as well as their preparation is for example described in U.S. Pat. No. 4,737,593, GB 2259704, WO 00/32612 or WO 05/014605. Several of the compounds also are commercially available, for example under the trademark IRGACURE® provided by Ciba Inc.

The benzophenone compound in the photoinitiator mixture as described above for example is of the formula (BP)

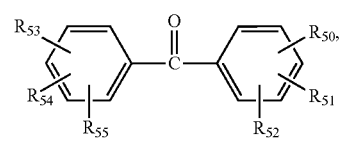

(BP)

wherein $R_{50}$, $R_{51}$, $R_{52}$, $R_{53}$, $R_{54}$ and $R_{55}$ independently of one another are hydrogen, $C_1$-$C_{12}$-alkyl, $C_1$-$C_4$-halogenalkyl, halogen, $N(C_1$-$C_4$-alkyl$)_2$, phenyl, $(CO)OR_{56}$, $OR_{57}$, $C_1$-$C_{12}$alkyl which is substituted by

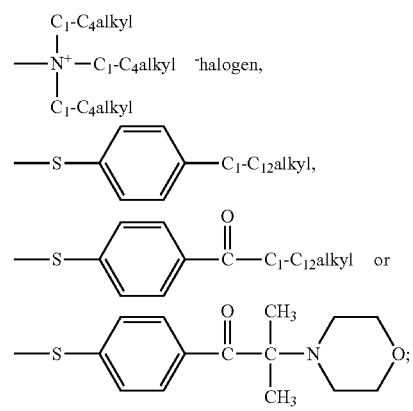

or R$_{50}$ additionally is

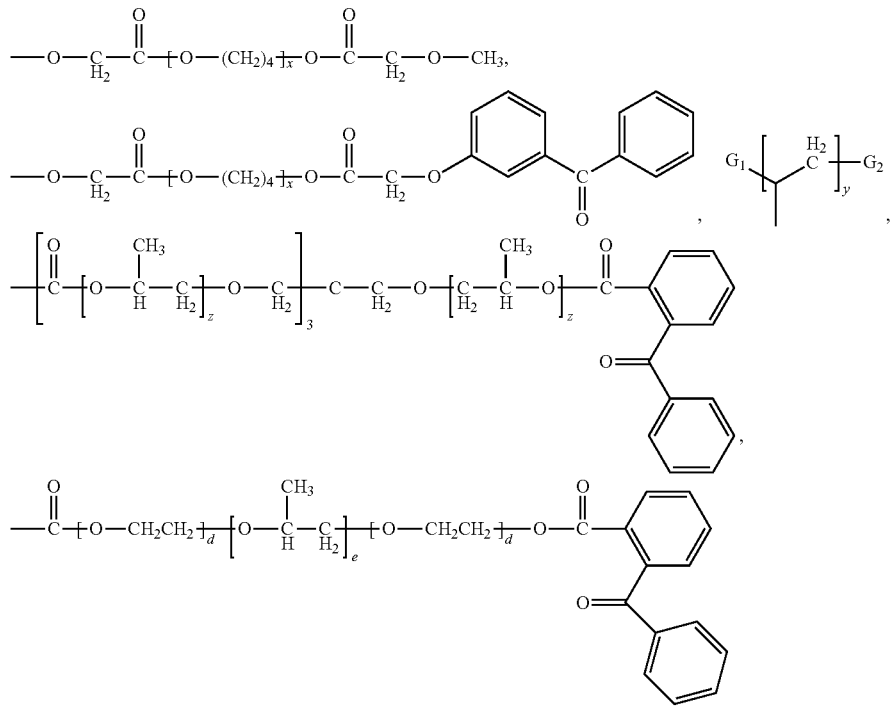

x is 1-10, in particular 1-5;
y is 2-20;
z is 1-6, in particular 1-2;
the sum of d and e is from 10-16, in particular from 12-14, where d is greater than e; and
R$_{56}$ is C$_1$-C$_{12}$alkyl; and
R$_{57}$ is C$_1$-C$_{12}$alkyl which is unsubstituted or is substituted by one or more OH,

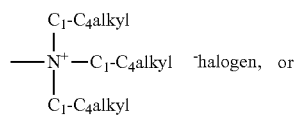

-continued

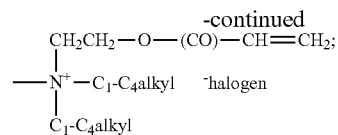

or R$_{57}$ is C$_1$-C$_{12}$alkyl which is interrupted by 1-6 O and which is unsubstituted or substituted by

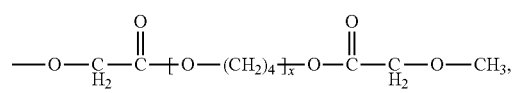

Preferred are compounds of the formula (BP), wherein
R$_{50}$ is hydrogen, C$_1$-C$_{12}$-alkyl, C$_1$-C$_4$-halogenalkyl, halogen, N(C$_1$-C$_4$-alkyl)$_2$, phenyl, (CO)OR$_{56}$, OR$_{57}$,

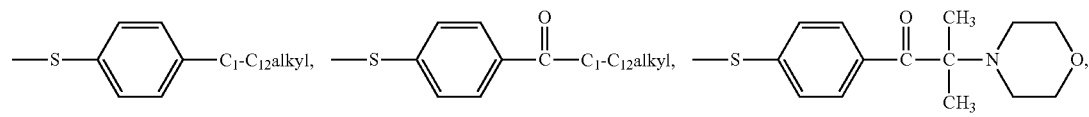

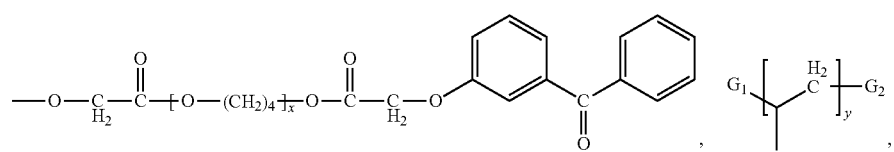

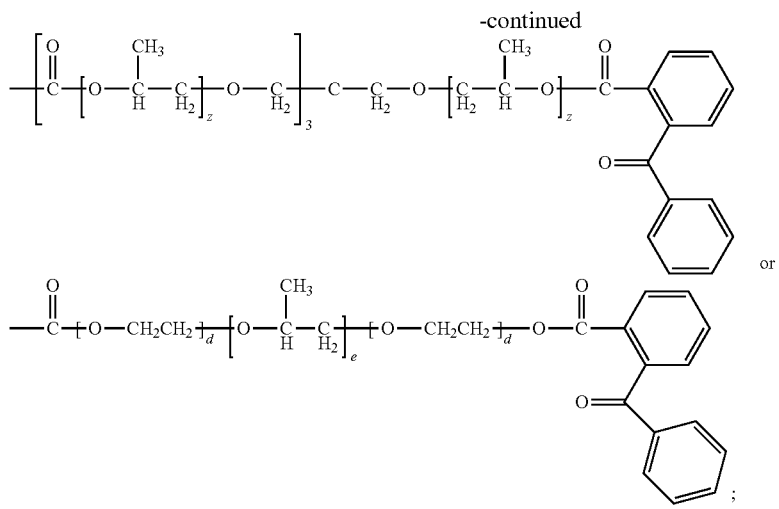

or $R_{51}$ and $R_{52}$ independently of one another are hydrogen, $C_1$-$C_{12}$-alkyl, or phenyl;

$R_{53}$, $R_{54}$ and $R_{55}$ independently of one another are hydrogen or $C_1$-$C_{12}$-alkyl;

x is 1-10, in particular 1-5;

y is 2-20;

z is 1-6, in particular 1-2;

the sum of d and e is from 10-16, in particular from 12-14, where d is greater than e; and $R_{56}$ is $C_1$-$C_{12}$alkyl; and $R_{57}$ is $C_1$-$C_{12}$alkyl.

Specific examples are:

benzophenone, 2,4,6-trimethylbenzophenone, 4-methylbenzophenone, 3-methylbenzo-phenone, 2-methylbenzophenone, 4-chlorobenzophenone, [4-(4-methylthio)phenyl]-phenyl-methanone, 3,3'-dimethyl-4-methoxy benzophenone, methyl-2-methylbenzoate, 4-phenyl-benzophenone, 4,4'-bis(dimethylamino)-benzophenone, a mixture of

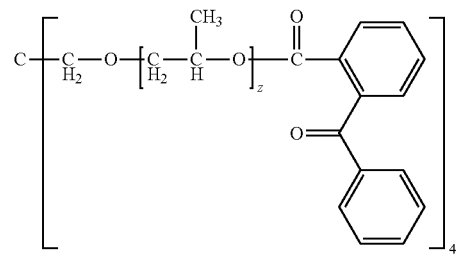

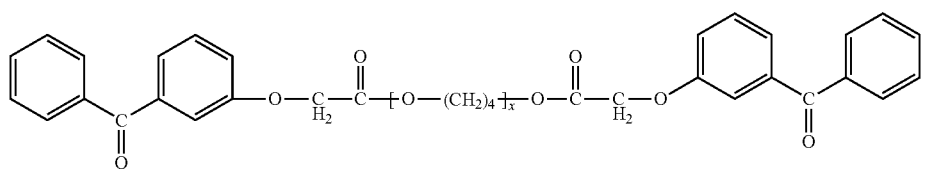

with x=1-20 (Omnipol BP);

with z=about 2 and

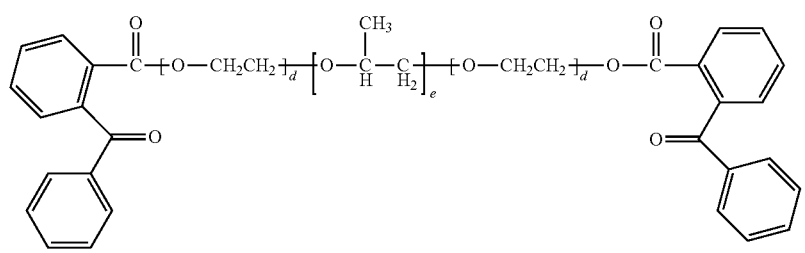

with the sum of d and e is about 14, where d is greater than e (Speedcure 7005, provided by Lambson),

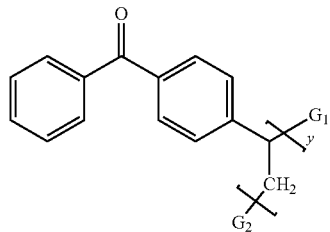

with y=about 14 (Speedcure 7006, provided by Lambson);

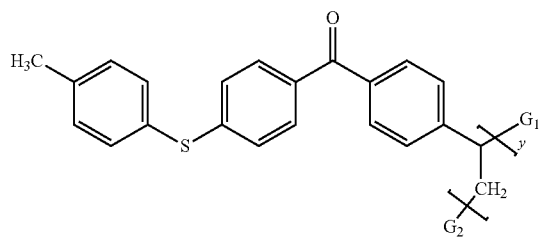

with y=about 12 (Speedcure 7003, provided by Lambson);

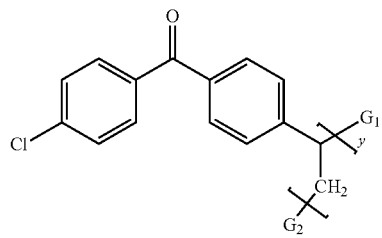

with y=about 13 (Speedcure 7020, provided by Lambson) and any blends or admixtures of the above mentioned compounds.

Compounds of the formula (BP) are well known in the art and the compounds as well as their preparation is for example described in WO 03/033452.

Many of the compounds also are commercially available, for example under the trademark DAROCUR® provided by Ciba Inc., ESACURE®, provided by Lamberti SPA, Speedcure, provided by Lambson or Omnipol provided by IGM.

The thioxanthone compound in the photoinitiator mixture as described above for example is of the formula (TX),

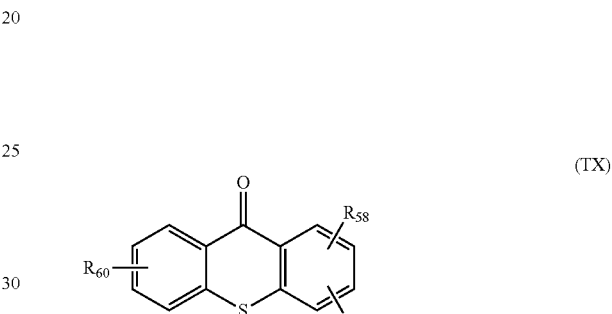

(TX)

wherein $R_{58}$, $R_{59}$ and $R_{60}$ independently of one another are hydrogen, halogen, $C_1$-$C_{12}$alkoxy,

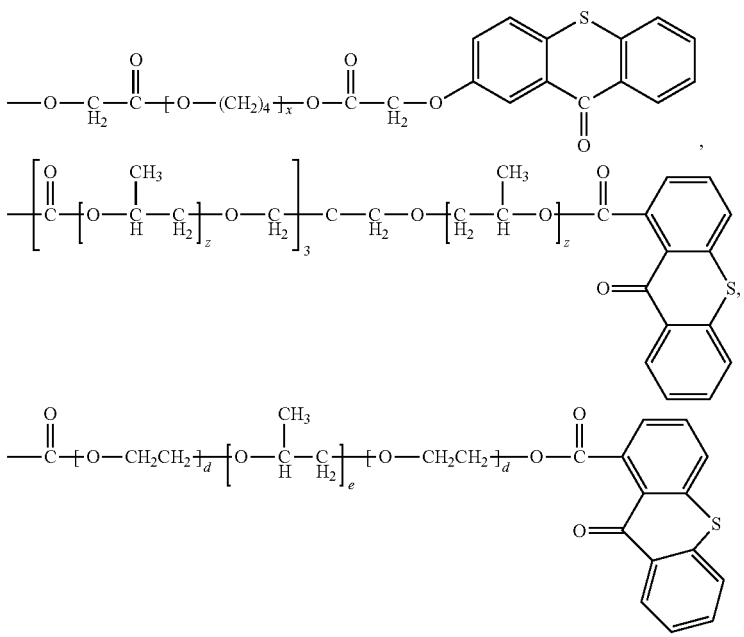

or $C_1$-$C_{12}$alkyl which is unsubstituted or is substituted by one or more OH,

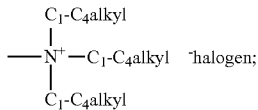

x is 2-10;
y is 2-20;
z is 1-6, in particular 1-2; and
the sum of d and e is from 10-16, in particular from 12-14, where d is greater than e.

Preferred are compounds of the formula (TX), wherein
$R_{60}$ is hydrogen; and
$R_{58}$ and $R_{59}$ are hydrogen, halogen, $C_1$-$C_8$alkyl or $C_1$-$C_8$alkoxy.
Specific examples are
a blend of 2-isopropylthioxanthone and 3-isopropylthioxanthone,
a blend of 2-chlorothioxanthone and 3-chlorothioxanthone,
2,4-dimethylthioxanthone,
2,4-diethylthioxanthone,
1-chloro-4-propoxy-thioxanthone.

Compounds of the formula (TX) are known in the art and the compounds as well as their preparation is for example described in WO 03/033492. Many of the compounds also are commercially available for example under the trademark Omnipol from IGM.

The ketosulfone compound in the photoinitiator mixture as described above for example is of the formula (KS),

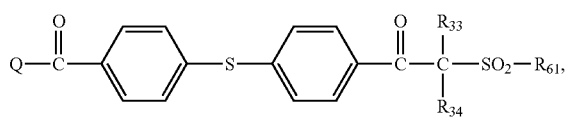 (KS)

wherein
$R_{61}$ is $C_1$-$C_{12}$alkyl, phenyl, naphthyl, wherein the phenyl and naphthyl are unsubstituted or are substituted by one or more $C_1$-$C_{12}$alkyl, halogen, $C_1$-$C_{12}$halogenoalkyl,
Q is

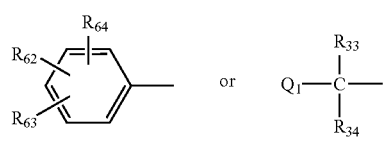

$Q_1$ is OH or $NR_{65}R_{66}$;
$R_{62}$, $R_{63}$ and $R_{64}$ independently of one another are hydrogen, halogen, $C_1$-$C_{12}$alkyl, CN, $C_1$-$C_{12}$alkoxy, phenyl, $SR_{67}$ or $NR_{65}R_{66}$;

$R_{33}$ and $R_{34}$ independently of one another are hydrogen, $C_1$-$C_6$-alkyl, $C_1$-$C_{16}$-alkoxy or —O(CH$_2$CH$_2$O)$_q$—$C_1$-$C_{16}$-alkyl; or unsubstituted phenyl or benzyl; or phenyl or benzyl substituted by $C_1$-$C_{12}$-alkyl; or $R_{33}$ and $R_{34}$ together with the carbon atom to which they are attached form a cyclohexyl ring;
$R_{65}$ and $R_{66}$ independently of each other are hydrogen, $C_1$-$C_{20}$alkyl, $C_1$-$C_{20}$hydroxyalkyl, or $R_{65}$ and $R_{66}$ together with the N-atom to which they are bonded form an aliphatic or aromatic 5- or 6-membered ring, which optionally comprises as further heteroatom an N or O-atom; and
$R_{67}$ is hydrogen, $C_1$-$C_{12}$alkyl or $C_1$-$C_{12}$alkyl substituted by OH.

A specific example is the photoinitiator Esacure 1001 available from Lamberti:
1-[4-(4-benzoylphenylsulfanyl)phenyl]-2-methyl-2-(4-methylphenylsulfonyl)propan-1-one:

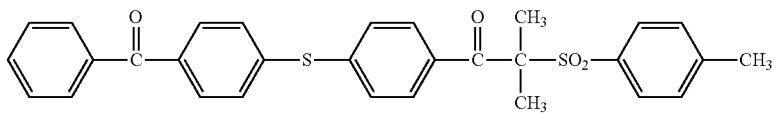

Compounds of the formula (KS) are known in the art and the compounds as well as their preparation are for example described in WO 00/031030. Esacure 1001 M is commercially available.

The benzil ketal or benzoin ether compound in the photoinitiator mixture as described above for example is of the formula (BK)

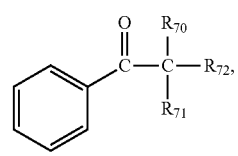 (BK)

wherein
$R_{72}$ is hydrogen or phenyl;
$R_{70}$ and $R_{71}$, when $R_{72}$ is hydrogen, are $C_1$-$C_{12}$alkoxy;
$R_{70}$ and $R_{71}$, when $R_{72}$ is phenyl, independently of one another are hydrogen or $C_1$-$C_{12}$alkoxy.

Preferred are compounds wherein $R_{72}$ is phenyl.
Specific examples are
2-ethoxy-1,2-diphenylethanone, 2-isopropoxy-1,2-diphenylethanone, 2-isobutoxy-1,2-diphenylethanone, 2-butoxy-1,2-diphenylethanone, a blend of benzoin n-butyl and isobutyl ether, 2,2-dimethoxy-1,2-diphenylethanone, 2,2-diethoxy-1,2-diphenylethanone, alpha,alpha-diethoxyacetophenone, alpha,alpha-di-(n-butoxy)-acetophenone.

Compounds of the formula (BK) are known in the art and the compounds as well as their preparation are for example described in U.S. Pat. Nos. 4,318,791, 4,321,118 or 4,308,400. Many of the compounds are commercially available.

The phenylglyoxylate compound in the photoinitiator mixture as described above for example is of the formula (PG)

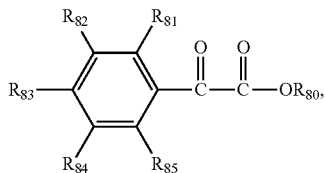
(PG)

wherein
$R_{80}$ is hydrogen, $C_1$-$C_{12}$-alkyl or

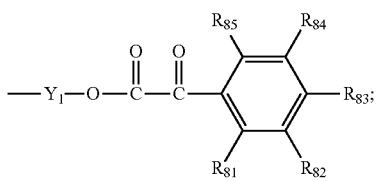

$R_{81}$, $R_{82}$, $R_{83}$, $R_{84}$ and $R_{85}$ independently of one another are hydrogen, unsubstituted $C_1$-$C_{12}$-alkyl or $C_1$-$C_{12}$-alkyl substituted by OH, $C_1$-$C_4$-alkoxy, phenyl, naphthyl, halogen or CN;
wherein the alkyl chain optionally is interrupted by one or more oxygen atoms; or $R_{81}$, $R_{82}$, $R_{83}$, $R_{84}$ and $R_{85}$ independently of one another are $C_1$-$C_4$-alkoxy, $C_1$-$C_4$-alkylthio or $NR_{86}R_{87}$;
$R_{86}$ and $R_{87}$ independently of one another are hydrogen, unsubstituted $C_1$-$C_{12}$-alkyl or $C_1$-$C_{12}$-alkyl substituted by OH or SH wherein the alkyl chain optionally is interrupted by one to four oxygen atoms; or $R_{86}$ and $R_{87}$ independently of one another are $C_2$-$C_{12}$-alkenyl, cyclopentyl, cyclohexyl, benzyl or phenyl; and
$Y_1$ is $C_1$-$C_{12}$-alkylene optionally interrupted by one or more oxygen atoms.
Specific examples are
oxo-phenyl-acetic acid 2-[2-(2-oxo-2-phenyl-acetoxy)-ethoxy]-ethyl ester, methyl alpha-oxo benzeneacetate, ethyl alpha-oxo benzeneacetate.
Compounds of the formula (PG) are known in the art and the compounds as well as their preparation are for example described in WO 06/120212, U.S. Pat. Nos. 6,048,660, 4,475, 999 and 4,038,164. The compounds mentioned as specific examples above are also commercially available.
The borate compound in the photoinitiator mixture as described above for example is of the formula (BT)

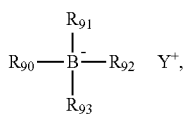
(BT)

wherein
$R_{90}$, $R_{91}$, $R_{92}$ and $R_{93}$ independently of one another are $C_1$-$C_{12}$alkyl, phenyl, naphthyl, anthryl or biphenylyl, wherein the phenyl, naphthyl, anthryl and biphenylyl are unsubstituted or are substituted by one or more halogen, $C_1$-$C_{12}$halogenoalkyl, $C_1$-$C_{12}$alkoxy or $C_1$-$C_{12}$alkyl; and Y is a cation, for example a dye cation, an ammonium, phosphonium or sulfonium cation.
In preferred compounds of the formula (BT) $R_{90}$ is $C_1$-$C_{12}$alkyl;
$R_{91}$, $R_{92}$ and $R_{93}$ are identical and are phenyl which is substituted by halogen, $C_1$-$C_{12}$halogenoalkyl, $C_1$-$C_{12}$alkoxy or $C_1$-$C_{12}$alkyl, especially by halogen or $C_1$-$C_{12}$halogenoalkyl; and
Y is tetraalkylammonium, for example tetrabutylammonium.
Compounds of the formula (BT) are known in the art and the compounds as well as their preparation is for example described in U.S. Pat. Nos. 5,176,984, 5,151,520, 4,954,414 or GB 2307473.
The titanocene compound in the photoinitiator mixture as described above for example is of the formula (TI)

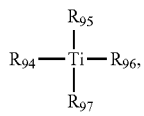

wherein
$R_{94}$ and $R_{95}$ independently of one another are cyclopentadienyl optionally mono-, di-, or tri-substituted by $C_1$-$C_{18}$-alkyl, $C_1$-$C_{18}$-alkoxy, cyclopentyl, cyclohexyl or halogen;
$R_{96}$ and $R_{97}$ are phenyl having at least one F or $CF_3$ substituent in ortho position to the Ti—C bond and having at least a further substituent which is unsubstituted pyrrolinyl or polyoxa-$C_1$-$C_{20}$alkyl or which is pyrrolinyl polyoxa-$C_1$-$C_{20}$alkyl substituted by one or two $C_1$-$C_{12}$-alkyl, di($C_1$-$C_{12}$-alkyl)aminomethyl, morpholinomethyl, $C_2$-$C_4$-alkenyl, methoxymethyl, ethoxymethyl, trimethylsilyl, formyl, methoxy or phenyl; or $R_{96}$ and $R_{97}$ are

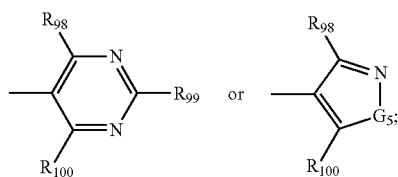

$G_5$ is O, S, or $NR_{101}$;
$R_{98}$, $R_{99}$ and $R_{100}$ independently of one another are hydrogen, halogen, $C_2$-$C_{12}$-alkenyl, $C_1$-$C_{12}$alkoxy, $C_2$-$C_{12}$-alkoxy interrupted by one to four oxygen atoms, cyclohexyloxy, cyclopentyloxy, phenoxy, benzyloxy, unsubstituted phenyl or biphenyl or phenyl or biphenyl substituted by $C_1$-$C_4$-alkoxy, halogen, phenylthio or $C_1$-$C_4$-alkylthio,
with the proviso that $R_{98}$ and $R_{100}$ are not both hydrogen and that with respect to the residue

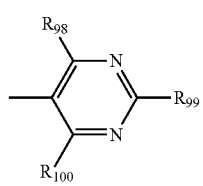

at least one substituent $R_{98}$ or $R_{100}$ is $C_1$-$C_{12}$alkoxy or $C_1$-$C_{12}$alkoxy interrupted by one to four oxygen atoms, cyclohexyloxy, cyclopentyloxy, phenoxy or benzyloxy;
and $R_{101}$ is $C_1$-$C_8$alkyl, phenyl or cyclophenyl.

Specific examples are:

bis(.eta.5-2,4-cyclopentadien-1-yl)bis(2,6-difluoro-3-(1H-pyrrol-1-yl)-phenyl)-titanium and bis(2,6-difluorophenyl)bis[(1,2,3,4,5-eta)-1-methyl-2,4-cyclopentadien-1-yl]-titanium.

Compounds of the formula (TI) are known in the art and the compounds as well as their preparation is for example described in U.S. Pat. Nos. 5,008,302, 5,340,701 and in particular in U.S. Pat. No. 5,075,467.

The compounds specified above are also commercially available under the trademark IRGACURE®, provided by Ciba Inc.

Preferred is a photoinititator mixture as defined above, wherein the component (i) comprises an alpha-hydroxy ketone, monoacylphosphine oxide, bisacylphosphine oxide, ketosulfone or benzil ketal.

Preferred is further a photoinitiator mixture as defined above, wherein the compounds of the formula I or (I')

$R_1$ and $R'_1$ are $C_1$-$C_{12}$alkyl;

$R_2$ and $R_2'$ independently of one another are unsubstituted $C_1$-$C_{20}$alkyl or $C_1$-$C_{20}$alkyl substituted by COOR$_3$ or

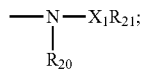

$X_1$ is O;

$R_3$ is $C_1$-$C_{20}$alkyl, $C_1$-$C_8$alkanoyl or phenyl-$C_1$-$C_3$alkyl; or $R_3$ is $C_3$-$C_{20}$cycloalkyl which optionally is interrupted by O;

$R_4$ is $C_1$-$C_{20}$alkyl, $C_1$-$C_8$alkanoyl, phenyl-$C_1$-$C_3$alkyl or $C_1$-$C_{20}$heteroaryl; or $R_4$ is phenyl which is unsubstituted or substituted by $C_1$-$C_{20}$alkyl, halogen or

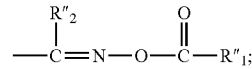

$R_5$ and $R_6$ independently one another are hydrogen, phenyl or $C_1$-$C_{20}$alkyl; or $R_5$ and $R_6$ together with the N-atom to which they are attached form a heteroaromatic ring system, in particular carbazolyl;

$R_7$ is phenyl, naphthyl or $C_1$-$C_{20}$heteroaryl, each of which optionally is substituted by one or more $C_1$-$C_8$alkyl, halogen, CN, OR$_3$, SR$_4$, or NR$_5$R$_6$;

$R_8$ and $R_9$ are hydrogen;

$R_{20}$ is (CO)R$_1$; and $R_{21}$ is (CO)R$_1$.

Interesting are photoinitiator mixtures comprising at least one compound of the formula I or I' and at least one alpha-hydroxy ketone, e.g. of the formula (HK) as defined above; or at least one compound of the formula I or I' and at least one ketosulfone, e.g. of the formula (KS) as defined above; or at least one compound of the formula I of I' and at least one monoacylphosphine oxide, e.g. of the formula (MPO) as defined above; or at least one compound of the formula I or I' and at least one bisacylphosphine oxide, e.g. of the formula (BPO) as defined above.

In the above mixtures preferably as oxime compound compounds of the formula I are used.

Interesting are for example mixtures comprising as component (i) at least on compound of the formula I or I', preferably of the formula I and as component (ii) at least one compound selected from benzophenone, 2,4,6-trimethylbenzophenone, 4-methylbenzophenone, 2,4,6-trimethylbenzoyl-diphenylphosphine oxide, bis(2,4,6-trimethylbenzoyl)phenylphosphine oxide, phenyl-1-hydroxycyclohexyl ketone, 2-hydroxy-2-methyl-1-phenyl-propanone, 2-hydroxy-1-{4-[4-(2-hydroxy-2-methyl-propionyl)-benzyl]-phenyl}-2-methyl-propan-1-one,

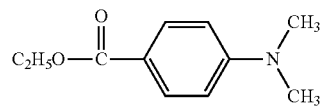

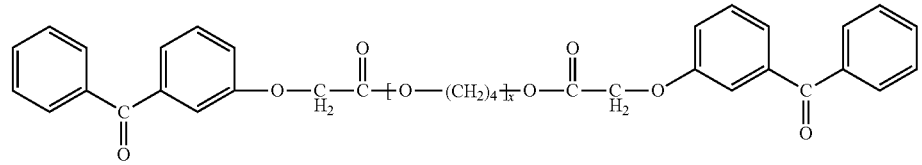

(wherein x=2-20),

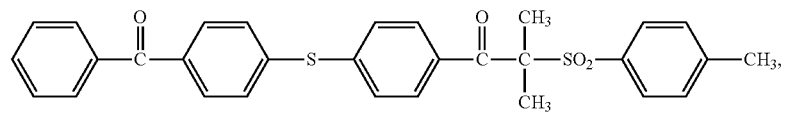

and any combination of said compounds (as component (ii)).

In particular preferred are photoinitiator mixtures comprising (ii) at least one compound of the formula I or I', preferably I, especially a compound wherein $R_1$ and $R_2$ are identical and are methyl and $R_7$ is phenyl substituted by methyl, and (i) bis(2,4,6-trimethylbenzoyl)-phenyl phosphine oxide, 2-hydroxy-1-{4-[4-(2-hydroxy-2-methyl-propionyl)-benzyl]-phenyl}-2-methyl-propan-1-one,

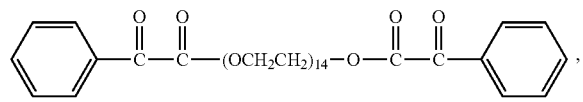,

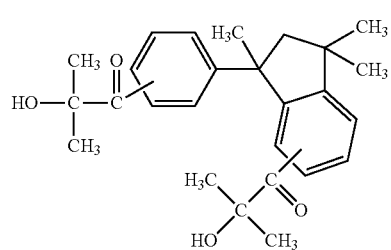

or oligo[2-hydroxy-2-methyl-1[4-(1-methylvinyl)phenyl] propanone].

Further of interest in the context of the present invention are photopolymerizable compositions comprising (a) at least one ethylenically unsaturated photopolymerizable aminoacrylate compound or an ethylenically unsaturated component in the presence of a H-donor (co-initiator) and (b1) a photoinitiator mixture consisting of at least one compound of the formula I or I', preferably I, as defined above and a benzophenone compound, e.g. of the formula (BP) as defined above;

as well as photopolymerizable compositions comprising (a) at least one ethylenically unsaturated photopolymerizable aminoacrylate compound or an ethylenically unsaturated component in the presence of a H-donor (co-initiator) and (b1) a photoinitiator mixture consisting of at least one compound of the formula I or I', preferably I, as defined above and a thioxanthone compound, e.g. of the formula (TX) as defined above.

Preferred are photopolymerizable compositions comprising (a) at least one ethylenically unsaturated photopolymerizable aminoacrylate compound or an ethylenically unsaturated component in the presence of a H-dondor (co-initiator) and (b1) a photoinitiator mixture consisting of at least one compound of the formula I as defined above and Omnipol BP (as defined above), Speedcure 7005 (as defined above).

Substituted aryl radicals phenyl, naphthyl, biphenylyl are substituted 1 to 7, 1 to 6 or 1 to 4 times respectively, in particular one, two or three times. It is evident that a defined aryl radical cannot have more substituents than free positions at the aryl ring.

Substituents on the phenyl ring are preferably in positions 4 or in 3,4-, 3,4,5-, 2,6-, 2,4- or 2,4,6-configuration on the phenyl ring.

Naphthyl is 1-naphthyl or 2-naphthyl.
Coumarinyl is for example 1-coumarinyl:

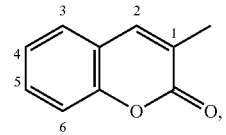

or 4-coumarinyl or 5-coumarinyl.

Phenylene is 1,2-phenylene, 1,3-phenylene or 1,4-phenylene, preferably 1,4-phenylene.

Naphthylene is for example 1,2-, 1,3-, 1,4-, 1,5-, 1,6-, 1,8-, 2,3-, 2,6- or 2,7-naphthlene.

$C_1$-$C_{20}$alkyl is linear or branched and is, for example, $C_1$-$C_{18}$—, $C_1$-$C_{14}$—, $C_1$-$C_{12}$—, $C_1$-$C_8$—, $C_1$-$C_6$— or $C_1$-$C_4$alkyl or $C_4$-$C_{12}$— or $C_4$-$C_8$alkyl. Examples are methyl, ethyl, propyl, isopropyl, n-butyl, sec-butyl, isobutyl, tert-butyl, pentyl, hexyl, heptyl, 2,4,4-trimethylpentyl, 2-ethylhexyl, octyl, nonyl, decyl, dodecyl, tetradecyl, pentadecyl, hexadecyl, octadecyl and icosyl.

$C_1$-$C_{12}$alkyl, $C_2$-$C_{12}$alkyl, $C_1$-$C_{11}$alkyl, $C_1$-$C_8$alkyl and $C_1$-$C_6$alkyl have the same meanings as given above for $C_1$-$C_{20}$alkyl up to the corresponding number of C-atoms.

$C_2$-$C_{20}$alkyl which is interrupted by one or more O is for example interrupted 1-9, 1-5, 1-3 or once or twice by O. Two O-atoms are separated by at least one methylene group, preferably at least two methylene groups, namely ethylene. The alkyl groups are linear or branched. For example the following structural units will occur, —$CH_2$—$CH_2$—O—$CH_2CH_3$, —[$CH_2CH_2O$]$_y$—$CH_3$, wherein y=1-9, —($CH_2$—$CH_2O$)$_7$—$CH_2CH_3$, —$CH_2$—$CH(CH_3)$—O—$CH_2$—$CH_2CH_3$ or —$CH_2$—$CH(CH_3)$—O—$CH_2$—$CH_3$. In case that $C_1$-$C_{20}$alkyl interrupted by one or more O or $NR_{38}$ similar structures, wherein one or more O are replaced by $NR_{38}$ are formed.

$C_1$-$C_{20}$alkylene is linear or branched and is, for example, $C_1$-$C_{16}$—, $C_1$-$C_{12}$—, $C_1$-$C_{10}$—, $C_1$-$C_8$—, $C_1$-$C_6$— or $C_1$-$C_4$alkylene or $C_4$-$C_{12}$— or $C_4$-$C_8$alkylene. Examples are methylene, ethylene, propylene, methylethylene, butylene, methylpropylene, ethylethylene, 1,1-dimethylethylene, 1,2-dimethylethylene, pentylene, hexylene, heptylene, 2-ethylhexylene, octylene, nonylene, decylene, dodecylene, tetradecylene, pentadecylene, hexadecylene, octadecylene and icosylene. $C_1$-$C_{10}$alkylene has the same meanings as given above for $C_1$-$C_{20}$alkylene up to the corresponding number of C-atoms.

Cyclohexylene is 1,2-, 1,3- or 1,4-cyclohexylene.

$C_2$-$C_4$hydroxyalkyl means $C_2$-$C_4$alkyl, which substituted by one or two O-atoms. The alkyl radical is linear or branched. Examples are 2-hydroxyethyl, 1-hydroxyethyl, 1-hydroxypropyl, 2-hydroxypropyl, 3-hydroxypropyl, 1-hydroxybutyl, 4-hydroxybutyl, 2-hydroxybutyl, 3-hydroxybutyl, 2,3-dihydroxypropyl, or 2,4-dihydroxybutyl.

$C_3$-$C_{20}$cycloalkyl in the context of the present application is to be understood as alkyl which at least comprises one ring. It is for example cyclopropyl, cyclobutyl, cyclopentyl, cyclohexyl, cyclooctyl, especially cyclopentyl and cyclohexyl. $C_3$-$C_{20}$cycloalkyl in the context of the present invention is also meant to cover bicyclic rings, in other words a bridged ring, such as for example

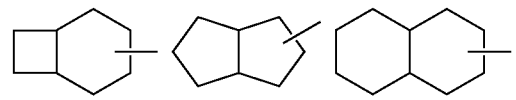

and corresponding rings. Further examples are structures like

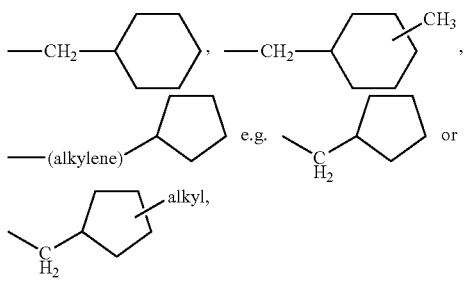

as well as bridged or fused ring systems, e.g.

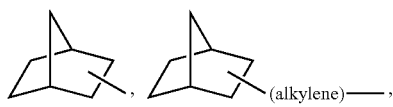

etc. are also meant to be covered by the term.

$C_3$-$C_{20}$cycloalkyl which optionally is interrupted by O, S, CO, NR$_5$; has the meanings given above, wherein at least one CH$_2$-group of the alkyl is exchanged by either O, S, CO or NR$_5$.

Examples are structures like

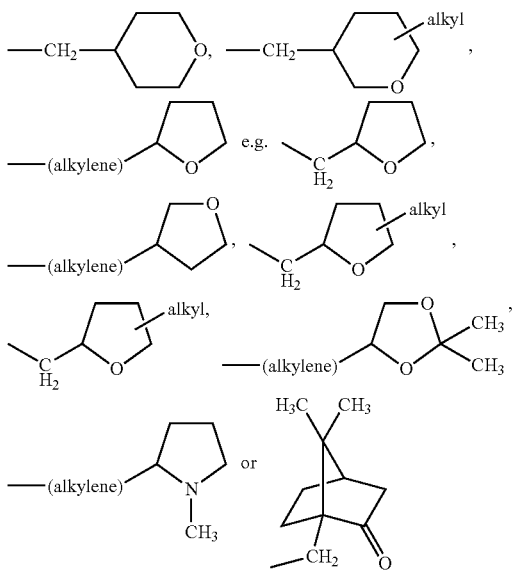

etc.

$C_1$-$C_{18}$alkoxy is $C_1$-$C_{18}$alkyl, which is substituted by one-O-atom. $C_1$-$C_{18}$alkyl has the same meanings as given above for $C_1$-$C_{20}$alkyl up to the corresponding number of C-atoms. $C_1$-$C_4$alkoxy is linear or branched, for example, methoxy, ethoxy, propoxy, isopropoxy, n-butyloxy, sec-butyloxy, isobutyloxy, tert-butyloxy.

$C_1$-$C_{12}$alkylsulfanyl or $C_1$-$C_{12}$alkylthio is $C_1$-$C_{12}$alkyl, which is substituted by one-S-atom. $C_1$-$C_{12}$alkyl has the same meanings as given above for $C_1$-$C_{20}$alkyl up to the corresponding number of C-atoms. $C_1$-$C_4$alkylsulfanyl is linear or branched, for example, methylsulfanyl, ethylsulfanyl, propylsulfanyl, isopropylsulfanyl, n-butylsulfanyl, sec-butylsulfanyl, isobutylsulfanyl, tert-butylsulfanyl.

$C_2$-$C_{10}$alkoxyalkyl is $C_2$-$C_{10}$alkyl, which is interrupted by one O-atom. $C_2$-$C_{10}$alkyl has the same meanings as given above for $C_1$-$C_{20}$alkyl up to the corresponding number of C-atoms. Examples are methoxymethyl, methoxyethyl, methoxypropyl, ethoxymethyl, ethoxyethyl, ethoxypropyl, porpoxymethyl, prpopxyethyl, propoxypropyl.

$C_2$-$C_{20}$alkanoyl is linear or branched and is, for example, $C_2$-$C_{18}$-, $C_2$-$C_{14}$-, $C_2$-$C_{12}$-, $C_2$-$C_8$-, $C_2$-$C_6$— or $C_2$-$C_4$alkanoyl or $C_4$-$C_{12}$— or $C_4$-$C_8$alkanoyl. Examples are acetyl, propionyl, butanoyl, isobutanoyl, pentanoyl, hexanoyl, heptanoyl, octanoyl, nonanoyl, decanoyl, dodecanoyl, tetradecanoyl, pentadecanoyl, hexadecanoyl, octadecanoyl, icosanoyl, preferably acetyl.

$C_1$-$C_8$alkanoyl has the same meanings as given above for $C_2$-$C_{20}$alkanoyl up to the corresponding number of C-atoms.

$C_2$-$C_{12}$alkoxycarbonyl is a linear or branched and is, for example, methoxycarbonyl, ethoxycarbonyl, propoxycarbonyl, n-butyloxycarbonyl, isobutyloxycarbonyl, 1,1-dimethylpropoxycarbonyl, pentyloxycarbonyl, hexyloxycarbonyl, heptyloxycarbonyl, octyloxycarbonyl, nonyloxycarbonyl, decyloxycarbonyl or dodecyloxycarbonyl, especially methoxycarbonyl, ethoxycarbonyl, propoxycarbonyl, n-butyloxycarbonyl or iso-butyloxycarbonyl, preferably methoxycarbonyl.

$C_2$-$C_{12}$alkoxycarbonyl which is interrupted by one or more O is linear or branched. Two O-atoms are separated by at least two methylene groups, namely ethylene.

Phenoxycarbonyl is phenyl-O—CO—. Substituted phenoxycarbonyl radicals are substituted one to four times, for example one, two or three times, especially two or three times. Substituents on the phenyl ring are preferably in positions 4 or in 3,4-, 3,4,5-, 2,6-, 2,4- or 2,4,6-position on the phenyl ring, in particular in 4- or 3,4-position.

Phenyl-$C_1$-$C_3$alkyl is for example benzyl, phenylethyl, α-methylbenzyl or α,α-dimethylbenzyl, especially benzyl.

$C_2$-$C_{12}$alkenyl radicals are mono- or polyunsaturated and are for example $C_2$-$C_{10}$-, $C_2$-$C_8$—, $C_2$-$C_5$-alkenyl e.g. vinyl, allyl, methallyl, 1,1-dimethylallyl, 1-butenyl, 3-butenyl, 2-butenyl, 1,3-pentadienyl, 5-hexenyl, 7-octenyl or dodecenyl, especially allyl. $C_2$-$C_5$alkenyl radicals have the same meanings as given above for $C_2$-$C_{12}$alkenyl radicals up to the corresponding number of C-atoms.

$C_3$-$C_6$alkenoxy radicals may be mono- or polyunsaturated and are for example allyloxy, methallyloxy, butenyloxy, pentenoxy, 1,3-pentadienyloxy, 5-hexenyloxy.

$C_3$-$C_{12}$alkenoyl radicals are mono- or polyunsaturated and are for example $C_3$-$C_{10}$-, $C_3$-$C_8$-alkenoyl, e.g. propenoyl, 2-methyl-propenoyl, butenoyl, pentenoyl, 1,3-pentadienoyl, 5-hexenoyl. $C_3$-$C_6$alkenoyl radicals have the same meanings as given above for $C_3$-$C_{12}$alkenoyl radicals up to the corresponding number of C-atoms.

Halogen is fluorine, chlorine, bromine and iodine, especially fluorine, chlorine and bromine, preferably fluorine and chlorine.

In the context of the present invention $C_1$-$C_{20}$heteroaryl is meant to comprise either one ring or a multiple ring system, e.g. a fused ring-system. Examples are thienyl, benzo[b]thienyl, naphtho[2,3-b]thienyl, thianthrenyl, dibenzofuryl, chromenyl, xanthenyl, thioxanthyl, phenoxathiinyl, pyrrolyl, imidazolyl, pyrazolyl, pyrazinyl, pyrimidinyl, pyridazinyl, indolizinyl, isoindolyl, indolyl, indazolyl, purinyl, quinolizinyl, isoquinolyl, quinolyl, phthalazinyl, naphthyridinyl, quinoxalinyl, quinazolinyl, cinnolinyl, pteridinyl, carbazolyl, 6-carbolinyl, phenanthridinyl, acridinyl, perimidinyl, phenanthrolinyl, phenazinyl, isothiazolyl, phenothiazinyl, isoxazolyl, furazanyl, phenoxazinyl, 7-phenanthryl, anthraquinone-2-yl (=9,10-dioxo-9,10-dihydroanthracen-2-yl), 3-benzo[b]thienyl, 5-benzo[b]thienyl, 2-benzo[b]thienyl, 4-dibenzofuryl, 4,7-dibenzofuryl, 4-methyl-7-dibenzofuryl, 2-xanthenyl, 8-methyl-2-xanthenyl, 3-xanthenyl, 2-phenoxyathiinyl, 2,7-phenoxathiinyl, 2-pyrrolyl, 3-pyrrolyl, 5-methyl-3-pyrrolyl, 2-imidazolyl, 4-imidazolyl, 5-imidazolyl, 2-methyl-4-imidazolyl, 2-ethyl-4-imidazolyl, 2-ethyl-5-imidazolyl, 1H-tetrazol-5-yl, 3-pyrazolyl, 1-methyl-3-pyrazolyl, 1-propyl-4-pyrazolyl, 2-pyrazinyl, 5,6-dimethyl-2-pyrazinyl, 2-indolizinyl, 2-methyl-3-isoindolyl, 2-methyl-1-isoindolyl, 1-methyl-2-indolyl, 1-methyl-3-indolyl, 1,5-dimethyl-2-indolyl, 1-methyl-3-indazolyl, 2,7-dimethyl-8-purinyl, 2-methoxy-7-methyl-8-purinyl, 2-quinolizinyl, 3-isoquinolyl, 6-isoquinolyl, 7-isoquinolyl, 3-methoxy-6-isoquinolyl, 2-quinolyl, 6-quinolyl, 7-quinolyl, 2-methoxy-3-quinolyl, 2-methoxy-6-quinolyl, 6-phthalazinyl, 7-phthalazinyl, 1-methoxy-6-phthalazinyl, 1,4-dimethoxy-6-phthalazinyl, 1,8-naphthyridin-2-yl, 2-quinoxalinyl, 6-quinoxalinyl, 2,3-dimethyl-6-quinoxalinyl, 2,3-dimethoxy-6-quinoxalinyl, 2-quinazolinyl, 7-quinazolinyl, 2-dimethylamino-6-quinazolinyl, 3-cinnolinyl, 6-cinnolinyl, 7-cinnolinyl, 3-methoxy-7-cinnolinyl, 2-pteridinyl, 6-pteridinyl, 7-pteridinyl, 6,7-dimethoxy-2-pteridinyl, 2-carbazolyl, 3-carbazolyl, 9-methyl-2-carbazolyl, 9-methyl-3-carbazolyl, β-carbolin-3-yl, 1-methyl-β-carbolin-3-yl, 1-methyl-β-carbolin-6-yl, 3-phenanthridinyl, 2-acridinyl, 3-acridinyl, 2-perimidinyl, 1-methyl-5-perimidinyl, 5-phenanthrolinyl, 6-phenanthrolinyl, 1-phenazinyl, 2-phenazinyl, 3-isothiazolyl, 4-isothiazolyl, 5-isothiazolyl, 2-phenothiazinyl, 3-phenothiazinyl, 10-methyl-3-phenothiazinyl, 3-isoxazolyl, 4-isoxazolyl, 5-isoxazolyl, 4-methyl-3-furazanyl, 2-phenoxazinyl, 10-methyl-2-phenoxazinyl, etc.

$C_1$-$C_{12}$haloalkyl is $C_1$-$C_{12}$alkyl as defined above substituted by halogen as defined above. The alkyl radical is for example mono- or poly-halogenated, up to the exchange of all H-atoms by halogen. It is for example $C_nH_xHal_y$, wherein x+y=2n+1 and Hal is halogen, preferably F. Specific examples are chloromethyl, trichloromethyl, trifluoromethyl or 2-bromopropyl, especially trifluoromethyl or trichloromethyl.

If the substituents $OR_3$, $SR_4$ and $NR_5R_6$ on a phenyl, naphthyl or biphenylyl ring form 5- or 6-membered rings via the radicals $R_3$, $R_4$, $R_5$ and/or $R_6$ with further substituents on the phenyl or naphthyl ring, or with a carbon atom of the phenyl, naphthyl or biphenylyl ring, structures comprising two or three rings (inclusive the phenyl ring) are obtained. Examples are

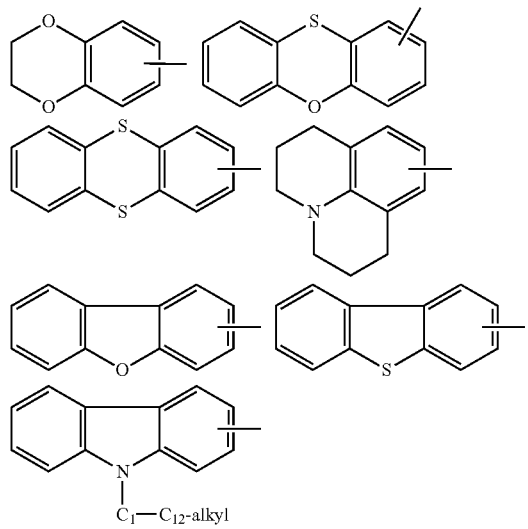

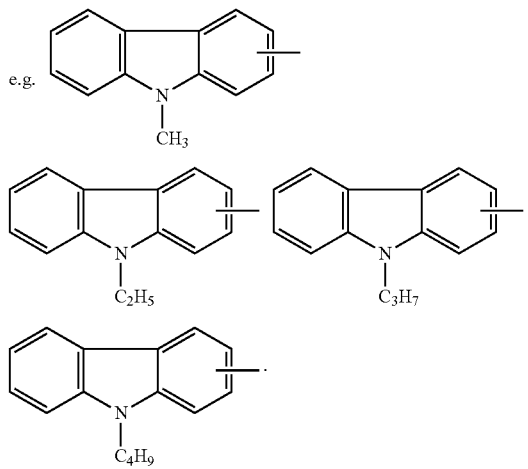

If, for example $R_8$, $R_9$, $R_8'$ and $R_9'$ are $NR_5R_6$, wherein the substituents $NR_5R_6$ form 5- or 6-membered rings via the radicals $R_5$ and/or $R_6$ with one of the carbon atoms of the phenyl, group for example the following structure is formed

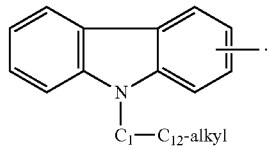

It is clear, that in the context of the present definitions and in view of the examples these groups may bear further substituents.

If the substituents $OR_3$, $SR_4$ or $NR_5R_6$ on the phenyl group as $R_8$ and/or $R_9$ optionally form 5- or 6-membered rings via the radicals $R_3$, $R_4$, $R_5$ and/or $R_6$ with one of the carbon atoms of the phenyl, naphthyl group or that of the substituent $R_7$, for example structures comprising two or three rings (inclusive the phenyl rings) are obtained. Examples are

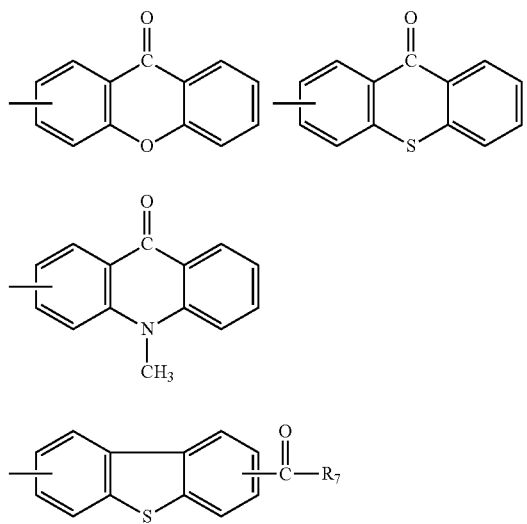

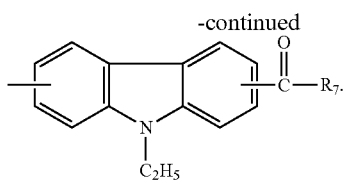

If $R_5$ and $R_6$ together with the N-atom to which they are attached form a heteroaromatic ring system, said ring system is meant to comprise more than one ring, e.g. two or three rings, as well as one or more than one heteroatoms, from the same kind or different ones. Suitable heteroatoms are for example, N, S, O or P, in particular N, S or O. Examples are, carbazole, indole, isoindole, indazole, purine, isoquinoline, quinoline, carboline, phenothiazine etc.

If $R_5$ and $R_6$ or $R_{17}$ and $R_{18}$ together with N-atom to which they are attached form a 5- or 6-membered saturated or unsaturated ring, which optionally is interrupted by O, S or $NR_{14}$, saturated or unsaturated rings are formed, for example aziridine, pyrrole, thiazole, pyrrolidine, oxazole, pyridine, 1,3-diazine, 1,2-diazine, piperidine or morpholine.

If $R_{33}$ and $R_{34}$ together with the carbon atom to which they are attached form a cyclohexyl ring, structures like

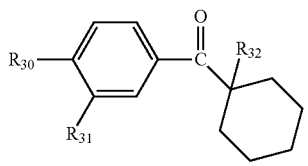

are formed.

$R_{42}$ as a 5- or 6-membered heterocyclic ring comprising an S atom or N atom is for example furyl, thienyl, pyrrolyl, oxinyl, dioxinyl or pyridyl. Said heterocyclic rings are unsubstituted or are for example substituted once or more times by for example linear or branched $C_1$-$C_6$-alkyl such as methyl, ethyl, propyl, butyl, pentyl or hexyl. Examples of such rings are dimethylpyridyl, dimethylpyrrolyl or methylfuryl.

The terms "and/or" or "or/and" in the present context are meant to express that not only one of the defined alternatives (substituents) may be present, but also several of the defined alternatives (substituents) together, namely mixtures of different alternatives (substituents).

The term "at least" is meant to define one or more than one, for example one or two or three, preferably one or two.

The term "optionally substituted" means, that the radical to which it refers is either unsubstituted or substituted.

Throughout this specification and the claims which follow, unless the context requires otherwise, the word "comprise", or variations such as "comprises" or "comprising", will be understood to imply the inclusion of a stated integer or step or group of integers or steps but not the exclusion of any other integer or step or group of integers or steps.

The preferences referring to the compounds of the formula I, I', (HK), (MPO), (BPO), (BP), (TX), (KS), (BK), (PG), (BT) and (TI) as given hereinbefore and in the context of the whole text, are intended not to refer to the compounds as such only, but to all categories of the claims. That is to the compositions, comprising the compounds, as well as the use or process claims in which said compounds are employed.

The unsaturated compounds (a) may include one or more olefinic double bonds. They may be of low (monomeric) or high (oligomeric) molecular mass. Examples of monomers containing a double bond are alkyl, hydroxyalkyl, cycloalkyl (which optionally interrupted by O) or aminoalkyl (meth) acrylates, for example methyl, ethyl, propyl, butyl, hexyl, benzyl, 2-ethylhexyl, isobornyl, cyclohexyl, tetrahydrofurfuryl 2-hydroxyethyl, 2-hydroxypropyl, methoxyethyl, ethoxyethyl, glycerol, phenoxyethyl, methoxydiethylene glycol, ethoxydiethylene glycol, polyethylene glycol, polypropylene glycol, glycidyl, N,N-dimethylaminoethyl, and N, N-diethylaminoethyl (meth)acrylate. Silicone acrylates are also advantageous. Other examples are acrylonitrile, acrylamide, methacrylamide, N-substituted (meth)acrylamides such as N,N-dimethyl (meth)acrylamide, N,N-diethyl (meth)acrylamide, N,N-dibutyl (meth)acrylamide, N-methyl (meth)acrylamide, N-ethyl (meth)acrylamide, N-butyl (meth)-acrylamide, and N-(meth)acryloylmorpholine, vinyl esters such as vinyl acetate, vinyl ethers such as isobutyl vinyl ether, styrene, alkyl- and halostyrenes, N-vinylpyrrolidone, N-vinylcaprolactam, N-vinylacetoamide, N-vinylformamide, vinyl chloride or vinylidene chloride.

Examples of monomers containing two or more double bonds are the diacrylates of ethylene glycol, propylene glycol, neopentyl glycol, hexamethylene glycol or of bisphenol A, and 4,4'-bis(2-acryl-oyloxyethoxy)diphenylpropane, trimethylolpropane triacrylate, pentaerythritol triacrylate or tetraacrylate, vinyl acrylate, divinylbenzene, divinyl succinate, diallyl phthalate, triallyl phosphate, triallyl isocyanurate or tris(2-acryloylethyl) isocyanurate.

Examples of polyunsaturated compounds of relatively high molecular mass (oligomers) are acrylated epoxy resins, polyesters containing acrylate-, vinyl ether- or, depending on the intended application, epoxy-groups, and also polyurethanes and polyethers containing acrylates. Further examples of unsaturated oligomers are unsaturated polyester resins, which are usually prepared from maleic acid, phthalic acid and one or more diols and have molecular weights of from about 500 to 3000. In addition it is also possible to employ vinyl ether monomers and oligomers, and also maleate-terminated oligomers with polyester, polyurethane, polyether, polyvinyl ether and epoxy main chains. Of particular suitability are combinations of oligomers which carry vinyl ether groups and of polymers as described in WO 90/01512. However, copolymers of vinyl ether and maleic acid-functionalized monomers are also suitable. Unsaturated oligomers of this kind can also be referred to as pre-polymers.

Particularly suitable examples are esters of ethylenically unsaturated carboxylic acids and polyols or polyepoxides, and polymers having ethylenically unsaturated groups in the chain or in side groups, for example unsaturated polyesters, polyamides and polyurethanes and copolymers thereof, polymers and copolymers containing (meth)acrylic groups in side chains, and also mixtures of one or more such polymers.

Examples of unsaturated carboxylic acids are acrylic acid, methacrylic acid, crotonic acid, itaconic acid, cinnamic acid, and unsaturated fatty acids such as linolenic acid or oleic acid. Acrylic and methacrylic acid are preferred.

Suitable polyols are aromatic and, in particular, aliphatic and cycloaliphatic polyols. Examples of aromatic polyols are hydroquinone, 4,4'-dihydroxydiphenyl, 2,2-di(4-hydroxyphenyl)-propane, 2,2-bis(4-hydroxyphenyl)methane, 2,2-bis(4-hydroxyphenyl)hexafluoropropane, 9,9-bis(4-hydroxyphenyl)fluorene, novolaks and resols.

Examples of aliphatic and cycloaliphatic polyols are alkylenediols having preferably 2 to 12 C atoms, such as ethylene glycol, 1,2- or 1,3-propanediol, 1,2-, 1,3- or 1,4-butanediol, pentanediol, hexanediol, octanediol, dodecanediol, diethylene glycol, triethylene glcyol, polyethylene glycols having molecular weights of preferably from 200 to 1500, 1,3-cyclopentanediol, 1,2-, 1,3- or 1,4-cyclohexanediol, 1,4-dihydroxymethylcyclohexane, glycerol, tris(β-hydroxyethyl)amine, triethanolamine, trimethylolethane, trimethylolpropane, pentaerythritol, pentaerythritol monooxalate, ethers of pentaerythritol with ethylene glycol or propylene glycol, ethers of dipentaerythritol with ethylene glycol or propylene glycol, dipentaerythritol, 2,2-bis[4-(2-hydroxyethoxy)phenyl]methane, 2,2-bis[4-(2-hydroxyethoxy)phenyl]propane and 9,9-bis[4-(2-hydroxyethoxy)phenyl]fluorine pentaerythritol monooxalate, ethers of pentaerythritol with ethylene glycol or propylene glycol, ethers of dipentaerythritol with ethylene glycol or propylene glycol, pentaerythritol monooxalate, ethers of pentaerythritol with ethylene glycol or propylene glycol, ethers of dipentaerythritol with ethylene glycol or propylene glycol, and sorbitol. Other suitable polyols are polymers and copolymers containing hydroxyl groups in the polymer chain or in side groups, examples being homopolymers or copolymers comprising vinyl alcohol or comprising hydroxyalkyl (meth)acrylates. Further polyols which are suitable are esters and urethanes having hydroxyl end groups.

Other suitable polyols are polymers and copolymers containing hydroxyl groups in the polymer chain or in side groups, examples being polyvinyl alcohol and copolymers thereof or polyhydroxyalkyl methacrylates or copolymers thereof. Further polyols which are suitable are oligoesters having hydroxyl end groups.

The polyols may be partially or completely esterified with one carboxylic acid or with different unsaturated carboxylic acids, and in partial esters the free hydroxyl groups may be modified, for example etherified or esterified with other carboxylic acids.

Examples of polyepoxides are those based on the abovementioned polyols, especially the aromatic polyols, and epichlorohydrin.

Examples of esters based on polyols are: trimethylolpropane tri(meth)acrylate, trimethylolpropane tri(acryloyloxypropyl)ether, trimethylolethane tri(meth)acrylate, ethylene glycol di(meth)acrylate, diethylene glycol di(meth)acrylate, triethylene glycol di(meth)acrylate, tetraethylene glycol di(meth)acrylate, tetramethylene glycol di(meth)acrylate, neopentyl glycol di(meth)acrylate, pentaerythritol di(meth)acrylate, pentaerythritol tri(meth)acrylate, pentaerythritol tetra(meth)acrylate, pentaerythritol tri(meth)acrylate monooxalate, dipentaerythritol di(meth)acrylate, dipentaerythritol tri(meth)acrylate, dipentaerythritol tetra(meth)acrylate, dipentaerythritol penta(meth)acrylate, dipentaerythritol hexa(meth)acrylate, dipentaerythritol penta(meth)acrylate mono(2-hydroxyethyl)ether, tripentaerythritol octa(meth)acrylate, 1,3-butanediol di(meth)acrylate, 1,4-butanediol diitaconate, hexanediol di(meth)acrylate, 1,4-cyclohexanediol di(meth)acrylate, sorbitol tri(meth)acrylate, sorbitol tetra(meth)acrylate, sorbitol penta(meth)acrylate, sorbitol hexa(meth)acrylate, oligoester (meth)acrylates, glycerol di(meth)acrylate and tri(meth)acrylate, di(meth)acrylates of polyethylene glycol with a molecular weight of from 200 to 1500, pentaerythritol diitaconate, dipentaerythritol trisitaconate, dipentaerythritol pentaitaconate, dipentaerythritol hexaitaconate, ethylene glycol diitaconate, propylene glycol diitaconate, 1,3-butanediol diitaconate, 1,4-butanediol diitaconate, tetramethylene glycol diitaconate, sorbitol tetraitaconate, ethylene glycol dicrotonate, tetramethylene glycol dicrotonate, pentaerythritol dicrotonate, ethylene glycol dimaleate, tiethylene glycol dimaleate, pentaerythritol dimaleate, sorbitol tetramaleate, or mixtures thereof.

Typical examples of component (a) based on polyepoxides are 2,2-bis[4-{(2-hydroxy-3-acryl-oxy)propoxy}phenyl]propane, 2,2-bis[4-{(2-hydroxy-3-acryloxy)propoxyethoxy}phenyl]propane, 9,9-bis[4-{(2-hydroxy-3-acryloxy)propoxy}phenyl]fluorene, 9,9-bis[4-{(2-hydroxy-3-acryl-oxy)propoxyethoxy}phenyl]fluorine, and reaction products of epoxy resins based on novolacs with (meth)acrylic acid.

Also suitable as components (a) are the amides of identical or different, unsaturated carboxylic acids with aromatic, cycloaliphatic and aliphatic polyamines having preferably 2 to 6, especially 2 to 4, amino groups. Examples of such polyamines are ethylenediamine, 1,2- or 1,3-propylenediamine, 1,2-, 1,3- or 1,4-butylenediamine, 1,5-pentylenediamine, 1,6-hexylenediamine, octylenediamine, dodecylenediamine, 1,4-diaminocyclohexane, isophoronediamine, phenylenediamine, bisphenylenediamine, di-β-aminoethyl ether, diethylenetriamine, tri-ethylenetetramine, di(β-aminoethoxy)- or di(β-aminopropoxy)ethane. Other suitable polyamines are polymers and copolymers, preferably with additional amino groups in the side chain, and oligoamides having amino end groups. Examples of such unsaturated amides are methylenebisacrylamide, 1,6-hexamethylenebisacrylamide, diethylenetriaminetrismethacrylamide, bis (methacrylamidopropoxy)ethane, β-methacrylamidoethyl methacrylate and N[(β-hydroxyethoxy)ethyl]acrylamide.

In particular in case of the photoinitiator mixture consisting of a compound of the formula I as defined above and a benzophenone compound (BK) or a thioxanthone compound (TX) as defined above, the above mentioned aminoacrylates are preferentially used as component (a). Specific examples are given below in the context of the application in printing inks.

Suitable unsaturated polyesters and polyamides are derived, for example, from maleic acid and from diols or diamines. Some of the maleic acid can be replaced by other dicarboxylic acids. They can be used together with ethylenically unsaturated comonomers, for example styrene. The polyesters and polyamides may also be derived from dicarboxylic acids and from ethylenically unsaturated diols or diamines, especially from those with relatively long chains of, for example 6 to 20 C atoms. Examples of polyurethanes are those composed of saturated or unsaturated diisocyanates and of unsaturated or, respectively, saturated diols.

Polymers with (meth)acrylate groups in the side chain are likewise known. They may, for example, be reaction products of epoxy resins based on novolaks with (meth)acrylic acid, or may be homo- or copolymers of vinyl alcohol or hydroxyalkyl derivatives thereof which are esterified with (meth)acrylic acid, or may be homo- and copolymers of (meth)acrylates which are esterified with hydroxyalkyl (meth)acrylates.

Other suitable polymers with acrylate or methacrylate groups in the side chains are, for example, solvent soluble or alkaline soluble polyimide precursors, for example poly(amic acid ester) compounds, having the photopolymerizable side groups either attached to the back-bone or to the ester groups in the molecule, i.e. according to EP 624826. Such oligomers or polymers can be formulated with the new photoinitiators and optionally reactive diluents, like polyfunctional (meth)acrylates in order to prepare highly sensitive polyimide precursor resists.

The photopolymerizable compounds can be used alone or in any desired mixtures. It is preferred to use mixtures of polyol (meth)acrylates.

Examples of the component (a) are also polymers or oligomers having at least two ethylenically unsaturated groups and at least one carboxyl function within the molecule structure, such as a resin obtained by the reaction of a saturated or unsaturated polybasic acid anhydride with a product of the reaction of an epoxy compound and an unsaturated monocarboxylic acid, for example, photosensitive compounds as described in JP 6-1638 and JP 10301276 and commercial products such as EB9696, UCB Chemicals; KAYARAD TCR1025, Nippon Kayaku Co., LTD. Examples of the polybasic acid anhydride are maleic anhydride, succinic anhydride, itaconic anhydride, phthalic anhydride, tetrahydrophthalic anhydride, hexahydrophthalic anhydride, methyltetrahydrophathalic anhydride, glutaric anhydride, glutaconic anhydride, citraconic anhydride, diglycolic anhydride, iminodiacetic anhydride, 1,1-cyclopentanediacetic anhydride, 3,3-dimethylglutaric anhydride, 3-ethyl-3-methylglutaric anhydride, 2-phenylglutaric anhydride, homophthalic anhydride, trimellitic anhydride, chlorendic anhydride, pyromellitic dianhydride, benzophenone tetracarboxylic acid dianhydride, biphenyl tetracarboxylic acid dianhydride, and biphenylether tetracarboxylic acid dianhydride. Other example of the polymers or oligomers having at least two ethylenically unsaturated groups and at least one carboxyl function within the molecule structure is an addition product formed between a carboxyl group-containing resin and an unsaturated compound having an α,β-unsaturated double bond and an epoxy group. As the carboxylic acid containing polymer, the binder polymers which are resulting from the reaction of an unsaturated carboxylic acid compound with one or more polymerizable compounds, for example, copolymers of (meth)acrylic acid, benzyl (meth)acrylate, styrene and 2-hydroxyethyl (meth)acrylate, copolymers of (meth)acrylic acid, styrene and α-methystyrene, copolymers of (meth)acrylic acid, N-phenylmaleimide, styrene and benzyl (meth)acrylate, copolymers of (meth)acrylic acid and styrene, copolymers of (meth)acrylic acid and benzyl (meth)acrylate, copolymers of tetrahydrofurfuryl (meth)acrylate, styrene and (meth)acrylic acid, and the like.

Examples of the unsaturated compounds having an epoxy group are given below in the formula (V-1)-(V-15);

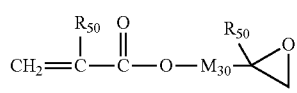
(V-1)

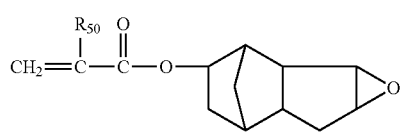
(V-2)

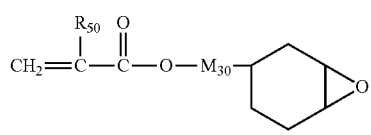
(V-3)

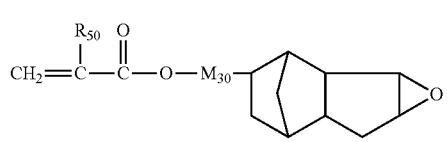
(V-4)

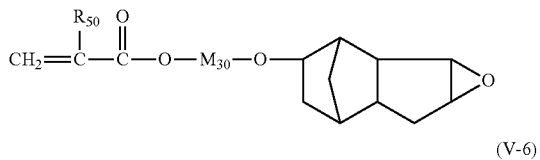
(V-5)

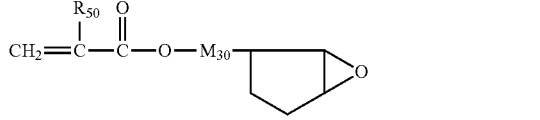
(V-6)

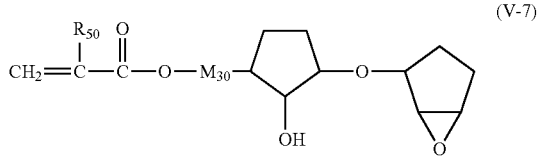
(V-7)

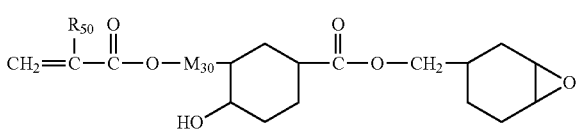
(V-8)

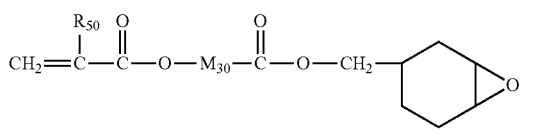
(V-9)

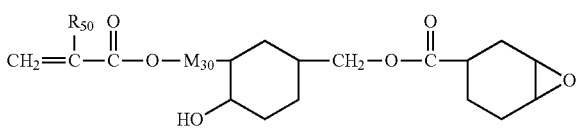
(V-10)

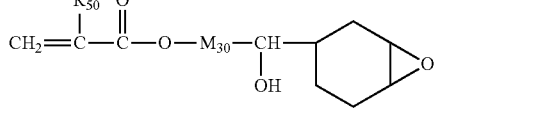
(V-11)

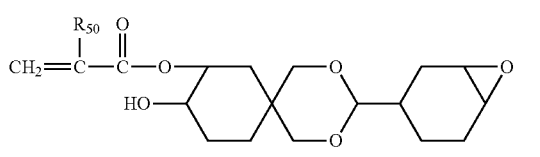
(V-12)

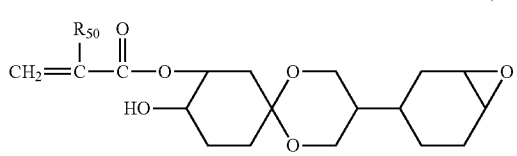
(V-13)

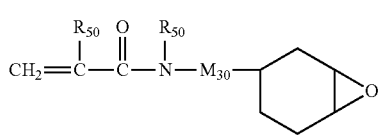
(V-14)

-continued

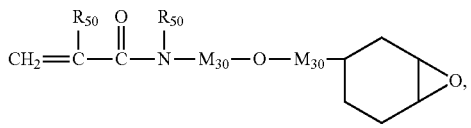
(V-15)

wherein $R_{50}$ is hydrogen or methyl group, $M_{30}$ is substituted or unsubstituted alkylene having 1 to 10 carbon atoms.

Among these compounds, compounds having alicyclic epoxy groups are particularly preferred, because these compounds have a high reactivity with carboxyl group-containing resins, accordingly the reaction time can be shortened. These compounds further do not cause gelation in the process of reaction and make it possible to carry out the reaction stably. On the other hand, glycidyl acrylate and glycidyl methacrylate are advantageous from the viewpoint of sensitivity and heat resistance because they have a low molecular weight and can give a high conversion of esterification.

Concrete examples of the abovementioned compounds are, for example a reaction product of a copolymer of styrene, α-methyl styrene and acrylic acid or a copolymer of methyl methacrylate and acrylic acid with 3,4-epoxycyclohexylmethyl (meth)acrylate and as a commercial product ACA200M, Daicel Industries.

As diluent, a mono- or multi-functional ethylenically unsaturated compound, or mixtures of several of said compounds, can be included in the above composition up to 90%, for example up to 70% by weight based on the solid portion of the composition.

Subject of the invention also is a photopolymerizable composition as described above, wherein the component (a) is a resin obtained by the reaction of a saturated or unsaturated polybasic acid anhydride with a product of the reaction of an epoxy resin and an unsaturated monocarboxylic acid.

Such components are for example described in JP06-1938, JP08-278629, JP08-278630, JP10-301276, JP2001-40022, JP10-221843, JP11-231523, JP2002-206014-A or JP2006-53569-A, the disclosure of which hereby is incorporated by reference.

The unsaturated compounds (a) can also be used as a mixture with cationic photopolymerizable or non-photopolymerizable, film-forming components. These may, for example, be physically drying polymers or solutions thereof in organic solvents, for instance nitrocellulose or cellulose acetobutyrate. They may also, however, be chemically and/or thermally curable (heat-curable) resins, examples being polyisocyanates, polyepoxides and melamine resins, as well as polyimide precursors. The use of heat-curable resins at the same time is important for use in systems known as hybrid systems, which in a first stage are photopolymerized and in a second stage are crosslinked by means of thermal aftertreatment or vice versa. The resin can bear both the photopolymerizable and the heat-curable groups.

The invention also provides compositions comprising as component (a) at least one ethylenically unsaturated photopolymerizable compound which is emulsified or dissolved in water. Many variants of such radiation-curable aqueous prepolymer dispersions are commercially available. A prepolymer dispersion is understood as being a dispersion of water and at least one prepolymer dispersed therein. The concentration of water in these systems is, for example, from 5 to 80% by weight, in particular from 30 to 60% by weight. The concentration of the radiation-curable prepolymer or prepolymer mixture is, for example, from 95 to 20% by weight, in particular from 70 to 40% by weight. In these compositions the sum of the percentages given for water and prepolymer is in each case 100, with auxiliaries and additives being added in varying quantities depending on the intended use.

The radiation-curable, film-forming prepolymers which are dispersed in water and are often also dissolved are aqueous prepolymer dispersions of mono- or polyfunctional, ethylenically unsaturated prepolymers which are known per se, can be initiated by free radicals and have for example a content of from 0.01 to 1.0 mol of polymerizable double bonds per 100 g of prepolymer and an average molecular weight of, for example, at least 400, in particular from 500 to 10,000. Prepolymers with higher molecular weights, however, may also be considered depending on the intended application. Use is made, for example, of polyesters containing polymerizable C—C double bonds and having an acid number of not more than 10, of polyethers containing polymerizable C—C double bonds, of hydroxyl-containing reaction products of a polyepoxide, containing at least two epoxide groups per molecule, with at least one α,β-ethylenically unsaturated carboxylic acid, of polyurethane (meth) acrylates and of acrylic copolymers which contain α,β-ethylenically unsaturated acrylic radicals, as are described in EP 12339. Mixtures of these prepolymers can likewise be used. Also suitable are the polymerizable prepolymers described in EP 33896, which are thioether adducts of polymerizable prepolymers having an average molecular weight of at least 600, a carboxyl group content of from 0.2 to 15% and a content of from 0.01 to 0.8 mol of polymerizable C—C double bonds per 100 g of prepolymer. Other suitable aqueous dispersions, based on specific alkyl (meth)acrylate polymers, are described in EP 41125, and suitable waterdispersible, radiation-curable prepolymers of urethane acrylates can be found in DE 2936039.

Further additives which may be included in these radiation-curable aqueous prepolymer dispersions are dispersion auxiliaries, emulsifiers, antioxidants, e.g. 2,2-thiobis(4-methyl-6t-butylphenol) or 2,6-di-t-butylphenol, light stabilizers, dyes, pigments, fillers, such as glass or alumina, for example talc, gypsum, silicic acid, rutile, carbon black, zinc oxide, iron oxides, reaction accelerators, levelling agents, lubricants, wetting agents, thickeners, flatting agents, antifoams and other auxiliaries customary in paint technology. Suitable dispersion auxiliaries are water-soluble organic compounds which are of high molecular mass and contain polar groups, examples being polyvinyl alcohols, polyvinylpyrrolidone or cellulose ethers. Emulsifiers which can be used are nonionic emulsifiers and, if desired, ionic emulsifiers as well.

In certain cases it may be of advantage to use mixtures of two or more of the photoinitiators of formula (I) or (I'), preferably (I), in combination with the photoinitiators of formula (HK), (MPO), (BPO), (BP), (TX), (KS), (BK), (PG), (BT), (TI); or to use mixtures of two or more of the photoinitiators of formula (HK), (MPO), (BPO), (BP), (TX), (KS), (BK), (PG), (BT), (TI) in combination with the photoinitiator of formula (I) or (I'), preferably (I); or to use mixtures of two or more of the photoinitiators of formula (I) or (I'), preferably (I), in combination with two or more of the photoinitiators of formula (HK), (MPO), (BPO), (BP), (TX), (KS), (BK), (PG), (BT), (TI) in the photopolymerizable composition.

It is of course also possible to add other known photoinitiators (c) of the alpha-amino ketones, e.g. (4-methylthiobenzoyl)-1-methyl-1-morpholinoethane (IRGACURE® 907), (4-morpholinobenzoyl)-1-benzyl-1-dimethylaminopropane (IRGACURE® 369), (4-morpholino-benzoyl)-1-(4-methylbenzyl)-1-dimethylaminopropane (IRGACURE® 379), (4-

(2-hydroxyethyl)aminobenzoyl)-1-benzyl-1-dimethylaminopropane), (3,4-dimethoxybenzoyl)-1-benzyl-1-dimethylaminopropane.

Where the novel photoinitiator systems are employed in hybrid systems, use is made, in addition to the novel free-radical hardeners, of cationic photoinitiators, of peroxide compounds, such as benzoyl peroxide (other suitable peroxides are described in U.S. Pat. No. 4,950,581 column 19, lines 17-25), of aromatic sulfonium-, phosphonium- or iodonium salts as described for example in U.S. Pat. No. 4,950,581, column 18, line 60 to column 19, line 10 or cyclopentadienylarene-iron(II) complex salts, for example ($\eta^6$-iso-propylbenzene)($\eta^5$-cyclopentadienyl)iron(II) hexafluorophosphate, as well as oxime sulfonic acid esters, as are, for example described in EP780729. Also pyridinium and (iso)quinolinium salts as described e.g. in EP497531 and EP 441232 may be used in combination with the new photoinitiator mixtures.

The new photoinitiator mixtures, either alone or in mixtures with other known photoinitiators and sensitizers, can be used also in the form of a dispersion or emulsion in water or aqueous solutions. In case the photoinitiator mixtures are used in emulsions or dispersions conveniently customary dispersants or emulsifiers are added to prepare a stable emulsion or dispersion. Corresponding suitable additives are known to the person skilled in the art.

The photopolymerizable compositions generally comprise 0.01 to 25% by weight, preferably 0.05 to 15% by weight, in particular 0.05 to 10% by weight of the photoinitiator mixture, based on the solid composition. The amount refers to the sum of all photoinitiators added, if additionally to the photoinitiator mixture comprising compounds of the formula (I) or (I') and (HK), (MPO), (BPO), (BP), (TX), (KS), (BK), (PG), (BT), (TI) further initiators (c) are employed. Accordingly, the amount either refers to the photoinitiator mixture (b) or the photoinitiators (b)+(c).

In addition to the photoinitiator mixture the photopolymerizable composition may include various additives (d).

Subject of the invention therefore also is a photopolymerizable composition as described above, additionally to the photoinitiator (b) comprising at least one further photoinitiator (c), and/or other additives (d).

Examples of these various additives (d) are thermal inhibitors, which are intended to prevent premature polymerization, examples being hydroquinone, hydroquinone derivatives, p-methoxyphenol, R-naphthol or sterically hindered phenols, such as 2,6-di-tert-butyl-p-cresol In order to increase the stability on storage in the dark it is possible, for example, to use copper compounds, such as copper naphthenate, stearate or octoate, phosphorus compounds, for example triphenylphosphine, tributylphosphine, triethyl phosphite, triphenyl phosphite or tribenzyl phosphite, quaternary ammonium compounds, for example tetramethylammonium chloride or trimethylbenzylammonium chloride, or hydroxylamine derivatives, for example N-diethylhydroxylamine. To exclude atmospheric oxygen during the polymerization it is either possible to perform the UV-exposure under inert atmosphere or to add paraffin or similar wax-like substances which, being of inadequate solubility in the polymer, migrate to the surface in the beginning of polymerization and form a transparent surface layer which prevents the ingress of air. It is also possible to apply an oxygen-impermeable layer on top of the coating, for example poly(vinylalcohol-co-vinylacetate). Light stabilizers which can be added in a small quantity are UV absorbers, for example those of the hydroxyphenylbenzotriazole, hydroxyphenyl-benzophenone, oxalamide or hydroxyphenyl-s-triazine type. These compounds can be used individually or in mixtures, with or without sterically hindered amines (HALS).

Examples of such UV absorbers and light stabilisers are disclosed in WO 04/074328, page 12, line 9 to page 14, line 23, said disclosure hereby is incorporated by reference.

To accelerate the photopolymerization it is possible to add amines as component (d), for example triethanolamine, N-methyldiethanolamine, ethyl-p-dimethylaminobenzoate, 2-(dimethylamino)ethyl benzoate, 2-ethylhexyl-p-dimethylaminobenzoate, octyl-para-N,N-dimethyl-aminobenzoate, N-(2-hydroxyethyl)-N-methyl-para-toluidine or Michler's ketone. The action of the amines can be intensified by the addition of aromatic ketones of the benzophenone type. Examples of amines which can be used as oxygen scavengers are substituted N,N-dialkylanilines, as are described in EP339841. Other accelerators, coinitiators and autoxidizers are thiols, thioethers, disulfides, phosphonium salts, phosphine oxides or phosphines, as described, for example, in EP438123, in GB2180358 and in JP Kokai Hei 6-68309.

It is further possible to add chain transfer agents which are customary in the art to the compositions according to the invention as component (d). Examples are mercaptans, amines and benzothiazol.

Photopolymerization can also be accelerated by adding further photosensitizers or coinitiators (as component (d)) which shift or broaden the spectral sensitivity. These are, in particular, aromatic compounds, for example benzophenone and derivatives thereof, thioxanthone and derivatives thereof, anthraquinone and derivatives thereof, coumarin and phenothiazine and derivatives thereof, and also 3-(aroylmethylene)thiazolines, rhodanine, camphorquinone, but also eosine, rhodamine, erythrosine, xanthene, thioxanthene, acridine, e.g. 9-phenylacridine, 1,7-bis(9-acridinyl)heptane, 1,5-bis(9-acridinyl)pentane, cyanine and merocyanine dyes.

The curing process can be assisted by adding photosensitizers, in particular, in compositions which are pigmented (for example with titanium dioxide), and also by adding a component which under thermal conditions forms free radicals, for example an azo compound such as 2,2'-azobis(4-methoxy-2,4-dimethylvaleronitrile), a triazene, diazo sulfide, pentazadiene or a peroxy compound, for instance a hydroperoxide or peroxycarbonate, for example t-butyl hydroperoxide, as described for example in EP245639.

The compositions according to the invention may comprise as further additive (d) a photoreducable dye, e.g., xanthene-, benzoxanthene-, benzothioxanthene, thiazine-, pyronine-, porphyrine- or acridine dyes, and/or trihalogenmethyl compounds which can be cleaved by irradiation. Similar compositions are for example described in EP445624.

Further additives known in the art may be added as component (d), as for example flow improvers, adhesion promoters, such as vinyltrimethoxysilane, vinyltriethoxysilane vinyltris(2-methoxyethoxy)silane, N-(2-aminoethyl)-3-aminopropylmethyldimethoxysilane, N-(2-aminoethyl)-3-aminopropyltrimethoxysilane, 3-aminopropyltriethoxysilane, 3-glycidoxypropyltrimethoxysilane, 3-glycidoxypropylmethyldimethoxysilane, 2-(3,4-epoxycyclohexyl)ethyltrimethoxysilane, 3-chloropropylmethyldimethoxysilane, 3-chloropropyltrimethoxysilane, 3-methacryloxypropyltrimethoxysilane and 3-mercaptopropyltrimethoxysilane. Surfactants, optical brighteners, pigments, dyes, wetting agents, levelling assistants, dispersants, aggregation preventers, antioxidants or fillers are further examples for additives (d).

In order to cure thick and pigmented coatings it is appropriate to add glass microspheres or pulverized glass fibres, as described for example in U.S. Pat. No. 5,013,768.

Further suitable components (d) are, as already mentioned above, surfactants and dispersants and other components, in particular to support the application of pigments or colorants in the formulation.

It is preferred to apply a surface treatment to the pigments in order to make the pigment easy to disperse and to stabilize the resultant pigment dispersion. The surface treatment reagents are, for example, surfactants, polymeric dispersants, general texture improving agents, pigment derivatives and mixtures thereof. It is especially preferred when the colorant composition according to the invention comprises at least one polymeric dispersant and/or at least pigment derivative.

Suitable surfactants include anionic surfactants such as alkylbenzene- or alkylnahthalene-sulfonates, alkylsulfosuccinates or naphthalene formaldehyde sulfonates; cationic surfactants including, for example, quaternary salts such as benzyl tributyl ammonium chloride; or non-ionic or amphoteric surfactants such as polyoxyethylene surfactants and alkyl- or amidopropyl betaines, respectively.

Illustrative examples of the surfactant include polyoxyethylene alkyl ethers such as polyoxyethylene lauryl ether, polyoxyethylene stearyl ether and polyoxyethylene oleyl ether; polyoxyethylene alkylphenyl ethers such as polyoxyethylene octylphenyl ether and polyoxyethylene nonylphenyl ether; polyethylene glycol diesters such as polyethylene glycol dilaurate and polyethylene glycol distearate; sorbitan fatty acid esters; fatty acid modified polyesters; tertiary amine modified polyurethanes; polyethyleneimines; those available under the trade names of KP (a product of Shin-Etsu Chemical Co., Ltd), Polyflow (a product of KYOEISHA CHEMICAL Co., Ltd), F-Top (a product of Tochem Products Co., Ltd), MEGAFAC (a product of Dainippon Ink & Chemicals, Inc.), Fluorad (a product of Sumitomo 3M Ltd), Asahi Guard and Surflon (products of Asahi Glass Co., Ltd); and the like.

These surfactants may be used alone or in admixture of two or more.

The surfactant is generally used in an amount of 50 parts or less by weight, preferably 0 to 30 parts by weight, based on 100 parts by weight of the colorant composition.

Polymeric dispersants include high molecular weight polymers with pigment affinic groups. Examples are: statistical co-polymers comprised from, for instance, styrene derivatives, (meth)acrylates and (meth)acrylamides, and such statistical co-polymers modified by post modification; block co-polymers and/or comb polymers comprised from, for instance, styrene derivatives, (meth)acrylates and (meth) acrylamides, and such block co-polymers and/or comb polymers modified by post modification; polyethylenimines, which for instance is crafted with polyesters; polyamines, which for instance is crafted with polyesters; and many kinds of (modified) polyurethanes.

Polymeric dispersants may also be employed. Suitable polymeric dispersants are, for example, BYK's DISPERBYK® 101, 115, 130, 140, 160, 161, 162, 163, 164, 166, 168, 169, 170, 171, 180, 182, 2000, 2001, 2009, 2020, 2025, 2050, 2090, 2091, 2095, 2096, 2150, Ciba's Ciba® EFKA® 4008, 4009, 4010, 4015, 4046, 4047, 4050, 4055, 4060, 4080, 4300, 4310, 4330, 4340, 4400, 4401, 4402, 4403, 4406, 4500, 4510, 4520, 4530, 4540, 4550, 4560, Ajinomoto Fine Techno's PB®711, 821, 822, 823, 824, 827, Lubrizol's SOLSPERSE® 1320, 13940, 17000, 20000, 21000, 24000, 26000, 27000, 28000, 31845, 32500, 32550, 32600, 33500, 34750, 36000, 36600, 37500, 39000, 41090, 44000, 53095 and combinations thereof.

It is preferred to use Ciba® EFKA® 4046, 4047, 4060, 4300, 4310, 4330, 4340, DISPERBYK® 161, 162, 163, 164, 165, 166, 168, 169, 170, 2000, 2001, 2020, 2050, 2090, 2091, 2095, 2096, 2105, 2150, PB®711, 821, 822, 823, 824, 827, SOLSPERSE® 24000, 31845, 32500, 32550, 32600, 33500, 34750, 36000, 36600, 37500, 39000, 41090, 44000, 53095 and combinations thereof as dispersant.

Suitable texture improving agents are, for example, fatty acids such as stearic acid or behenic acid, and fatty amines such as laurylamine and stearylamine. In addition, fatty alcohles or ethoxylated fatty alcohles polyols such as aliphatic 1,2-diols or epoxidized soy bean oil, waxes, resin acids and resin acid salts may be used for this purpose.

Suitable pigment derivatives are, for example, copper phthalocyanine derivatives such as Ciba's Ciba® EFKA® 6745, Lubrizol's SOLSPERSE® 5000, 12000, BYK's SYNERGIST 2100 and azo derivatives such as Ciba® EFKA® 6750, SOLSPERSE® 22000 and SYNERGIST 2105.

The above mentioned dispersants and surfactants for pigments are for example employed in compositions of the present invention which are used as resist formulations, in particular in color filter formulations.

Subject of the invention also is a photopolymerizable composition as described above as further additive (d) comprising a dispersant or a mixture of dispersants as well as a photopolymerizable composition as described above as further additive (d) comprising a pigment or a mixture of pigments.

The choice of additive(s) (d) is made depending on the field of application and on properties required for this field. The additives described above are customary in the art and accordingly are added in amounts which are usual in the respective application.

Binders (e) as well can be added to the novel compositions. This is particularly expedient when the photopolymerizable compounds are liquid or viscous substances. The quantity of binder may, for example, be 2-98%, preferably 5-95% and especially 20-90%, by weight relative to the overall solids content. The choice of binder is made depending on the field of application and on properties required for this field, such as the capacity for development in aqueous and organic solvent systems, adhesion to substrates and sensitivity to oxygen.

Examples of suitable binders are polymers having a molecular weight of about 2,000 to 2,000,000, preferably 3,000 to 1,000,000.

As the binder, which is alkaline developable, for example, a homopolymer of a polymerizable compound having one or more acid groups and one or more polymerizable unsaturated bonds in the molecule, or a copolymer of two or more kinds thereof, and a copolymer of one or more polymerizable compounds having one or more unsaturated bonds copolymerizable with these compounds and containing no acid group, can be used. Such compounds can be obtained by copolymerizing one or more kinds of a low molecular compound having one or more acid groups and one or more polymerizable unsaturated bonds in the molecule with one or more polymerizable compounds having one or more unsaturated bonds copolymerizable with these compounds and containing no acid group. Examples of acids groups are, a —COOH group, a —SO$_3$H group, a —SO$_2$NHCO— group, a phenolic hydroxy group, a —SO$_2$NH— group, and a —CO—NH—CO— group. Among those, a high molecular compound having a —COOH group is particularly preferred.

Examples of the polymerizable compounds having one or more —COOH groups and one or more polymerizable unsaturated bonds in a molecule are (meth)acrylic acid, 2-carboxyethyl (meth)acrylic acid, 2-carboxypropyl (meth)acrylic acid, crotonic acid, cinnamic acid, mono[2-(meth)acryloyloxyethyl]succinate, mono[2-(meth)acryloyloxyethyl]adipate, mono[2-(meth)acryloyloxyethyl]phthalate, mono[2-(meth) acryloyloxyethyl]hexahydrophthalate, mono[2-(meth)acryloyloxyethyl]maleate, mono[2-(meth)acryloyloxypropyl]succinate, mono[2-(meth)acryloyloxypropyl]adipate, mono[2-(meth)acryloyloxypropyl]phthalate, mono[2-(meth)acryloyloxypropyl]hexahydrophthalate, mono[2-(meth)acryloyloxypropyl]maleate, mono[2-(meth)acryloyloxybutyl]succinate, mono[2-(meth)acryloyloxybutyl]adipate, mono[2-(meth)acryloyloxybutyl]phthalate, mono[2-(meth)acryloyloxybutyl]hexahydrophthalate, mono[2-(meth)acryloyloxybutyl]maleate, 3-(alkylcarbamoyl)acrylic acid, α-chloroacrylic acid, maleic acid, monoesterified maleic acid, fumaric acid, itaconic acid, citraconic acid, mesaconic acid, maleic anhydride, and ω-carboxypolycaprolactone mono(meth)acrylate.

Preferable examples of copolymers are copolymers of methyl (meth)acrylate and (meth)acrylic acid, copolymers of benzyl (meth)acrylate and (meth)acrylic acid, copolymers of methyl (meth)acrylate/, ethyl (meth)acrylate and (meth)acrylic acid, copolymers of benzyl (meth)acrylate, (meth)acrylic acid and styrene, copolymers of benzyl (meth)acrylate, (meth)acrylic acid and 2-hydroxyethyl (meth)acrylate, copolymers of methyl (meth)acrylate/, butyl (meth)acrylate, (meth)acrylic acid and styrene, copolymers of methyl (meth)acrylate, benzyl (meth)acrylate, (metha)crylic acid and hydroxyphenyl (meth)acrylate, copolymers of methyl (meth)acrylate, (meth)acrylic acid and polymethyl (meth)acrylate macromonomer, copolymers of benzyl (meth)acrylate, (meth)acrylic acid and polymethyl (meth)acrylate macromonomer, copolymers of tetrahydrofurfuryl (meth)acrylate, styrene and (meth)acrylic acid, copolymers of methyl (meth)acrylate, (meth)acrylic acid and polystyrene macromonomer, copolymers of benzyl (meth)acrylate, (meth)acrylic acid and polystyrene macromonomer, copolymers of benzyl (meth)acrylate, (meth)acrylic acid, 2-hydroxyethyl (meth)acrylate and polystyrene macromonomer, copolymers of benzyl (meth)acrylate, (meth)acrylic acid, 2-hydroxypropyl (meth)acrylate and polystyrene macromonomer, copolymers of benzyl (meth)acrylate, (meth)acrylic acid, 2-hydroxy-3-phenoxypropyl (meth)acrylate and polymethyl (meth)acrylate macromonomer, copolymers of methyl (meth)acrylate, (meth)acrylic acid, 2-hydroxyethyl (meth)acrylate and polystyrene macromonomer, copolymers of benzyl (metha)crylate, (meth)acrylic acid, 2-hydroxyethyl (meth)acrylate and polymethyl (meth)acrylate macromonomer, copolymers of N-phenylmaleimide, benzyl (meth)acrylate, (meth)acrylic acid and styrene, copolymers of benzyl (meth)acrylate, (meth)acrylic acid, N-phenylmaleimide, mono-[2-(meth)acryloyloxyethyl]succinate and styrene, copolymers of allyl (meth)acrylate, (meth)acrylic acid, N-phenylmaleimide, mono-[2-(meth)acryloyloxyethyl]succinate and styrene, copolymers of benzyl (meth)acrylate, (meth)acrylic acid, N-phenylmaleimide, glycerol mono(meth)acrylate and styrene, copolymers of benzyl (meth)acrylate, ω-carboxypolycaprolactone mono(meth)acrylate, (meth)acrylic acid, N-phenylmaleimide, glycerol mono(meth)acrylate and styrene, and copolymers of benzyl (meth)acrylate, (meth)acrylic acid, N-cyclohexylmaleimide and styrene.

The term "(meth)acrylate" in the context of the present application is meant to refer to the acrylate as well as to the corresponding methacrylate.

Vinylbenzenesulfonic acid and 2-(meth)acrylamide-2-methylpropanesulfonic acid are examples of the polymerizable compounds having one or more —SO$_3$H groups and one or more polymerizable unsaturated bonds.

N-methylsulfonyl (meth)acrylamide, N-ethylsulfonyl (meth)acrylamide, N-phenylsulfonyl (meth)acrylamide, and N-(p-methylphenylsulfonyl) (meth)acrylamide are examples of the polymerizable compounds having one or more —SO$_2$NHCO— groups and one or more polymerizable unsaturated bonds.

Examples of polymerizable compounds having one or more phenolic hydroxy groups and one or more polymerizable unsaturated bonds in a molecule include hydroxyphenyl (meth)-acrylamide, dihydroxyphenyl (meth)acrylamide, hydroxyphenyl-carbonyloxyethyl (meth)acrylate, hydroxyphenyloxyethyl (meth)acrylate, hydroxyphenylthioethyl (meth)acrylate, dihydroxyphenylcarbonyloxyethyl (meth)acrylate, dihydroxyphenyloxyethyl (meth)acrylate, and dihydrooxy-phenylthioethyl (meth)acrylate.

Examples of the polymerizable compound having one or more —SO$_2$NH— groups and one or more polymerizable unsaturated bonds in the molecule include compounds represented by formula (a) or (b):

$$CH_2=CHA_{100}\text{-}Y_{100}\text{-}A_{200}\text{-}SO_2\text{—}NH\text{-}A_3 \quad (a)$$

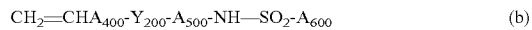

$$CH_2=CHA_{400}\text{-}Y_{200}\text{-}A_{500}\text{-}NH\text{—}SO_2\text{-}A_{600} \quad (b)$$

wherein $Y_{100}$ and $Y_{200}$ each represents —COO—, —CONA$_{700}$-, or a single bond; $A_{100}$ and $A_{400}$ each represents H or CH$_3$; $A_{200}$ and $A_{500}$ each represents $C_1$-$C_{12}$alkylene optionally having a substituent, cycloalkylene, arylene, or aralkylene, or $C_2$-$C_{12}$alkylene into which an ether group and a thioether group are inserted, cycloalkylene, arylene, or aralkylene; $A_{300}$ and $A_{600}$ each represents H, $C_1$-$C_{12}$alkyl optionally having a substituent, a cycloalkyl group, an aryl group, or an aralkyl group; and $A_{700}$ represents H, $C_1$-$C_{12}$alkyl optionally having a substituent, a cycloalkyl group, an aryl group, or an aralkyl group.

The polymerizable compounds having one or more —CO—NH—CO— group and one or more polymerizable unsaturated bond include maleimide and N-acryloyl-acrylamide. These polymerizable compounds become the high molecular compounds comprising a —CO—NH—CO— group, in which a ring is formed together with a primary chain by polymerization. Further, a methacrylic acid derivative and an acrylic acid derivative each having a —CO—NH—CO— group can be used as well. Such methacrylic acid derivatives and the acrylic acid derivatives include, for example, a methacrylamide derivative such as N-acetylmethacrylamide, N-propionylmethacrylamide, N-butanoylmethacrylamide, N-pentanoylmethacrylamide, N-decanoylmethacrylamide, N-dodecanoylmethacrylamide, N-benzoylmethacrylamide, N-(p-methylbenzoyl)methacryl-amide, N-(p-chlorobenzoyl)methacrylamide, N-(naphthyl-carbonyl)-methacrylamide, N-(phenylacetyl)-methacryl-amide, and 4-methacryloylaminophthalimide, and an acrylamide derivative having the same substituent as these. These polymerizable compounds polymerize to be compounds having a —CO—NH—CO— group in a side chain.

Examples of polymerizable compounds having one or more polymerizable unsaturated bond and containing no acid group include a compound having a polymerizable unsaturated bond, selected from esters of (meth)acrylic acid, such as methyl (meth)acrylate, ethyl (meth)acrylate, propyl (meth)acrylate, butyl (meth)acrylate, tetrahydrofurfuryl (meth)acrylate, benzyl (meth)acrylate, 2-ethylhexyl (meth)acrylate, hydroxyethyl (meth)acrylate, hydroxypropyl (meth)acrylate, hydroxybutyl (meth)acrylate, glycerol mono(meth)acrylate, dihydroxypropyl (meth)acrylate, allyl (meth)acrylate, cyclohexyl (meth)acrylate, phenyl (meth)acrylate, methoxyphenyl (meth)acrylate, methoxyethyl (meth)acrylate, phenoxyethyl (meth)acrylate, methoxydiethyleneglycol (meth)acrylate, methoxytriethyleneglycol (meth)acrylate, methoxypropyl (meth)acrylate, methoxydipropyleneglycol (meth)acrylate, isobornyl meth(acrylate), dicyclopentadienyl (meth)acrylate, 2-hydroxy-3-phenoxypropyl (meth)acrylate, tricyclo [5.2.1.0$^{2,6}$]decan-8-yl (meth)acrylate, aminoethyl (meth)acrylate, N,N-dimethylaminoethyl (meth)acrylate, aminopropyl (meth)acrylate, N,N-dimethylaminopropyl (meth)acrylate, glycidyl (meth)acrylate, 2-methylglycidyl (meth)acrylate, 3,4-epoxybutyl (meth)acrylate, 6,7-epoxyheptyl (meth)acrylate; vinyl aromatic compounds, such as styrene, α-methylstyrene, vinyltoluene, p-chlorostyrene, polychlorostyrene, fluorostyrene, bromostyrene, ethoxymethyl styrene, methoxystyrene, 4-methoxy-3-methystyrene, dimethoxystyrene, vinylbenzyl methyl ether, vinylbenzyl glycidyl ether, indene, 1-methylindene; vinyl or allyl esters, such as vinyl acetate, vinyl propionate, vinyl butylate, vinyl pivalate, vinyl benzoate, vinyl trimethylacetate, vinyl diethylacetate, vinyl barate, vinyl caproate, vinyl chloroacetate, vinyl dichloroacetate, vinyl methoxyacetate, vinyl butoxyacetate, vinyl phenylacetate, vinyl acetate, vinyl acetoacetate, vinyl lactate, vinyl phenylbutylate, vinyl cyclohexylcarboxylate, vinyl salicylate, vinyl chlorobenzoate, vinyl tetrachlorobenzoate, vinyl naphthoate, allyl acetate, allyl propionate, allyl butylate, allyl pivalate, allyl benzoate, allyl caproate, allyl stearate, allyl acetoacetate, allyl lactate; vinyl or allyl ethers, such as vinyl methyl ether, vinyl ethyl ether, vinyl hexyl ether, vinyl octyl ether, vinyl ethylhexyl ether, vinyl methoxyethyl ether, vinyl ethoxyethyl ether, vinyl chloroethyl ether, vinyl hydroxyethyl ether, vinyl ethylbutyl ether, vinyl hydroxyethoxyethyl ether, vinyl dimethylaminoethyl ether, vinyl diethylaminoethyl ether, vinyl butylaminoethyl ether, vinyl benzyl ether, vinyl tetrahydrofurfuryl ether, vinyl phenyl ether, vinyl tolyl ether, vinyl chlorophenyl ether, vinyl chloroethyl ether, vinyl dichlorophenyl ether, vinyl naphthyl ether, vinyl anthryl ether, allyl glycidyl ether; amide type unsaturated compounds, such as (meth)acrylamide, N,N-dimethyl (meth)acrylamide, N,N-diethyl (meth)acrylamide, N,N-dibutyl (meth)acrylamide, N,N-diethylhexyl (meth)acrylamide, N,N-dicyclohexyl (meth)acrylamide, N,N-diphenyl (meth)acrylamide, N-methyl-N-phenyl (meth)acrylamide, N-hydroxyethyl-N-methyl (meth)acrylamide, N-methyl (meth)acrylamide, N-ethyl (meth)acrylamide, N-propyl (meth)acrylamide, N-butyl (meth)acrylamide, N-hydroxyethyl (meth)-acrylamide, N-heptyl (meth)acrylamide, N-octyl (meth)acrylamide, N-ethyhexyl (meth)-acrylamide, N-hydroxyethyl (meth)acrylamidecyclohexyl, N-benzyl (meth)acrylamide, N-phenyl (meth)acrylamide, N-tolyl (meth)acrylamide, N-hydroxyphenyl (meth)acrylamide, N-naphthyl (meth)acrylamide, N-phenylsulfonyl (meth)acrylamide, N-methylphenylsulfonyl (meth)acrylamide and N-(meth)acryloylmorpholine, diacetone acrylamide, N-methylol acrylamide, N-butoxyacrylamide; polyolefin type compounds, such as butadiene, isoprene, chloroprene and the like; (meth)acrylonitrile, methyl isopropenyl ketone, maleimide, N-phenylmaleimide, N-methylphenylmaleimide, N-methoxyphenylmaleimide, N-cyclohexyl-maleimide, N-alkylmaleimide, maleic anhydride, polystyrene macromonomer, polymethyl (meth)acrylate macromonomer, polybutyl (meth)acrylate macromonomer; crotonates, such as butyl crotonate, hexyl crotonate, glycerine monocrotonate; and itaconates, such as dimethyl itaconate, diethyl itaconate, dibutyl itaconate; and maleates or fumarates, such as dimethyl mareate, dibutyl fumarate.

There can be used as well hydroxystyrene homo- or co-polymers or a novolak type phenol resin, for example, poly (hydroxystyrene) and poly(hydroxystyrene-co-vinylcyclohexanol), a novolak resin, a cresol novolak resin, and a halogenated phenol novolak resin. More specifically, it includes, for example, the methacrylic acid copolymers, the acrylic acid copolymers, the itaconic acid copolymers, the crotonic acid copolymers, the maleic anhydride copolymers, for example, with styrene as a co-monomer, and maleic acid copolymers, and partially esterified maleic acid copolymers each described in, for example, JP 59-44615-B4 (the term "JP-B4" as used herein refers to an examined Japanese patent publication), JP 54-34327-B4, JP 58-12577-B4, and JP 54-25957-B4, JP 59-53836-A, JP 59-71048-A, JP 60-159743-A, JP 60-258539-A, JP 1-152449-A, JP 2-199403-A, and JP 2-199404-A, and which copolymers can be further reacted with an amine, as e.g disclosed in U.S. Pat. No. 5,650,263; further, a cellulose derivative having a carboxyl group on a side chain can be used, and particularly preferred are copolymers of benzyl (meth)acrylate and (meth)acrylic acid and copolymers of benzyl (meth)acrylate, (meth)acrylic acid and other monomers, for example as described in U.S. Pat. No. 4,139,391, JP 59-44615-B4, JP 60-159743-A and JP 60-258539-A.

Examples of solvent developable binder polymers are poly (alkyl methacrylates), poly(alkyl acrylates), poly(benzylmethacrylate-co-hydroxyethylmethacrylate-co-methacrylic acid), poly(benzylmethacrylate-co-methacrylic acid); cellulose esters and cellulose ethers, such as cellulose acetate, cellulose acetobutyrate, methylcellulose, ethylcellulose; polyvinylbutyral, polyvinylformal, cyclized rubber, polyethers such as polyethylene oxide, polypropylene oxide and polytetrahydrofuran; polystyrene, polycarbonate, polyurethane, chlorinated polyolefins, polyvinyl chloride, vinyl chloride/vinylidene copolymers, copolymers of vinylidene chloride with acrylonitrile, methyl methacrylate and vinyl acetate, polyvinyl acetate, copoly(ethylene/vinyl acetate), polymers such as polycaprolactam and poly(hexamethylene adipamide), and polyesters such as poly(ethylene glycol terephtalate) and poly(hexamethylene glycol succinate) and polyimide binder resins.

The polyimide binder resin in the present invention can either be a solvent soluble polyimide or a polyimide precursor, for example, a poly(amic acid).

Preferred is a photopolymerizable composition, comprising a binder polymer (e), in particular a photopolymerizable composition, comprising as a binder polymer (e) a copolymer of methacrylate and methacrylic acid.

Interesting further are polymeric binder components as described e.g. in JP 10-171119-A, in particular for use in color filters.

The photopolymerizable compositions can be used for various purposes, for example as printing ink, e.g. screen printing inks, inks for offset- or flexo printing, inkjet inks, inks for sheet-fed printing, electrophotography inks, intaglio inks, as a clear finish, as a white or colored finish, for example for wood or metal, as powder coating, as a coating material, inter alia for paper, wood, metal or plastic, as a daylight-curable coating for the marking of buildings and roadmarking, for photographic reproduction techniques, for holographic recording materials, for image recording techniques or to produce printing plates, offset printing plates or flexo printing plates, which can be developed with organic solvents or with aqueous alkalis, for producing masks for screen printing, as dental filling compositions, as adhesives, as pressure-sensitive adhesives, as laminating resins, as etch resists, solder resists, electroplating resists, or permanent resists, both liquid and dry films, as photostructurable dielectric, for printed circuit boards and electronic circuits, as resists to manufacture color filters for a variety of display applications or to generate structures in the manufacturing process of plasma-display panels and electroluminescence displays, (as for example described in U.S. Pat. No. 5,853,446, EP863534, JP 09-244230-A, JP10-62980-A, JP08-171863-A, U.S. Pat. No. 5,840,465, EP855731, JP05-271576-A, JP 05-67405-A) for the production of holographic data storage (HDS) material, for the production of optical switches, optical lattices (interference lattice), light circuits, for producing three-dimensional articles by mass curing (UV curing in transparent moulds) or by the stereolithography technique, as is described, for example, in U.S. Pat. No. 4,575,330, to produce composite materials (for example styrenic polyesters, which may, if desired, contain glass fibres and/or other fibres and other auxiliaries) and other thick-layered compositions, for coating or sealing electronic components and integrated circuits, or as coatings for optical fibres, or for producing optical lenses, e.g. contact lenses or Fresnel lenses. The compositions according to the invention are further suitable for the production of medical equipment, auxiliaries or implants. Further, the compositions according to the invention are suitable for the preparation of gels with thermotropic properties, as for example described in DE19700064 and EP678534.

The novel photoinitiator mixtures may additionally be employed as initiators for emulsion polymerizations, pearl polymerizations or suspension polymerizations, as polymerization initiators for fixing ordered states of liquid-crystalline monomers and oligomers, or as initiators for fixing dyes on organic materials.

In coating materials, use is frequently made of mixtures of a prepolymer with polyunsaturated monomers, which may additionally include a monounsaturated monomer as well. It is the prepolymer here which primarily dictates the properties of the coating film, and by varying it the skilled worker is able to influence the properties of the cured film. The polyunsaturated monomer functions as a crosslinking agent which renders the film insoluble. The mono-unsaturated monomer functions as a reactive diluent, which is used to reduce the viscosity without the need to employ a solvent.

Unsaturated polyester resins are usually used in two-component systems together with a monounsaturated monomer, preferably with styrene. For photoresists, specific one-component systems are often used, for example polymaleimides, polychalcones or polyimides, as described in DE 2308830.

The novel photoinitiator mixtures can also be used for the polymerization of radiation-curable powder coatings. The powder coatings can be based on solid resins and monomers containing reactive double bonds, for example maleates, vinyl ethers, acrylates, acrylamides and mixtures thereof. A free-radically UV-curable powder coating can be formulated by mixing unsaturated polyester resins with solid acrylamides (for example methyl methylacrylamidoglycolate) and a novel free-radical photoinitiator, such formulations being as described, for example, in the paper "Radiation Curing of Powder Coating", Conference Proceedings, Radtech Europe 1993 by M. Wittig and Th. Gohmann. The powder coatings can also contain binders, as are described, for example, in DE 4228514 and in EP 636669.

Free-radically UV-curable powder coatings can also be formulated by mixing unsaturated polyester resins with solid acrylates, methacrylates or vinyl ethers and with a novel photoinitiator (or photoinitiator mixture). The powder coatings may also comprise binders as are described, for example, in DE 4228514 and in EP 636669. The UV-curable powder coatings may additionally comprise white or coloured pigments. For example, preferably rutiletitanium dioxide can be employed in concentrations of up to 50% by weight in order to give a cured powder coating of good hiding power. The procedure normally comprises electrostatic or tribostatic spraying of the powder onto the substrate, for example metal or wood, melting of the powder by heating, and, after a smooth film has formed, radiation-curing of the coating with ultraviolet and/or visible light, using for example medium-pressure mercury lamps, metal halide lamps or xenon lamps. A particular advantage of the radiation-curable powder coatings over their heat-curable counterparts is that the flow time after melting the powder particles can be delayed in order to ensure the formation of a smooth, high-gloss coating. In contrast to heat-curable systems, radiation-curable powder coatings can be formulated to melt at lower temperatures without the unwanted effect of shortening their lifetime. For this reason, they are also suitable as coatings for heat-sensitive substrates, for example wood or plastics. In addition to the novel photoinitiator systems, the powder coating formulations may also include UV absorbers. Appropriate examples are listed above in sections 1.-8.

The novel photocurable compositions are suitable, for example, as coating materials for substrates of all kinds, for example wood, textiles, paper, ceramics, glass, plastics such as for example polyesters, polyethylene terephthalate, polyolefins or cellulose acetate, especially in the form of films, and also metals such as Al, Cu, Ni, Fe, Zn, Mg or Co and GaAs, Si or $SiO_2$ to which it is for example intended to apply a protective layer or a printing ink, or by means of imagewise exposure, to generate an image.

The novel radiation-sensitive compositions further find application as negative resists, having a very high sensitivity to light and being able to be developed in an aqueous alkaline medium without swelling. They are suitable for the production of printing forms for relief printing, planographic printing, photogravure or of screen printing forms, for the production of relief copies, for example for the production of texts in braille, for the production of stamps, for use in chemical milling or as a microresist in the production of integrated circuits. The compositions further may be used as photopatternable dielectric layer or coating, encapsulating material and isolating coating in the production of computer chips, printed boards and other electric or electronic components. The possible layer supports, and the processing conditions of the coating substrates, are just as varied.

The novel composition also relates to a photosensitive thermosetting resin composition and a method of forming a solder resist pattern by the use thereof, and more particularly relates to a novel photosensitive thermosetting resin composition useful as materials for the production of printed circuit boards, the precision fabrication of metallic articles, the etching of glass and stone articles, the relief of plastic articles, and the preparation of printing plates and particularly useful as a solder resist for printed circuit boards and to a method of forming a solder resist pattern by the steps of exposing a layer of the resin composition selectively to an actinic ray through a photomask having a pattern and developing the unexposed part of the layer.

The solder resist is a substance which is used during the soldering of a given part to a printed circuit board for the purpose of preventing molten solder from adhering to irrelevant portions and protecting circuits. It is, therefore, required to possess such properties as high adhesion, insulation resistance, resistance to soldering temperature, resistance to solvents, resistance to alkalis, resistance to acids, and resistance to plating.

Because the photocurable compositions according to the invention have a good thermal stability and are sufficiently resistant to inhibition by oxygen, they are particularly suitable for the production of color filters or color mosaic systems, such as described, for example, in EP320264. Color filters usually are employed in the manufacturing of flat panel displays such as LCD's, PDP (plasma panel display), EL (electroluminessence) display, and projection systems, image sensors, CCD (charge coupled device), and CMOS (complementary metal oxide semiconductor) sensors for scanner, digital camera and video camera.

The color filters usually are prepared by forming red, green and blue pixels and a black matrix on a glass substrate. In these processes photocurable compositions according to the invention can be employed. A particularly preferred method of use comprises adding of the coloring matters, dyes and pigments of red, green and blue colors to the light-sensitive resin composition of the present invention, coating of the substrate with the composition, drying of the coating with a short heat treatment, patternwise exposure of the coating to actinic radiation and subsequent development of the pattern in an aqueous alkaline developer solution and optionally a heat treatment. Thus, by subsequently applying a red, green and blue pigmented coating, in any desired order, on top of each other with this process a color filter layer with red, green and blue color pixels can be produced.

In addition to a process in which the light-sensitive resin composition is coated on a substrate and dried, the light-sensitive resin composition of the present invention can be used as well for a layer transfer material. That is, the light-sensitive resin composition is layer-wise provided directly on a temporary support, preferably on a polyethylene terephthalate film, or on a polyethylene terephthalate film on which an oxygen-shielding layer and a peeling layer or the peeling layer and the oxygen-shielding layer are provided. Usually, a removable cover sheet made of a synthetic resin is laminated thereon for a protection in handling. Further, there can be applied as well a layer structure in which an alkali soluble thermoplastic resin layer and an intermediate layer are provided on a temporary support and further a light-sensitive resin composition layer is provided thereon (JP 5-173320-A).

A metal support, glass, ceramics or a synthetic resin film can for example be used as a support for a color filter. Glass and a synthetic resin film, which is transparent, and have an excellent dimension stability is particularly preferred.

The thickness of the light-sensitive resin composition layer is usually 0.1 to 50 micrometers, in particular 0.5 to 5 micrometers.

The development is carried out by washing out the areas which were not polymerized with a suitable developing solution. This process is repeated to form the image having plural colors.

A diluted aqueous solution of an alkaline substance can be used as a developing solution for the light-sensitive resin composition of the present invention if the composition contains alkali soluble resin or alkali soluble monomers or oligomers, and further a developer solution prepared by adding a small amount of a water-miscible organic solvent thereto is included as well.

Examples of suitable alkaline materials include alkali metal hydroxides (for example, sodium hydroxide and potassium hydroxide), alkali metal carbonates (for example, sodium carbonate and potassium carbonate), alkali metal bicarbonates (for example, sodium bicarbonate and potassium bicarbonate), alkali metal silicates (for example, sodium silicate and potassium silicate), alkali metal metasilicates (for example, sodium metasilicate and potassium metasilicate), triethanolamine, diethanolamine, monoethanolamine, morpholine, tetraalkylammonium hydroxides (for example, tetramethylammonium hydroxide), or trisodium phosphate. The concentration of the alkaline substance is 0.01 to 30 weight %, and pH is preferably 8 to 14.

Suitable organic solvents which are miscible with water include methanol, ethanol, 2-propanol, 1-propanol, butanol, diacetone alcohol, ethylene glycol monomethyl ether, ethylene glycol monoethyl ether, ethylene glycol mono-n-butyl ether, diethyleneglycol dimethyl ether, propyleneglycol monomethyl ether acetate, ethyl-3-ethoxypropionate, methyl-3-methoxypropionate, n-butyl acetate, benzyl alcohol, acetone, methyl ethyl ketone, cyclopentanone, cyclohexanone, 2-heptanone, 2-pentanone, epsilon-caprolactone, gamma-butyrolactone, dimethylformamide, dimethylacetoamide, hexamethylphosphoramide, ethyl lactate, methyl lactate, epsilon-caprolactam, and N-methyl-pyrrolidinone. The concentration of the organic solvent which is miscible with water is 0.1 to 30 weight %.

Further, a publicly known surface active agent can be added. The concentration of the surface active agent is preferably 0.001 to 10 weight %.

The developer solution can be used in all forms known to the person skilled in the art, for example in form of a bath solution, puddle, or a spraying solution. It is possible to put a rinsing step after the development processing.

A final heat treatment is preferably carried out after the development processing. Accordingly, a support having a layer which is photopolymerized by exposing (hereinafter referred to as a photocured layer) is heated in an electric furnace and a drier, or the photocured layer is irradiated with an infrared lamp or heated on a hot plate. The heating temperature and time depend on the composition used and the thickness of the formed layer. In general, heating is preferably applied at about 120° C. to about 250° C., for about 5 to about 60 minutes.

The pigment which can be comprised in the composition according to the present invention, including a pigmented color filter resist composition, is preferably a processed pigment, for example a powdery or pasty product prepared by finely dispersing a pigment into at least one resin selected from the group consisting of acrylic resin, vinyl chloride-vinyl acetate copolymer, maleic acid resin and ethyl cellulose resin.

The red pigment for the color filter resist composition comprises, for example, an anthraquinone type pigment alone, a diketopyrolopyrole type pigment alone, a mixture of them or a mixture consisting of at least one of them and a disazo type yellow pigment, an isoindoline type yellow pigment or a pyrimidine type yellow pigment, in particular C. I. Pigment Red 177 alone, C. I. Pigment Red 254 alone, a mixture of C. I. Pigment Red 177 and C. I. Pigment Red 254 or a mixture consisting of at least one member of C. I. Pigment Red 177 and C. I. Pigment Red 254, and C. I. Pigment Yellow 83, C. I. Pigment Yellow 139, C. I. Pigment Yellow 150 or C. I. Pigment Yellow 215 ("CI" refers to the Color Index, known to the person skilled in the art and publicly available).

Further suitable examples for the pigment are C.I. Pigment Red 9, 97, 105, 122, 123, 144, 149, 168, 176, 179, 180, 185, 202, 207, 209, 214, 220, 221, 222, 242, 244, 255, 264, 272 and a brominated diketopyrolopurole and C.I. Pigment Yellow 12, 13, 14, 17, 20, 24, 31, 53, 55, 93, 95, 109, 110, 128, 129, 138, 139, 150, 153, 154, 155, 166, 168, 185, 199, 213 and C.I. Pigment Orange 43, 71 and 73.

Examples of the dyes for red color are C. I. Solvent Red 25, 27, 30, 35, 49, 83, 89, 100, 122, 138, 149, 150, 160, 179, 218, 230, C. I. Direct Red 20, 37, 39, 44, and C. I. Acid Red 6, 8, 9, 13, 14, 18, 26, 27, 51, 52, 87, 88, 89, 92, 94, 97, 111, 114, 115, 134, 145, 151, 154, 180, 183, 184, 186, 198, C. I. Basic Red 12, 13, C. I. Disperse Red 5, 7, 13, 17 and 58. The Red dyes can be used in combination with yellow and/or orange dyes.

The green pigment for the color filter resist composition comprises for instance a halogenated phthalocyanine type pigment alone or its mixture with a disazo type yellow pigment, an quinophthalone type yellow pigment or a metal complex, in particular C. I. Pigment Green 7 alone, C. I. Pigment Green 36 alone, C. I. Pigment Green 58 alone or a mixture consisting of at least one member of C. I. Pigment Green 7, C. I. Pigment Green 36, C. I. Pigment Green 58 and C. I. Pigment Yellow 83, C. I. Pigment Yellow 138, C. I. Pigment Yellow 150 or C. I. Pigment Yellow 215. Other suitable green pigments are C.I. Pigment Green 15, 25 and 37. Examples for suitable green dyes are C. I. Acid Green 3, 9, 16, C. I. Basic Green 1 and 4.

Examples for suitable blue pigments for the color filter resist composition are phthalocyanine type pigments, used either alone or in combination with an dioxazine type violet pigment, for instance, C. I. Pigment Blue 15:6 alone, a combination of C. I. Pigment Blue 15:6 and C. I. Pigment Violet 23. Further examples for blue pigments are such of C. I. Pigment Blue 15:3, 15:4, 16, 22, 28 and 60 and sub-phthalocyanine type pigments. Other suitable pigments are C. I. Pigment Violet 14, 19, 23, 29, 32, 37, 177 and C. I. Orange 73.

Examples for suitable blue dyes are C. I. Solvent Blue 25, 49, 68, 78, 94, C. I. Direct Blue 25, 86, 90, 108, C. I. Acid Blue 1, 7, 9, 15, 103, 104, 158, 161, C. I. Basic Blue 1, 3, 9, 25, and C. I. Disperse Blue 198.

The pigment of the photopolymeric composition for black matrix preferably comprises at least one member selected from the group consisting of carbon black, titanium black and iron oxide. However, a mixture of other pigments which, in total, give the black appearance, can also be used. For example, also C. I. Pigment Black 1, 7 and 31 can be used alone or in combination.

Other examples of the dyes used for color filter are C. I. Solvent Yellow 2, 5, 14, 15, 16, 19, 21, 33, 56, 62, 77, 83, 93, 162, 104, 105, 114, 129, 130, 162, C. I. Disperse Yellow 3, 4, 7, 31, 54, 61, 201, C. I. Direct Yellow 1, 11, 12, 28, C. I. Acid Yellow 1, 3, 11, 17, 23, 38, 40, 42, 76, 98, C. I. Basic Yellow 1, C. I. Solvent Violet 13, 33, 45, 46, C. I. Disperse Violet 22, 24, 26, 28, C. I. Acid Violet 49, C. I. Basic Violet 2, 7, 10, C. I. Solvent Orange 1, 2, 5, 6, 37, 45, 62, 99, C. I. Acid Orange 1, 7, 8, 10, 20, 24, 28, 33, 56, 74, C. I. Direct Orange 1, C. I. Disperse Orange 5, C. I. Direct Brown 6, 58, 95, 101, 173, C. I. Acid Brown 14, C. I. Solvent Black 3, 5, 7, 27, 28, 29, 35, 45 and 46.

In some special cases of manufacturing color filters, complementary colors, yellow, magenta, cyan and optionally green, are used instead of red, green and blue. As yellow for this type of color filters, the abovementioned yellow pigments and dyes can be employed. Examples of the colorants suitable for magenta color are C. I. Pigment Red 122, 144, 146, 169, 177, C. I. Pigment Violet 19 and 23. Examples of cyan color are aluminum phthalocyanine pigments, titanium phthalocyanine pigments, cobalt phthalocyanine pigments, and tin phthalocyanine pigments.

For any color, combinations of more than two pigments can also be used. Especially suitable in color filter applications are powdery processed pigments prepared by finely dispersing the above mentioned pigments into a resin.

The concentration of the pigment in the total solid component (pigments of various colors and resin) is for example in the range of 5% to 80% by weight, in particular in the range of 20% to 65% by weight.

The pigments in the color filter resist composition have preferably a mean particle diameter smaller than the wavelength of visible light (400 nm to 700 nm). Particularly preferred is a mean pigment diameter of <100 nm.

If necessary, the pigments may be stabilized in the photosensitive composition by pretreatment of the pigments with a dispersant to improve the dispersion stability of the pigment in the liquid formulation. Suitable additives are described above.

Preferably, the color filter resist composition according to the present invention contains additionally at least one addition polymerizable monomeric compound as component (a).

The ethylenically unsaturated compounds (a) in the color filter resist composition include one or more olefinic double bonds. They may be of low (monomeric) or high (oligomeric) molecular mass. Examples of compounds containing a double bond are (meth)acrylic acid, (meth)acrylates, (meth)acrylonitrile, (meth)acrylamide, N-substituted (meth)acrylamides, vinyl esters, vinyl ethers, styrenes and the like.

Examples of polyunsaturated compounds of relatively high molecular mass (oligomers) are polyesters, polyurethanes, polyethers and polyamides, which contain ethylenically unsaturated carboxylates.

Particularly suitable examples are esters of an ethylenically unsaturated carboxylic acid with a polyol or polyepoxide described above.

Examples of esters based on polyols are trimethylolpropane tri(meth)acrylate, trimethylol-propane tri(acryloyloxypropyl)ether, trimethylolethane tri(meth)acrylate, ethylene glycol di-(meth)acrylate, diethylene glycol di(meth)acrylate, triethylene glycol di(meth)acrylate, tetra-ethylene glycol di(meth)acrylate, tetramethylene glycol di(meth)acrylate, neopentyl glycol di(meth)acrylate, pentaerythritol di(meth)acrylate, pentaerythritol tri(meth)acrylate, pentaerythritol tetra(meth)acrylate, pentaerythritol tri(meth)acrylate monooxalate, dipentaerythritol di(meth)acrylate, dipentaerythritol tri(meth)acrylate, dipentaerythritol tetra(meth)acrylate, dipentaerythritol penta(meth)acrylate, dipentaerythritol hexa(meth)acrylate, dipentaerythritol penta(meth)acrylate mono(2-hydroxyethyl)ether, tripentaerythritol octa(meth)acrylate, 1,3-butanediol di(meth)acrylate, 1,4-butanediol diitaconate, hexanediol di(meth)acrylate, 1,4-cyclohexanediol di(meth)acrylate, sorbitol tri(meth)acrylate, sorbitol tetra(meth)acrylate, sorbitol penta(meth)acrylate, sorbitol hexa(meth)acrylate, oligoester (meth)acrylates, glycerol di(meth)acrylate and tri(meth)acrylate, di(meth)acrylates of polyethylene glycol with a molecular weight of from 200 to 1500, pentaerythritol diitaconate, dipentaerythritol trisitaconate, dipentaerythritol pentaitaconate, dipentaerythritol hexaitaconate, ethylene glycol diitaconate, propylene glycol diitaconate, 1,3-butanediol diitaconate, 1,4-butanediol diitaconate, tetramethylene glycol diitaconate, sorbitol tetraitaconate, ethylene glycol dicrotonate, tetramethylene glycol dicrotonate, pentaerythritol dicrotonate, ethylene glycol dimaleate, tiethylene glycol dimaleate, pentaerythritol dimaleate, sorbitol tetramaleate, or mixtures thereof.

Other examples are pentaerythritol and dipentaerythritol derivatives shown in the following formula (XII) and (XIII):

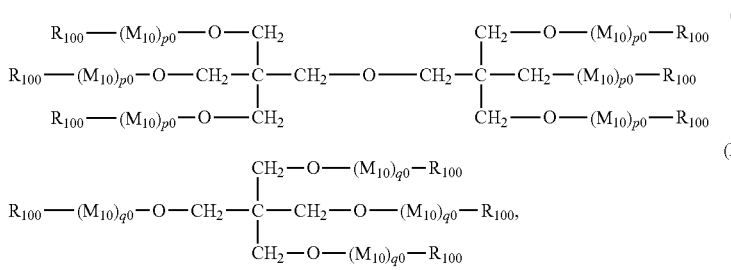

(XII)

(XIII)

wherein
$M_{10}$ is —(CH$_2$CH$_2$O)— or —[CH$_2$CH(CH$_3$)O]—,
$R_{100}$ is —COCH=CH$_2$ or —COC(CH$_3$)=CH$_2$,
p0 is 0 to 6 (total of p0: 3-24), and q0 is 0 to 6 (total of q0: 2-16).

Typical examples of component (a) based on polyepoxides are 2,2-bis[4-{(2-hydroxy-3-acryloxy)propoxy}phenyl]propane, 2,2-bis[4-{(2-hydroxy-3-acryloxy)propoxyethoxy}phenyl]propane, 9,9-bis[4-{(2-hydroxy-3-acryloxy)propoxy}phenyl]fluorene, 9,9-bis[4-{(2-hydroxy-3-acryl-oxy)propoxyethoxy}phenyl]fluorine, and reaction products of epoxy resins based on novolacs with (meth)acrylic acid.

Polyethers obtained from the reaction of the polyols or polyepoxides with the unsaturated compounds with a hydroxy group such as 2-hydroxyethyl (meth)acrylate, vinyl alcohol can also be used as component (a).

Also suitable as components (a) are the amides of identical or different, unsaturated carboxylic acids with aromatic, cycloaliphatic and aliphatic polyamines having preferably 2 to 6, especially 2 to 4, amino groups.

Other examples are unsaturated urethanes derived from a polyisocyanate and an unsaturated compound having a hydroxy group or from a polyisocyanate, a polyol and an unsaturated compound having a hydroxy group.

Other examples are polyesters, polyamides, or polyurethanes having ethylenically unsaturated groups in the chain.

Other suitable polymers with acrylate or methacrylate groups in the side chains are, for example, solvent soluble or alkaline soluble polyimide precursors, for example poly(amic acid ester) compounds, having the photopolymerizable side groups either attached to the back-bone or to the ester groups in the molecule, i.e. according to EP 624826. Such oligomers or polymers can be formulated optionally with reactive diluents, like polyfunctional (meth)acrylates in order to prepare highly sensitive polyimide precursor resists.

Further examples of the component a) are also the abovementioned polymers or oligomers having at least one carboxyl function and at least two ethylenically unsaturated groups within the molecular structure, such as a resin obtained by the reaction of a saturated or unsaturated polybasic acid anhydride with a product of the reaction of phenol or cresol novolac epoxy resin and an unsaturated monocarboxylic acid.

Other examples are the products from the polycondensation reaction and/or addition reaction of the compound of formula (XIV) with one or more abovementioned polybasic acid anhydrides.

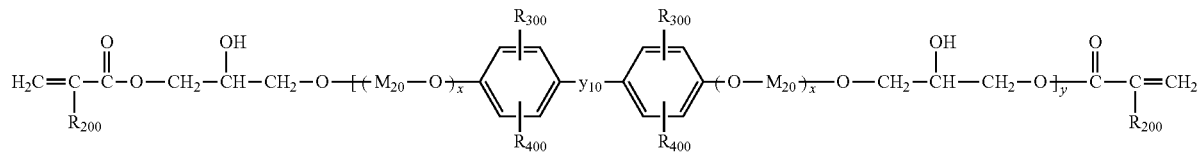

(XIV)

wherein $Y_{10}$ is

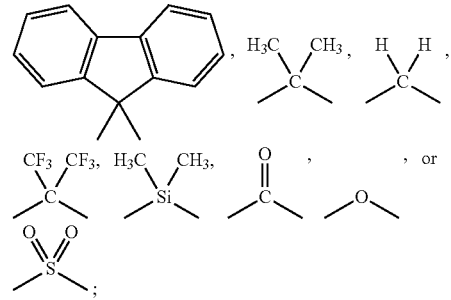

$R_{200}$ is hydrogen or methyl,
$R_{300}$ and $R_{400}$ independently of each other are hydrogen, methyl, Cl, or Br, $M_{20}$ is substituted or unsubstituted alkylene having 1 to 10 carbon atoms, x is 0 to 5, and y is 1 to 10. Examples of such compounds as component (a) are described in JP2002-206014A, JP2004-69754A, JP2004-302245A, JP2005-77451 A, JP2005-316449A, JP2005-338328A and JP3754065B2.

Polymers or oligomers as abovementioned have for example a molecular weight of about 1,000 to 1,000,000, preferably 2,000 to 200,000 and an acid value of about 10 to 200 mg KOH/g, preferably 20 to 180 mg KOH/g.

A preferred photopolymerizable composition comprises as component (a) a compound having at least two ethylenically unsaturated bonds and at least one carboxylic acid group in the molecule, in particular a reaction product obtained by adding an epoxy group containing unsaturated compound to a part of the carboxyl groups of a carboxylic acid group containing polymer or a reaction product of the compound shown below with one or more polybasic acid anhydrides. Further preferred components (a) comprise a compound obtained from the reaction of a compound of the formula (XIV) with one or more polybasic acid anhydrides.

Further examples are the above-mentioned reaction products obtained by adding an epoxy group containing unsaturated compound to a part of the carboxyl groups of a carboxylic acid group containing polymer.

Concrete examples of the compounds are, for example a reaction product of a copolymer of styrene, α-methyl styrene and acrylic acid or a copolymer of methyl methacrylate and acrylic acid with 3,4-epoxycyclohexylmethyl (meth)acrylate.

Unsaturated compounds having a hydroxy group such as 2-hydroxyethyl (meth)acrylate and glycerol mono(meth)acrylate can be used instead of the above mentioned epoxy group containing unsaturated compounds as the reactant for carboxylic acid group containing polymers.

Other examples are half esters of anhydride containing polymers, for example reaction products of a copolymer of maleic anhydride and one or more other polymerizable compounds with (meth)acrylates having an alcoholic hydroxy group such as 2-hydroxyethyl (meth)acrylate or having an epoxy group for example such as the compounds described in the formula (V-1)-(V-15).

Reaction products of polymers having alcoholic hydroxy groups such as copolymers of 2-hydroxyethyl (meth)acrylate, (meth)acrylic acid, benzy methacylate and styrene, with (meth)acrylic acid or (meth)acryl chloride can also be used as component (a).

Other examples are reaction products of a polyester with terminal unsaturated groups, which is obtained from the reaction of a dibasic acid anhydride and a compound having at least two epoxy groups followed by further reaction with an unsaturated compound, with a polybasic acid anhydride.

Further examples are resins obtained by the reaction of a saturated or unsaturated polybasic acid anhydride with a reaction product obtained by adding epoxy group containing (meth)acrylic compound to all of the carboxyl groups of a carboxylic acid containing polymer as mentioned above.

The photopolymerizable compounds can be used alone or in any desired mixtures.

In a color filter resist composition the whole amount of the monomers contained in the photo-polymerizable composition is preferably 5 to 80% by weight, in particular 10 to 70% by weight based on the whole solid contents of the composition, i.e. the amount of all components without the solvent(s).

As the binder used in the color filter resist composition, which is soluble in an alkaline aqueous solution and insoluble in water, for example, a homopolymer of a polymerizable compound having one or more acid groups and one or more polymerizable unsaturated bonds in the molecule, or a copolymer of two or more kinds thereof, and a copolymer of one or more polymerizable compounds having one or more unsaturated bonds copolymerizable with these compounds and containing no acid group, can be used. As described above, such compounds can be obtained by copolymerizing one or more kinds of a low molecular compound having one or more acid groups and one or more polymerizable unsaturated bonds in the molecule with one or more polymerizable compounds having one or more unsaturated bonds copolymerizable with these compounds and containing no acid group as described above. A high molecular compound having a —COOH group as acid group is particularly preferred.

Preferable examples of copolymers are copolymers of (meth)acrylate and (meth)acrylic acid as described above.

Examples of the polymerizable compounds having one or more —COOH groups and one or more polymerizable unsaturated bonds in a molecule and the polymerizable compounds having one or more polymerizable unsaturated bond and containing no acid group described above can be used for the organic polymer binder.

The weight-average molecular weight of the binders is preferably 500 to 1,000,000, e.g. 3,000 to 1,000,000, more preferably 5,000 to 400,000.

These compounds may be used singly or as a mixture of two or more kinds. The content of the binder in the light-sensitive resin composition is preferably 10 to 95 weight %, more preferably 15 to 90 weight % based on the whole solid matters.

Examples for color filter resists, the composition of such resists and the processing conditions are given by T. Kudo et al., Jpn. J. Appl. Phys. Vol. 37 (1998) 3594; T. Kudo et al., J. Photopolym. Sci. Technol. Vol 9 (1996) 109; K. Kobayashi, Solid State Technol. November 1992, p. S15-S18; U.S. Pat. Nos. 5,368,976; 5,800,952; 5,882,843; 5,879,855; 5,866,298; 5,863,678; JP 06-230212A; EP320264; JP 09-269410A; JP 10-221843A; JP 01-090516A; JP 10-171119A, U.S. Pat. Nos. 5,821,016, 5,847,015, 5,882,843, 5,719,008, EP881541, or EP902327.

The photoinitiator mixtures of the present invention can be used in color filter resists, for example, such as those given as examples above, or can partially or fully replace the known photoinitiators in such resists. It is understood by a person skilled in the art that the use of the new photoinitiator mixtures of the present invention is not limited to the specific binder resins, crosslinkers and formulations of the color filter resist examples given hereinbefore but can be used in conjunction with any radically polymerizable component in combination with a dye or color pigment or latent pigment to form a photosensitive color filter ink or color filter resist.

The photosensitive compositions of the present invention, as already stated above, are also suitable for the preparation of the black matrix of color filters. Said black matrix composition for example comprises a photoinitiator mixture of the present invention,
  an organic binder, in particular an organic binder, which is an epoxy acrylate resin having carboxyl groups,
  a black coloring material,
  a polymer dispersant, in particular a polymer dispersant containing basic functional groups,
  a photopolymerizable monomer.

The person skilled in the art is familiar with such formulations. Examples of suitable black matrix compositions and the components (other than the photoinitiator) as described above are given in JP Patent No. 3754065, the disclosure of which hereby is incorporated by reference.

It is obvious to those skilled in the art, that the photosensitive compositions of the present invention can be used for generating red, green and blue color pixels and a black matrix, for the manufacture of a color filter, regardless of the above described differences in processing, regardless, of additional layers which can be applied and regardless of differences in the design of the color filter. The use of a composition according to the present invention to form colored elements shall not be regarded as limited by different designs and manufacturing processes of such color filters.

The photoinitiator mixtures and the corresponding photocurable compositions of the present invention are in particular suited for the preparation of red, green and blue color filters.

They may also be employed in the black matrix of a color filter.

The photo-sensitive composition of the present invention can suitably be used for forming a color filter but will not be limited to this application. It is useful as well for example for a recording material, a resist material, a protective layer, a dielectric layer, an optical film such as overcoat film, anti-reflective film, anti-glare film, hard coat, prism sheet, retardation film, alignment film and sealant in display applications and display elements, a paint, and a printing ink.

The photosensitive compositions according to the invention are also suitable for manufacturing interlayer insulating layers or dielectric layers in a liquid crystal display, and more particularly in a reflection type liquid crystal display including an active matrix type display having a thin film transistor (TFT) as a switching device, and a passive matrix type without a switching device.

The photosensitive compositions according to the invention can further be used for manufacturing spacers, which control a cell gap of the liquid crystal part in liquid crystal display panels.

The photocurable compositions according to the invention are suitable for producing spacers for liquid crystal displays (as described above) because of their high sensitivity.

The photosensitive compositions according to the invention are also suitable for manufacturing microlens arrays used in liquid crystal display panels, image sensors and the like.

Because the photocurable compositions according to the invention have low yellowing properties, both thermally and photochemically, they are suitable for the production of microlens arrays as described above.

The novel radiation-sensitive compositions are also suitable for photo-lithographic steps used in the production process of plasma display panels (PDP), particularly for the imaging forming process of barrier rib, phosphor layer and electrodes.

The compositions according to the invention also find application for the production of one- or more-layered materials for the image recording or image reproduction (copies, reprography), which may be mono- or polychromatic. Furthermore the materials are suitable for color proofing systems. In this technology formulations containing microcapsules can be applied and for the image production the radiation curing can be followed by a thermal treatment. Such systems and technologies and their applications are for example disclosed in U.S. Pat. No. 5,376,459.

The photoinitiator mixtures are also suitable as photoinitiators in the holographic data storage application. Said photoinitiators generate radicals and initiate polymerization of monomer upon irradiation with blue laser radiation, suitable for holographic data storage. The wavelength range of the blue laser is 390-420 nm, preferably 400-410 nm and particularly 405 nm. Holographic storage systems (holographic recording media) are for example used to record and to retrieve a large amount of data with fast access time. The photoinitiator mixtures of the invention are for example in particular suitable for systems as described for example in WO 03/021358.

It was found that the photoinitiator mixtures of the present invention combine high reactivity with low absorbance at 405 nm and are suitable for this application. Dyes and sensitizers can also be added to the formulations. Suitable dyes and sensitizers for blue laser radiation are for example coumarines, xanthones, thioxanthones and benzophenones.

It was found that the photoinitiator mixtures allow photopolymerization of monomers in thick layers, such as required for holographic data storage, with high sensitivity and yield recording layers which are sensitive to blue laser radiation. The photoinitiator mixtures are in particular suitable for the preparation of optical articles (for example optical waveguides) or holographic recording media e.g. comprising a polymer and an organic photoinitiator mixture as described above, having a maximum absorption at a UV wavelength in the range of 340-450 nm, wherein the refractive index contrast adjusted sensitivity is greater than $3 \times 10^{-6} \Delta n/(mJ/cm^2)$.

Photocuring further is of great importance for printing applications, since the drying time of the ink is a critical factor for the production rate of graphic products, and should be in the order of fractions of seconds. UV-curable inks are particularly important for screen printing, offset inks, ink-jet inks, flexographic printing inks, intaglio inks, electrophotographic inks, sheetfed inks, overprint varnishes or primers.

Subject of the invention therefore also is a photopolymerizable composition as described above, which is a printing ink, in particular an offset printing ink.

As already mentioned above, the novel photoinitiator mixtures are highly suitable also for producing printing plates e.g. flexo printing plates or offset printing plates. This application uses, for example, mixtures of soluble linear polyamides or styrene/butadiene and/or styrene/isoprene rubber, polyacrylates or polymethyl methacrylates containing carboxyl groups, polyvinyl alcohols or urethane acrylates with photopolymerizable monomers, for example acrylamides and/or methacrylamides, or acrylates and/or methacrylates, and a photoinitiator. Films and plates of these systems (wet or dry) are exposed over the negative (or positive) of the printed original, and the uncured parts are subsequently washed out using an appropriate solvent or aqueous solutions.

Printing inks are known to the person skilled in the art, are used widely in the art and are described in the literature.

They are, for example, pigmented printing inks and printing inks coloured with dyes.

A printing ink is, for example, a liquid or paste-form dispersion that comprises colorants (pigments or dyes), binders and also optionally solvents and/or optionally water and additives. In a liquid printing ink, the binder and, if applicable, the additives are generally dissolved in a solvent. Customary viscosities in the Brookfield viscometer are, for example, from 20 to 5000 mPa·s, for example from 20 to 1000 mPa·s, for liquid printing inks. For paste-form printing inks, the values range, for example, from 1 to 100 Pa·s, preferably from 5 to 50 Pa·s. The person skilled in the art will be familiar with the ingredients and compositions of printing inks. Suitable pigments, like the printing ink formulations customary in the art, are generally known and widely described.

Printing inks comprise pigments advantageously in a concentration of, for example, from 0.01 to 40% by weight, preferably from 1 to 25% by weight, especially from 5 to 10% by weight, based on the total weight of the printing ink.

The printing inks can be used, for example, for intaglio printing, gravure printing, flexographic printing, screen printing, offset printing, lithography or continuous or dropwise ink-jet printing on material pretreated in accordance with the process of the invention using generally known formulations, for example in publishing, packaging or shipping, in logistics, in advertising, in security printing or in the field of office equipment.

Suitable printing inks are both solvent-based printing inks and water-based printing inks. Of interest are, for example, printing inks based on aqueous acrylate. Such inks are to be understood as including polymers or copolymers that are obtained by polymerisation of at least one monomer containing a group

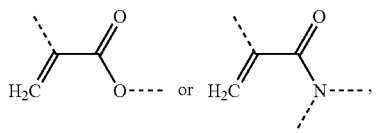

and that are dissolved in water or a water-containing organic solvent. Suitable organic solvents are water-miscible solvents customarily used by the person skilled in the art, for example alcohols, such as methanol, ethanol and isomers of propanol, butanol and pentanol, ethylene glycol and ethers thereof, such as ethylene glycol methyl ether and ethylene glycol ethyl ether, and ketones, such as acetone, ethyl methyl ketone or cyclo, for example isopropanol. Water and alcohols are preferred.

Suitable printing inks comprise, for example, as binder primarily an acrylate polymer or copolymer and the solvent is selected, for example, from the group consisting of water, $C_1$-$C_5$alcohols, ethylene glycol, 2-($C_1$-$C_5$alkoxy)-ethanol, acetone, ethyl methyl ketone and any mixtures thereof.

In addition to the binder, the printing inks may also comprise customary additives known to the person skilled in the art in customary concentrations.

For intaglio or flexographic printing, a printing ink is usually prepared by dilution of a printing ink concentrate and can then be used in accordance with methods known per se.

The printing inks may, for example, also comprise alkyd systems that dry oxidatively.

The printing inks are dried in a known manner customary in the art, optionally with heating of the coating.

A suitable aqueous printing ink composition comprises, for example, a pigment or a combination of pigments, a dispersant and a binder.

Dispersants that come into consideration include, for example, customary dispersants, such as water-soluble dispersants based on one or more arylsulfonic acid/formaldehyde condensation products or on one or more water-soluble oxalkylated phenols, non-ionic dispersants or polymeric acids.

The arylsulfonic acid/formaldehyde condensation products are obtainable, for example, by sulfonation of aromatic compounds, such as naphthalene itself or naphthalene-containing mixtures, and subsequent condensation of the resulting arylsulfonic acids with formaldehyde. Such dispersants are known and are described, for example, in U.S. Pat. No. 5,186,846 und DE-A-197 27 767. Suitable oxalkylated phenols are likewise known and are described, for example, in U.S. Pat. No. 4,218,218 und DE-A-197 27 767. Suitable non-ionic dispersants are, for example, alkylene oxide adducts, polymerisation products of vinylpyrrolidone, vinyl acetate or vinyl alcohol and co- or ter-polymers of vinyl pyrrolidone with vinyl acetate and/or vinyl alcohol. It is also possible, for example, to use polymeric acids which act both as dispersants and as binders.

Examples of suitable binder components that may be mentioned include (meth-)acrylate-group-containing, vinyl-group-containing and/or, depending on the intended application, epoxy-group-containing monomers, prepolymers and polymers and mixtures thereof. Further examples are melamine acrylates and silicone acrylates. The acrylate compounds may also be non-ionically modified (e.g. provided with amino groups) or ionically modified (e.g. provided with acid groups or ammonium groups) and used in the form of aqueous dispersions or emulsions (e.g. EP-A-704 469, EP-A-12 339). Furthermore, in order to obtain the desired viscosity the solventless acrylate polymers can be mixed with so-called reactive diluents, for example vinyl-group-containing monomers. Further suitable binder components are epoxy-group-containing compounds.

The printing ink compositions may also comprise as additional component, for example, an agent having a water-retaining action (humectant), e.g. polyhydric alcohols, polyalkylene glycols, which renders the compositions especially suitable for ink-jet printing.

It will be understood that the printing inks may comprise further auxiliaries, such as are customary especially for (aqueous) ink-jet inks and in the printing and coating industries, for example preservatives (such as glutardialdehyde and/or tetramethylolacetyleneurea, anti-oxidants, degassers/defoamers, viscosity regulators, flow improvers, anti-settling agents, gloss improvers, lubricants, adhesion promoters, anti-skin agents, matting agents, emulsifiers, stabilisers, hydrophobic agents, light stabilisers, handle improvers and anti-statics. When such agents are present in the compositions, their total amount is generally $\leq 1\%$ by weight, based on the weight of the preparation.

Printing inks suitable in process step d2) include, for example, those comprising a dye (with a total content of dyes of e.g. from 1 to 35% by weight, based on the total weight of the ink).

Dyes suitable for colouring such printing inks are known to the person skilled in the art and are widely available commercially, e.g. from Ciba Spezialitätenchemie AG, Basel.

Such printing inks may comprise organic solvents, e.g. water-miscible organic solvents, for example $C_1$-$C_4$alcohols, amides, ketones or ketone alcohols, ethers, nitrogen-containing heterocyclic compounds, polyalkylene glycols, $C_2$-$C_6$alkylene glycols and thioglycols, further polyols, e.g. glycerol and $C_1$-$C_4$alkyl ethers of polyhydric alcohols, usually in an amount of from 2 to 30% by weight, based on the total weight of the printing ink.

The printing inks may also, for example, comprise solubilisers, e.g. ∈-caprolactam.

The printing inks may, inter alia for the purpose of adjusting the viscosity, comprise thickeners of natural or synthetic origin. Examples of thickeners include commercially available alginate thickeners, starch ethers or locust bean flour ethers. The printing inks comprise such thickeners e.g. in an amount of from 0.01 to 2% by weight, based on the total weight of the printing ink.

It is also possible for the printing inks to comprise buffer substances, for example borax, borate, phosphate, polyphosphate or citrate, in amounts of e.g. from 0.1 to 3% by weight, in order to establish a pH value of e.g. from 4 to 9, especially from 5 to 8.5.

As further additives, such printing inks may comprise surfactants or humectants. Surfactants that come into consideration include commercially available anionic and non-ionic surfactants. Humectants that come into consideration include, for example, urea or a mixture of sodium lactate (advantageously in the form of a 50 to 60% aqueous solution) and glycerol and/or propylene glycol in amounts of e.g. from 0.1 to 30% by weight, especially from 2 to 30% by weight, in the printing inks.

Furthermore, the printing inks may also comprise customary additives, for example foam-reducing agents or especially substances that inhibit the growth of fungi and/or bacteria. Such additives are usually used in amounts of from 0.01 to 1% by weight, based on the total weight of the printing ink.

The printing inks may also be prepared in customary manner by mixing the individual components together, for example in the desired amount of water.

As already mentioned, depending upon the nature of the use, it may be necessary for e.g. the viscosity or other physical properties of the printing ink, especially those properties which influence the affinity of the printing ink for the substrate in question, to be adapted accordingly.

The printing inks are also suitable, for example, for use in recording systems of the kind in which a printing ink is expressed from a small opening in the form of droplets which are directed towards a substrate on which an image is formed. Suitable substrates are, for example, textile fibre materials, paper, plastics or aluminium foils pretreated by the process according to the invention. Suitable recording systems are e.g. commercially available ink-jet printers.

Preference is given to printing processes in which aqueous printing inks are used.

Suitable monomers in particular for ink-jet printing inks, include those compounds which have at least one carbon-carbon unsaturated bond. Non limiting examples of such monomers are:
(meth)acrylic acid and salts thereof; (meth)acrylic acid esters such as alkylesters e.g. methyl, ethyl, 2-chloroethyl, N-dimethylaminoethyl, n-butyl, isobutyl-, pentyl, hexyl, cyclohexyl, 2-ethylhexyl, octyl, isobornyl[2-exobornyl]esters; phenyl, benzyl-, and o-, m- and p-hydroxyphenyl esters; hydroxyalkylesters e.g. 2-hydroxyethyl, 2-hydroxypropyl, 4-hydroxybutyl, 3,4-dihydroxybutyl or glycerol[1,2,3-propanetriol]esters; epoxyalkylesters e.g. glycidyl, 2,3-epoxybutyl, 3,4-epoxy butyl, 2,3-epoxycyclohexyl, 10,11-epoxyundecyl esters; (meth)acrylamides, N-substituted (meth) acrylamides, e.g. N-methylolacrylamide, N-methylolmethacrylamide, N-ethylacrylamide, N-ethylmethacrylamide, N-hexylacrylamide, N-hexylmethacrylamide, N-cyclohexylacrylamide, N-cyclohexylmethacrylamide-, N-hydroxy-ethylacrylamide, N-phenylacrylamide, N-phenylmethacrylamide, N-benzylacrylamide, N-benzylmetacrylamide, N-nitrophenylacrylamide, N-nitrophenylmethacrylamide, N-ethyl-N-phenylacrylamide, N-ethyl-N-phenylmethacrylamide, N-(4-hydroxyphenyl)acrylamide, and N-(4-hydroxyphenyl)methacrylamide, IBMAA (N-isobutoxymethyl acrylamide), (meth)acryl-nitriles; unsaturated acid anhydrides such as itaconic anhydride, maleic anhydride, 2,3-dimethyl maleic anhydride, and 2-chloromaleic anhydride, unsaturated acid esters such as maleic acid esters, phthalic acid esters, itaconic acid esters, [methylene succinic acid esters];
styrenes, such as methyl styrene, chloromethyl styrene, and o-, m-, and p-hydroxystyrene, divinylbenzene; vinyl chloride and vinylidene chloride; vinyl ethers such as isobutyl vinyl ether, ethyl vinylether, 2-chloroethyl vinylether, hydroxyethyl vinylether, propyl vinylether, butyl vinylether, isobutyl vinyl ether, octyl vinylether and phenyl vinylether; vinyl and allyl esters such as vinyl acetate, vinyl acrylate, vinyl chloroacetate, vinyl butyrate and vinyl benzoate, divinyl succinate, diallyl phthalate, triallyl phosphate; isocyanurates such as triallyl isocyanurate and tris(2-acryloylethyl)isocyanurate; N-vinyl heterocyclic compounds, N-vinylpyrrolidone or suitably substituted vinylpyrrolidones, N-vinylcarbazol, N-vinylcaprolactam or suitably substituted vinylcaprolactames, 4-vinyl-pyridine.

Typical examples for esters are the ones as given hereinbefore.

The following esters of alkoxylated polyols are also suitable: glycerol ethoxylate triacrylate, glycerol propoxylate triacrylate, trimethylolpropane ethoxylate triacrylate, trimethylolpropane propoxylate triacrylate, pentaerythritol ethoxylate tetraacrylate, pentaerythritol propoxylate triacrylate, pentaerythritol propoxylate tetraacrylate, neopentyl glycol ethoxylate diacrylate, neopentyl glycol propoxylate diacrylate.

Non limiting examples of higher molecular weight (oligomeric) polyunsaturated compounds (also known as prepolymers) are esters of ethylenically unsaturated mono- or polyfunctional carboxylic acids and polyols or polyepoxides, and polymers having ethylenically unsaturated groups in the chain or in side groups, e.g. unsaturated polyesters, polyamides and polyurethanes and copolymers thereof, alkyd resins; polybutadiene and butadiene copolymers, polyisoprene and isoprene copolymers, polymers and copolymers having (meth)acrylic groups in side chains such as methacrylated urethanes and also mixtures of one or more such polymers.

Examples of suitable mono- or poly-functional unsaturated carboxylic acids are acrylic acid, methacrylic acid, crotonic acid, itaconic acid, cinnamic acid, maleic acid, fumaric acid, itaconic acid, and unsaturated fatty acids such as linolenic acid and oleic acid. Acrylic and methacrylic acid are preferred.

It is also possible, however, to use saturated di- or poly-carboxylic acids in admixture with unsaturated carboxylic acids. Examples of suitable saturated di- or poly-carboxylic acids include, for example, tetrachlorophthalic acid, tetrabromophthalic acid, phthalic anhydride, adipic acid, tetrahydrophthalic acid, isophthalic acid, terepthalic acid, trimellitic acid, heptane-dicarboxylic acid, sebacic acid, dodecanedicarboxylic acid, hexahydrophthalic acid, etc.

Suitable polyols are aromatic and, especially, aliphatic and cycloaliphatic polyols. Examples of aromatic polyols are hydroquinone, 4,4'-dihydroxydiphenyl, 2,2-di(4-hydroxyphenyl)propane, and novolaks and resols. Examples of polyepoxides are those based on the said polyols, especially the aromatic polyols and epichlorohydrin. Also suitable as polyols are polymers and copolymers that contain hydroxyl groups in the polymer chain or in side groups, e.g. polyvinyl alcohol and copolymers thereof or polymethacrylic acid hydroxyalkyl esters or copolymers thereof. Further suitable polyols are oligoesters having hydroxyl terminal groups.

Examples of aliphatic and cycloaliphatic polyols include alkylenediols having preferably from 2 to 12 carbon atoms, such as ethylene glycol, 1,2- or 1,3-propanediol, 1,2-, 1,3- or 1,4-butanediol, pentanediol, hexanediol, octanediol, dodecanediol, diethylene glycol, triethylene glycol, polyethylene glycols having molecular weights of preferably from 200 to 1500, 1,3-cyclopentanediol, 1,2-, 1,3- or 1,4-cyclohexanediol, 1,4-dihydroxymethylcyclohexane, glycerol, tris(β-hydroxyethyl)amine, trimethylolethane, trimethylolpropane, pentaerythritol, dipentaerythritol and sorbitol.

The polyols may be partially or fully esterified by one or by different unsaturated carboxylic acid(s), it being possible for the free hydroxyl groups in partial esters to be modified, for example etherified, or esterified by other carboxylic acids.

Preferred in ink-jet ink formulations are: (meth)acrylated epoxy esters; (meth)acrylated poly-esters or vinyl-ether-group-containing polyesters, (meth)acrylated polyurethanes, polyethers and polyols.

A preferred component used in UV-curable inkjet are acrylates which have been modified by reaction with primary or secondary amines, as described, for example, in U.S. Pat. No. 3,844,916, EP280222, U.S. Pat. Nos. 5,482,649 or 5,734,002. Such amine-modified acrylates are also termed aminoacrylates. It is known that in the presence of aminoacrylates UV-curable systems show an increased curing performance. They are useful to overcome the oxygen inhibition typically observed for radical induced polymerization reactions, especially for low viscous systems like UV-curable inkjet. Aminoacrylates are obtainable, for example, under the name EBECRYL 80, EBECRYL 81, EBECRYL 83, EBECRYL P115, EBECRYL 7100 from UCB Chemicals, under the name Laromer PO 83F, Laromer PO 84F, Laromer PO 94F from BASF, under the name PHOTOMER 4775 F, PHOTOMER 4967 F from Cognis or under the name CN501, CN503, CN550 from Cray Valley or under the tradename Genomer 5275 from Rahn AG.

These aminoacrylates are in particular suitable as component (a) for compositions comprising a photoinitiator mixture consisting of at least one compound of the formula I and at least one benzophenone compound (BK) or at least one thioxanthone compound (TX) as defined above.

It will be clear that mixtures of all these cited monomers, prepolymers, polymers and oligomers can be used in the ink compositions comprising the novel photoinitiator mixture according to the present invention.

The amount of the photopolymerizable monomer, oligomer or prepolymer in this connection is for example 10 to 80 wt %, preferably 10 to 60 wt %.

The inks comprising the photoinitiator mixtures of the present invention may besides to radically polymerizable components also comprise cationic-curable compositions having a low viscosity which comprise at least one aliphatic or aromatic epoxide, at least one polyol or polyvinyl polyols as mentioned above, and at least one cation-generating photoinitiator. A number of these epoxides are well known in the art and are commercially available.

Photoinitiators that can be used in the cationic photocurable compositions are, for example, aryl iodonium salts and aryl sulfonium salts.

Emphasized are such hybrid systems that contain cationically and radically polymerisable and photopolymerisable raw materials. Examples of cationically polymerisable systems include cyclic ethers, especially epoxides and oxetanes, and also vinyl ethers and hydroxy-containing compounds. Lactone compounds and cyclic thioethers as well as vinyl thioethers can also be used. Further examples include aminoplastics or phenolic resole resins. These are especially melamine, urea, epoxy, phenolic, acrylic, polyester and alkyd resins, but especially mixtures of acrylic, polyester or alkyd resins with a melamine resin. Radiation curable resins contain ethylenically unsaturated compounds, especially (meth)acrylate resins.

Furthermore interesting are hybrid systems that are photopolymerized in a first stage and then crosslinked through thermal post-treatment in a second stage. Such hybrid systems comprise an unsaturated compound in mixtures with non-photopolymerizable film-forming components. These may, for example, be physically drying polymers or solutions thereof in organic solvents, for example nitrocellulose or cellulose acetobutyrate. However, they may also be chemically or thermally curable resins, for example polyisocyanates, polyepoxides or melamine resins.

Other compositions suitable as for example ink-jet inks are dual cure compositions, which are cured first by heat and subsequently by UV or electron irradiation, or vice versa, and whose components contain ethylenic double bonds as described above capable to react on irradiation with UV light in presence of a photoinitiator, in the context of the invention the novel photoinitiator mixture as described above.

Ink jet inks for example contain a colorant. A wide variety of organic and inorganic dyes and pigments, alone or in combination may be selected for use in ink jet ink compositions; the person skilled in the art is familiar with the appropriate coice. The pigment particles should be sufficiently small (0.005 to 15 μm) to permit free flow of the ink at the ejecting nozzles. The pigment particles should preferably be 0.005 to 1 μm.

Very fine dispersions of pigments and their preparation are disclosed in e.g. U.S. Pat. No. 5,538,548.

The inks preferably comprise a total content of colorant of 1 to 35% by weight, in particular 1 to 30% by weight, and preferably 1 to 20% by weight, based on the total weight of ink. A limit of 2.5% by weight, in particular 5% by weight, and preferably 7.5% by weight, is preferred here as the lower limit.

Suitable colorants are for example pure pigment powders such as Cyan IRGALITE® Blue GLO (Ciba Inc.) or pigment preparations such as MICROLITH-pigment preparations.

Ink jet inks may include a variety of further additives such as for example surfactants, biocides, buffering agents, antimold agents, pH adjustment agents, electric conductivity adjustment agents, chelating agents, anti-rusting agents, polymerisation inhibitors, light stabilizers, and the like. Such additives may be included in the ink jet inks in any effective amount, as desired.

Compositions according to the present invention may further contain organic solvents, for example, ketones, ethers and esters, such as methyl ethyl ketone, isobutyl methyl ketone, cyclopentanone, cyclohexanone, N-methylpyrrolidone, dioxane, tetrahydrofuran, 2-methoxy-ethanol, 2-ethoxyethanol, 1-methoxy-2-propanol, 1,2-dimethoxyethane, ethyl acetate, n-butyl acetate and ethyl 3-ethoxypropionate or 1-Isopropyl-2,2-dimethyltrimethylendiisobutyrate available as TXIB from Eastman.

The reactive diluent in the ultraviolet ray curable ink and the ultraviolet ray curable ink composition is a monomer which has at least one double bond reactive group at the molecule terminal. Examples thereof are monofunctional caprolactone acrylate, tridecyl acrylate, isodecyl acrylate, isooctyl acrylate, isomiristyl acrylate, isostearyl acrylate, 2-ethylhexyl-diglycol acrylate, 2-hydroxybutyl acrylate, 2-acryloyloxyethyl hexahydrophthalic acid, neopentyl glycol acrylic acid benzoic acid ester, isoamylacylate, lauryl acrylate, stearyl acrylate, butoxyethyl acylate, ethoxy-diethylene glycol acrylate, methoxy-triethylene glycol acrylate, methoxy-polyethylene glycol acrylate, methoxydipropyleneglycol acrylate, phenoxyethyl acrylate, phenoxy-polyethylene glycol acrylate, nonylphenol ethylene oxide adduct acrylate, tetrahydrofurfuryl acrylate, isobonyl acrylate, 2-hydroxyethyl acrylate, 2-hydroxypropyl acrylate, 2-hydroxy-3-phenoxypropyl acrylate, 2-acryloyloxyethyl succinic acid, 2-acryloyloxyethyl-phthalic acid and 2-acryloyloxyethyl-2-hydroxyethylphthalic acid; difunctional hydroxypivalic acid neopenthylglycol diacrylate, polytetramethylene glycol diacrylate, trimethylol propane acrylic acid benzoic acid ester, diethylene glycol diacrylate, triethylene glycol diacrylate, tripropylene glycol diacrylate, tetraethylene glycol diacrylate, polyethylene glycol (200) diacrylate, polyethylene glycol (400) diacrylate, polyethylene glycol (600) diacrylate, polyethylene glycol (1000) diacrylate, polypropylene (400) diacrylate, polypropylene (700) diacrylate, neopentyl glycol diacrylate, 1,3-butanediol diacrylate, 1,4-butanediol diacrylate, 1,6-hexanediol diacrylate, 1,9-nonanediol diacrylate, dimethylol-tricyclodecane diacrylate, bisphenol A ethylene oxide adduct diacrylate and bisphenol A propyleneoxide adduct diacrylate; trifunctional trimethylolpropane triacrylate, ethylene oxide modified trimethyl propane triacrylate, ethylene oxide modified trimethylolpropane triacrylate, pentaerythritol triacrylate, tris(2-hydroxyethyl)isocyanurate triarylate and propoxylated gliceril triacrylate; tetrafunctional pentaditrimethylol propane tetraacrylate, ethoxylated pentaerythritol tetraacrylate, pentaerythritol tetraacrylate; pentafunctional dipentaerythritol hydroxypentaacrylate; and hexa-functional dipentaerythritol hexaacrylate; and modifications thereof. These can be used alone or in a combination.

The amount of the reactive diluent is, for example, 40-80 wt %, 10 to 90 wt %, preferably 20 to 80 wt %.

Another field where photocuring is employed is the coating of metals, in the case, for example, of the coating of metal plates and tubes, cans or bottle caps, and the photocuring of polymer coatings, for example of floor or wall coverings based on PVC.

Examples of the photocuring of paper coatings are the colourless varnishing of labels, record sleeves and book covers.

The photoinitiators of the present invention are also suitable for use in UV-curable adhesives; e.g. in the preparation of pressure-sensitive adhesives, laminating adhesives, hot-melt adhesives, moisture-cure adhesives, silane reactive adhesives or silane reactive sealants and the like, and related applications. Said adhesives can be hot melt adhesives as well waterborne or solvent borne adhesives, liquid solventless adhesives or 2-part reactive adhesives. In particular suitable are pressure-sensitive adhesives (PSA), for example uv-curable hot melt pressure sensitive adhesives. Said adhesives for example comprise at least one rubber component, at least one resin component as tackyfier and at least one oil component, for example in the weight ratio 30:50:20. Suitable tackyfiers are natural or synthetic resins. The person skilled in the art is aware of suitable corresponding compounds as well as of suitable oil components or rubbers.

The pre-polymerized adhesives containing the isocyanates, for example in blocked form, can for example be processed at high temperature and coated onto the substrate following the hotmelt process, afterwards full cure is achieved by an additional curing step involving the blocked isocyanates, which is realized by photoactivation of the photolatent catalyst.

The compounds according to the invention may also be used as initiators for emulsion, bead or suspension polymerisation processes or as initiators of polymerisation for the fixing of orientation states of liquid-crystalline monomers and oligomers, or as initiators for the fixing of dyes on organic materials.

Also of interest is the use of the novel photoinitiators for curing shaped articles made from composite compositions. The composite compound consists of a self-supporting matrix material, for example a glass fibre fabric, or alternatively, for example, plant fibres [cf. K.-P. Mieck, T. Reussmann in Kunststoffe 85 (1995), 366-370], which is impregnated with the photocuring formulation. Shaped parts comprising composite compounds, when produced using the novel compounds, attain a high level of mechanical stability and resistance. The novel compounds can also be employed as photocuring agents in moulding, impregnating and coating compositions as are described, for example, in EP7086. Examples of such compositions are gel coat resins, which are subject to stringent requirements regarding curing activity and yellowing resistance, and fibre-reinforced mouldings, for example, light diffusing panels which are planar or have lengthwise or crosswise corrugation. Techniques for producing such mouldings, such as hand lay-up, spray lay-up, centrifugal casting or filament winding, are described, for example, by P. H. Selden in "Glasfaserverstärkte Kunststoffe", page 610, Springer Verlag Berlin-Heidelberg-New York 1967. Examples of articles which can be produced by these techniques are boats, fibre board or chipboard panels with a double-sided coating of glass fibre-reinforced plastic, pipes, containers, etc. Further examples of moulding, impregnating and coating compositions are UP resin gel coats for mouldings containing glass fibres (GRP), such as corrugated sheets and paper laminates. Paper laminates may be based on urea resins or melamine resins. Prior to production of the laminate, the gel coat is produced on a support (for example a film). The novel photocurable compositions can also be used for casting resins or for embedding articles, for example electronic components, etc.

The compositions and compounds according to the invention can be used for the production of holographies, waveguides, optical switches wherein advantage is taken of the development of a difference in the index of refraction between irradiated and unirradiated areas.

The use of photocurable compositions for imaging techniques and for the optical production of information carriers is also important. In such applications, as already described above, the layer (wet or dry) applied to the support is irradiated imagewise, e.g. through a photomask, with UV or visible light, and the unexposed areas of the layer are removed by treatment with a developer. Application of the photocurable layer to metal can also be carried out by electrodeposition. The exposed areas are polymeric through crosslinking and are therefore insoluble and remain on the support. Appropriate colouration produces visible images. Where the support is a metallized layer, the metal can, following exposure and development, be etched away at the unexposed areas or reinforced by electroplating. In this way it is possible to produce electronic circuits and photoresists. When used in image-forming materials the novel photoinitiators provide excellent performance in generating so called printout images, whereby a color change is induced due to irradiation. To form such print-out images different dyes and/or their leuco form are used and examples for such print out image systems can be fount e.g. in WO96/41240, EP706091, EP511403, U.S. Pat. Nos. 3,579,339 and 4,622,286.

The novel photoinitiator mixture is also suitable for a photopatternable composition for forming a dielectric layer of a multilayer layer circuit board produced by a sequential build-up process.

The invention, as described above, provides compositions for producing pigmented and non-pigmented paints and varnishes, powder coatings, printing inks, printing plates, adhesives, pressure-sensitive adhesives, dental compositions, gel coats, photoresists for electronics, electroplating resist, etch resist, both liquid and dry films, solder resist, as resists to manufacture color filters for a variety of display applications, to generate structures in the manufacturing processes of plasma-display panels (e.g. barrier rib, phosphor layer, electrode), electroluminescence displays and LCD (e.g. interlayer insulating layer, spacers, microlens array), for holographic data storage (HDS), as composition for encapsulating electrical and electronic components, for producing magnetic recording materials, micromechanical parts, waveguides, optical switches, plating masks, etch masks, colour proofing systems, glass fibre cable coatings, screen printing stencils, for producing three-dimensional objects by means of stereolithography, and as image recording material, for holographic recordings, microelectronic circuits, decolorizing materials, decolorizing materials for image recording materials, for image recording materials using microcapsules, as a photoresist material used for forming dielectric layers in a sequential build-up layer of a printed circuit board.

Substrates used for photographic information recordings include, for example, films of polyester, cellulose acetate or polymer-coated papers; substrates for offset printing formes are specially treated aluminium, substrates for producing printed circuits are copper-clad laminates, and substrates for producing integrated circuits are, for example, silicon wafers. The layer thickness of the photosensitive layer for photographic materials and offset printing forms is generally from about 0.5 µm to 10 µm, while for printed circuits it is from 0.1 µm to about 100 µm. Following the coating of the substrates, the solvent is removed, generally by drying, to leave a coat of the photoresist on the substrate.

Coating of the substrates can be carried out by applying to the substrate a liquid composition, a solution or a suspension. The choice of solvents and the concentration depend principally on the type of composition and on the coating technique. The solvent should be inert, i.e. it should not undergo a chemical reaction with the components and should be able to be removed again, after coating, in the course of drying. Examples of suitable solvents are ketones, ethers and esters, such as methyl ethyl ketone, isobutyl methyl ketone, cyclopentanone, cyclohexanone, N-methylpyrrolidone, dioxane, tetrahydrofuran, 2-methoxyethanol, 2-ethoxyethanol, 1-methoxy-2-propanol, 1,2-dimethoxyethane, ethyl acetate, n-butyl acetate, ethyl 3-ethoxypropionate, 2-methoxypropylacetate, methyl-3-methoxypropionate, 2-heptanone, 2-pentanone, and ethyl lactate.

The solution is applied uniformly to a substrate by means of known coating techniques, for example by printing, spin coating, dip coating, knife coating, curtain coating, brushing, spraying, especially by electrostatic spraying, and reverse-roll coating, and also by means of electrophoretic deposition. It is also possible to apply the photosensitive layer to a temporary, flexible support and then to coat the final substrate, for example a copper-clad circuit board, or a glass substrate by transferring the layer via lamination.

The quantity applied (coat thickness) and the nature of the substrate (layer support) are dependent on the desired field of application. The range of coat thicknesses generally comprises values from about 0.1 µm to more than 100 µm, for example 0.1 µm to 1 cm, preferably 0.5 µm to 1000 µm.

Following the coating of the substrates, the solvent is removed, generally by drying, to leave an essentially dry resist film of the photoresist on the substrate.

The photosensitivity of the novel compositions can extend in general from about 150 nm to 600 nm, for example 190-600 nm, (UV-vis region). Suitable radiation is present, for example, in sunlight or light from artificial light sources. Consequently, a large number of very different types of light sources are employed. Both point sources and arrays ("lamp carpets") are suitable. Examples are carbon arc lamps, xenon arc lamps, low-, medium-, high- and super high-pressure mercury lamps, possibly with metal halide dopes (metal-halogen lamps), microwave-stimulated metal vapour lamps, excimer lamps, superactinic fluorescent tubes, fluorescent lamps, argon incandescent lamps, electronic flashlights, photographic flood lamps, light emitting diodes (LED), electron beams and X-rays. The distance between the lamp and the substrate to be exposed in accordance with the invention may vary depending on the intended application and the type and output of lamp, and may be, for example, from 1 cm to 150 cm. Laser light sources, for example excimer lasers, such as $F_2$ excimer lasers at 157 nm exposure, KrF excimer lasers for exposure at 248 nm and ArF excimer lasers for exposure at 193 nm are also suitable. Lasers in the visible region can also be employed.

The term "imagewise" exposure includes both, exposure through a photomask comprising a predetermined pattern, for example a slide, a chromium mask, a stencil mask or a reticle, as well as exposure by means of a laser or light beam, which for example is moved under computer control over the surface of the coated substrate and in this way produces an image. Suitable UV laser exposure systems for the purpose are, for example, provided by Etec and Orbotech (DP-100™ DIRECT IMAGING SYSTEM). Other examples of laser light sources are, for example excimer lasers, such as $F_2$ excimer lasers at 157 nm exposure, KrF excimer lasers for exposure at 248 nm and ArF excimer lasers for exposure at 193 nm. Further suitable are solid state UV lasers (e.g. Gemini from ManiaBarco, DI-2050 from PENTAX) and violet laser diodes with 405 nm output (DI-2080, DI-PDP from PENTAX). Lasers in the visible region can also be employed. And the computer-controlled irradiation can also be achieved by electron beams. It is also possible to use masks made of liquid crystals that can be addressed pixel by pixel to generate digital images, as is, for example, described by A. Bertsch, J. Y. Jezequel, J. C. Andre in Journal of Photochemistry and Photobiology A: Chemistry 1997, 107, p. 275-281 and by K.-P. Nicolay in Offset Printing 1997, 6, p. 34-37.

Following the imagewise exposure of the material and prior to development, it may be advantageous to carry out thermal treatment for a short time. After the development a thermal post bake can be performed to harden the composition and to remove all traces of solvents. The temperatures employed are generally 50-250° C., preferably 80-220° C.; the duration of the thermal treatment is in general between 0.25 and 60 minutes.

The photocurable composition may additionally be used in a process for producing printing plates or photoresists as is described, for example, in DE4013358. In such a process the composition is exposed for a short time to visible light with a wavelength of at least 400 nm, without a mask, prior to, simultaneously with or following imagewise irradiation.

After the exposure and, if implemented, thermal treatment, the unexposed areas of the photosensitive coating are removed with a developer in a manner known per se.

As already mentioned, the novel compositions can be developed by aqueous alkalis or organic solvents. Particularly suitable aqueous-alkaline developer solutions are aqueous solutions of tetraalkylammonium hydroxides or of alkali metal silicates, phosphates, hydroxides and carbonates. Minor quantities of wetting agents and/or organic solvents may also be added, if desired, to these solutions. Examples of typical organic solvents, which may be added to the developer liquids in small quantities, are cyclohexanone, 2-ethoxyethanol, toluene, acetone and mixtures of such solvents. Depending on the substrate also solvents, e.g. organic solvents, can be used as developer, or, as mentioned above mixtures of aqueous alkalis with such solvents. Particularly useful solvents for solvent development include methanol, ethanol, 2-propanol, 1-propanol, butanol, diacetone alcohol, ethylene glycol monomethyl ether, ethylene glycol monoethyl ether, ethylene glycol mono-n-butyl ether, diethyleneglycol dimethyl ether, propyleneglycol monomethyl ether acetate, ethyl-3-ethoxypropionate, methyl-3-methoxypropionate, n-butyl acetate, benzyl alcohol, acetone, methyl ethyl ketone, cyclopentanone, cyclohexanone, 2-heptanone, 2-pentanone, epsilon-caprolactone, gamma-butylolactone, dimethylformamide, dimethylacetamide, hexamethyl-phosphoramide, ethyl lactate, methyl lactate, epsilon-caprolactam, and N-methyl-pyrrolidinone. Optionally, water can be added to these solvents up to a level at which still a clear solution is obtained and at which sufficient solubility of the unexposed areas of the light sensitive composition is maintained.

The invention therefore also provides a process for the photopolymerization of compounds containing ethylenically unsaturated double bonds, i.e. monomeric, oligomeric or polymeric compounds containing at least one ethylenically unsaturated double bond, which comprises adding to these compounds at least one photoinitiator mixture as described above and irradiating the resulting composition with electromagnetic radiation, in particular light of the wavelength 150 to 600 nm, in particular 190-600 nm, with electron beam, or with X-rays.

In other words, adding to these compounds compounds containing ethylenically unsaturated double bonds at least one photoinitiator mixture as described above and irradiating the resulting composition with electromagnetic radiation, in particular light of the wavelength 150 to 600 nm, in particular 190-600 nm, with electron beam, or with X-rays.

The invention further provides a coated substrate which is coated on at least one surface with a composition as described above, and describes a process for the photographic production of relief images, in which a coated substrate is subjected to imagewise exposure and then the unexposed portions are removed with a developer. Imagewise exposure may be effected by irradiating through a mask or by means of a laser or electron beam as already described above. Of particular advantage in this context is the laser beam exposure already mentioned above.

A further subject of the invention is a cured coating obtained by applying a composition according to claim 4 to a substrate and irradiating said coated substrate with electromagnetic radiation in the range from 150 to 600 nm, or with electron beam or with X-rays.

The examples which follow illustrate the invention in more detail. Parts and percentages are, as in the remainder of the description and in the claims, by weight, unless stated otherwise. Where alkyl radicals having more than three carbon atoms are referred to in the following examples without any mention of specific isomers, the n-isomers are meant in each case.

The photoinitiator mixtures of the invention have a good thermal stability, low volatility, good storage stability and high solubility, and are also suitable for photopolymerisations in the presence of air (oxygen). Further, they cause only low yellowing in the compositions after photopolymerization, as well as an excellent resolution in resist applications, in particular color filters and high curing speeds in particular in printing ink applications.

The examples which follow illustrate the invention in more detail. Parts and percentages are, as in the remainder of the description and in the claims, by weight, unless stated otherwise. Where alkyl radicals having more than three carbon atoms are referred to in the following examples without any mention of specific isomers, the n-isomers are meant in each case.

EXAMPLE 1

Synthesis of

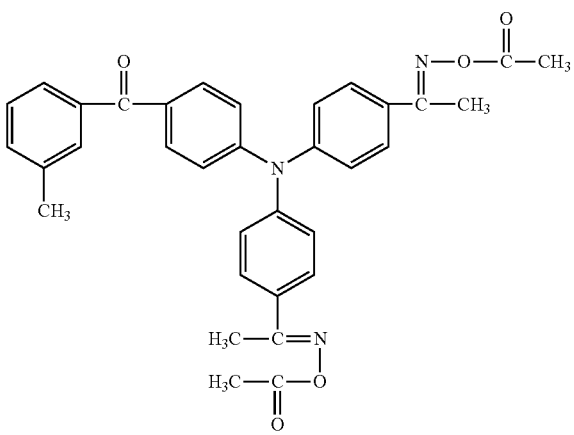 [SMILES: CC(=O)O/N=C(\C)c1ccc(N(c2ccc(C(=O)c3cccc(C)c3)cc2)c2ccc(/C(C)=N/OC(C)=O)cc2)cc1]

[compound of formula I; $R_1=R_2=CH_3$, $R_7=$phenyl substituted by $CH_3$]

1.a. 1-(4-{(4-Acetyl-phenyl)-[4-(3-methyl-benzoyl)-phenyl]-amino}-phenyl)-ethanone To triphenylamine (5.00 g) in $CH_2Cl_2$ (80 mL) are added $AlCl_3$ (2.89 g) and m-toluoyl chloride (3.15 g) at 0° C. After stirring overnight at room temperature, $AlCl_3$ (5.98 g) and acetyl chloride (3.36 g) are further added at 0° C. After the mixture is stirred at room temperature overnight, the reaction mixture is poured into ice-water, and the crude product is extracted twice with $CH_2Cl_2$. The combined organic layer is washed with $H_2O$ and brine, dried over $MgSO_4$, and concentrated to give the product. The structure of the product, which is obtained as a yellow solid, is confirmed by the $^1$H-NMR spectrum ($CDCl_3$). δ [ppm]: 2.44 (s, 3H), 2.59 (s, 6H), 7.16-7.25 (m, 6H), 7.34-7.42 (m, 2H), 7.58 (d, 1H), 7.63 (s, 1H), 7.79 (d, 2H), 7.92 (d, 4H).

1.b. 1-{4-([4-{1-(Acetoxyimino)-ethyl}-phenyl]-[4-(3-methyl-benzoyl)-phenyl]-amino)-phenyl}-ethanone oxime O-acetate The ketone 1.a is transformed to the corresponding oxime acetate 1.b, which is isolated as a yellow solid, according to the procedure described in WO02-100903. The structure is confirmed by the $^1$H-NMR spectrum ($CDCl_3$). δ [ppm]: 2.27 (s, 6H), 2.38 (s, 6H), 2.43 (s, 3H), 7.11 (d, 2H), 7.16 (d, 4H), 7.34-7.40 (m, 2H), 7.56 (d, 2H), 7.61 (s, 1H), 7.70 (d, 4H), 7.75 (d, 2H).

EXAMPLES 2-12

The compounds of examples 2-12 are prepared according to the method as given in example 1 employing the appropriate educts. The compounds and their physical data are listed in table 1 below.

TABLE 1

| example | Compound | physical data |
|---|---|---|
| 2 | 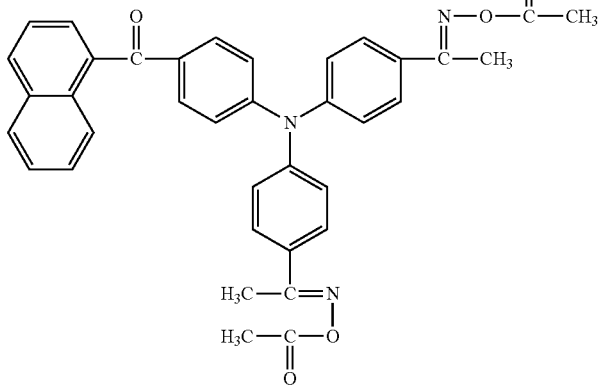<br>formula I,<br>$R_1 = R_2 = CH_3$;<br>$R_7$ = napthyl | Yellow solid<br>$^1$H-NMR (CDCl$_3$) δ [ppm]: 2.27 (s, 6H), 2.38 (s, 6H), 7.06 (d, 2H), 7.15 (d, 4H), 7.48-7.54 (m, 3H), 7.58 (d, 1H), 7.69 (d, 4H), 7.77 (d, 2H), 7.91 (m, 1H), 7.98 (d, 1H), 8.07 (m, 1H). |
| 3 | 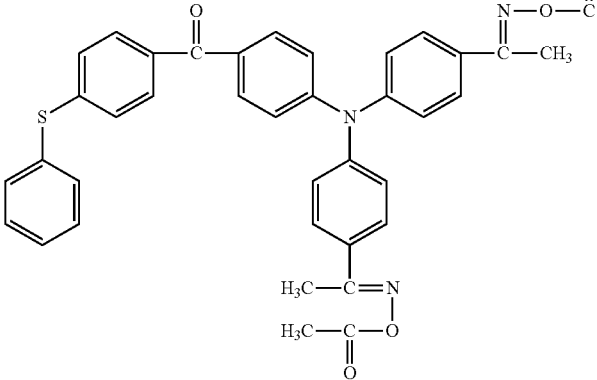<br>formula I,<br>$R_1 = R_2 = CH_3$;<br>$R_7$ = phenyl substituted by $SR_4$;<br>$R_4$ = phenyl | Yellow solid<br>$^1$H-NMR (CDCl$_3$) δ [ppm]: 2.27 (s, 6H), 2.38 (s, 6H), 7.08-7.18 (m, 7H), 7.24-7.28 (m, 2H), 7.38-7.42 (m, 2H), 7.50-7.54 (m, 2H), 7.68-7.74 (m, 8H). |
| 4 | 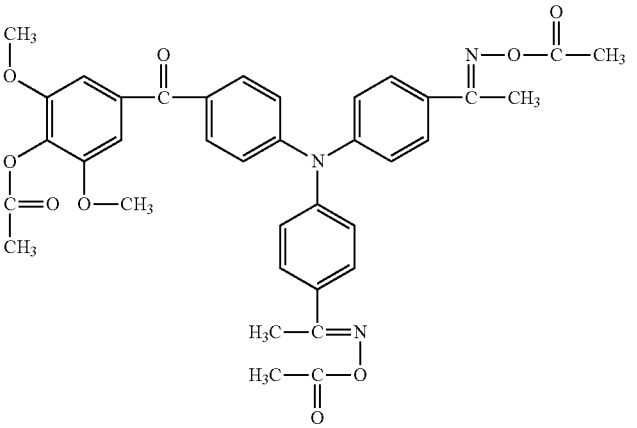<br>formula I,<br>$R_1 = R_2 = CH_3$;<br>$R_7$ = phenyl substituted by $OR_3$;<br>$R_3 = C_1$alkanoyl and $CH_3$ | Yellow solid<br>$^1$H-NMR (CDCl$_3$) δ [ppm]: 2.27 (s, 6H), 2.37 (s, 3H), 2.39 (s, 6H), 3.87 (s, 6H), 7.06 (s, 2H), 7.12 (d, 2H), 7.16 (d, 4H), 7.71 (d, 4H), 7.79 (d, 2H). |

TABLE 1-continued

| example | Compound | physical data |
|---|---|---|
| 5 | formula I, $R_1 = R_2 = CH_3$; $R_7$ = phenyl substituted by halogen | Yellow solid <br> $^1$H-NMR (CDCl$_3$) δ [ppm]: 2.27 (s, 6H), 2.39 (s, 6H), 7.11 (d, 2H), 7.16 (d, 4H), 7.61-7.74 (m, 10H). |
| 6 | formula I, $R_1 = R_2 = CH_3$; $R_7$ = phenyl substituted by halogen | Yellow solid <br> $^1$H-NMR (CDCl$_3$) δ [ppm]: 2.27 (s, 6H), 2.38 (s, 6H), 7.05 (d, 2H), 7.15 (d, 4H), 7.34 (d, 2H), 7.38-7.43 (m, 1H), 7.64 (d, 1H), 7.66-7.71 (m, 6H). |
| 7 | formula I, $R_1 = R_2 = CH_3$; $R_7$ = phenyl substituted by CH$_3$ | Yellow solid <br> $^1$H-NMR (CDCl$_3$) δ [ppm]: 2.27 (s, 6H), 2.38 (s, 6H), 2.44 (s, 3H), 7.11 (d, 2H), 7.15 (d, 4H), 7.29 (d, 2H), 7.68-7.76 (m, 8H). |

TABLE 1-continued

| example | Compound | physical data |
|---|---|---|
| 8 | formula I, R₁ = R₂ = CH₃; R₇ = phenyl substituted by CH₃ | Yellow solid<br>$^1$H-NMR (CDCl$_3$) δ [ppm]: 2.27 (s, 6H), 2.35 (s, 3H), 2.38 (s, 6H), 7.06 (d, 2H), 7.15 (d, 4H), 7.22-7.40 (m, 4H), 7.66-7.72 (m, 6H). |
| 9 | formula I, R₁ = R₂ = CH₃; R₇ = thienyl | Yellow solid<br>$^1$H-NMR (CDCl$_3$) δ [ppm]: 2.27 (s, 6H), 2.39 (s, 6H), 7.12-7.18 (m, 7H), 7.68-7.72 (m, 6H), 7.83 (d, 2H). |
| 10 | formula I, R₁ = R₂ = CH₃; R₇ = phenyl substituted by NR₅R₆; R₅ and R₆ form a heterocyclic ring | Yellow solid<br>$^1$H-NMR (CDCl$_3$) δ [ppm]: 2.27 (s, 6H), 2.39 (s, 6H), 7.16-7.22 (m, 6H), 7.32 (t, 2H), 7.44 (t, 2H), 7.53 (d, 2H), 7.70-7.76 (m, 6H), 7.85 (d, 2H), 8.06 (d, 2H), 8.15 (d, 2H). |

TABLE 1-continued

| example | Compound | physical data |
|---|---|---|
| 11 | formula I,<br>$R_1 = CH_3$; $R_2 = C_4H_9$;<br>$R_7$ = phenyl substituted by $CH_3$ | Yellow solid<br>$^1$H-NMR (CDCl$_3$) δ [ppm]: 0.98 (d, 12H), 1.98 (quint, 2H), 2.26 (s, 6H), 2.44 (s, 3H), 2.77 (d, 4H), 7.10-7.20 (m, 6H), 7.26-7.31 (m, 2H), 7.64-7.77 (m, 8H). |
| 12 | formula I,<br>$R_1 = CH_3$; $R_2 = C_7H_{15}$;<br>$R_7$ = phenyl substituted by $CH_3$ | Yellow oil<br>$^1$H-NMR (CDCl$_3$) δ [ppm]: 0.89 (t, 6H), 1.20-1.44 (m, 16H), 1.54-1.64 (m, 4H), 2.26 (s, 6H), 2.43 (s, 3H), 2.82 (t, 4H), 7.08-7.19 (m, 6H), 7.35-7.41 (m, 2H), 7.54-7.59 (m, 1H), 7.60-7.63 (m, 1H), 7.67 (d, 4H), 7.75 (d, 2H). |
| 13 | formula I,<br>$R_1 = R_2 = CH_3$;<br>$R_7$ = phenyl substituted by two halogens | Yellow solid<br>$^1$H NMR (CDCl$_3$) δ [ppm]: 2.27 (s, 6H), 2.38 (s, 6H), 7.06 (d, 2H), 7.15 (d, 4H), 7.30-7.38 (m, 2H), 7.48 (d, 1H), 7.64-7.73 (m, 6H). |

TABLE 1-continued

| example | Compound | physical data |
|---|---|---|
| 14 | 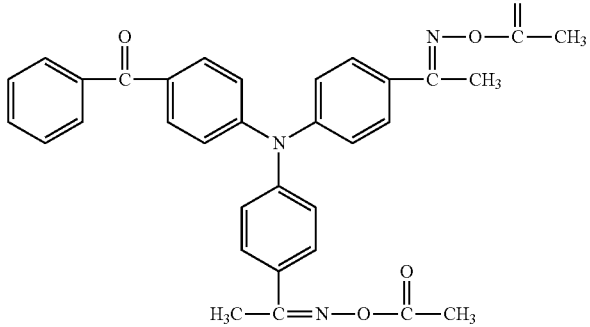

formula I,
$R_1 = R_2 = CH_3$;
$R_7 = $ phenyl | Yellow solid
$^1$H NMR (CDCl$_3$) δ [ppm]: 2.27 (s, 6H), 2.38 (S, 6H), 7.11 (d, 2H), 7.16 (d, 4H), 7.49 (t, 2H), 7.58 (t, 1H), 7.70 (d, 4H), 7.75 (d, 2H), 7.79 (d, 2H). |
| 15 | 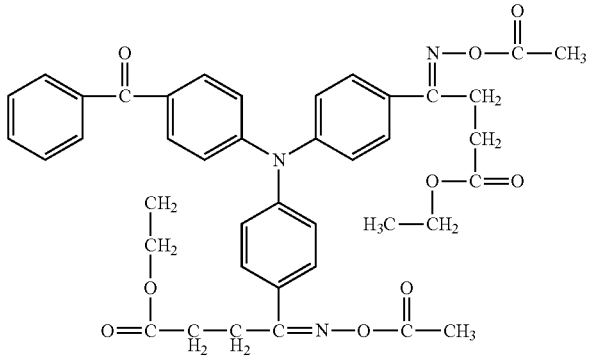

formula I,
$R_1 = CH_3$;
$R_2 = $ alkyl substituted by COOR$_3$;
$R_3 = $ ethyl; $R_7 = $ phenyl | Yellow solid
$^1$H NMR (CDCl$_3$) δ [ppm]: 1.26 (t, 6H), 2.27 (s, 6H), 2.60 (t, 4H), 3.16 (t, 4H), 4.15 (q, 4H), 7.10-7.20 (m, 6H), 7.49 (t, 2H), 7.56-7.62 (m, 1H), 7.68 (d, 4H), 7.74-7.82 (m, 4H). |
| 16 | 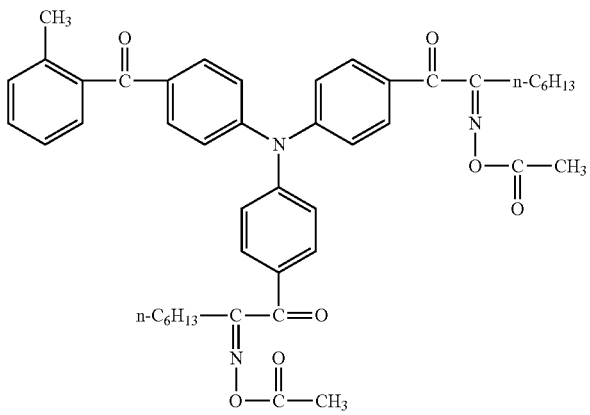

formula I',
$R_1 = CH_3$; $R_2 = $ n-C$_6$H$_{13}$;
$R_7 = $ phenyl substituted by CH$_3$. | Yellow liquid
$^1$H NMR (CDCl$_3$) δ [ppm]: 0.87 (t, 6H), 1.24-1.42 (m, 12H), 1.55 (quint, 4H), 2.26 (s, 6H), 2.37 (s, 3H), 2.79 (t, 4H), 7.18 (d, 6H), 7.24-7.42 (m, 4H), 7.77 (d, 2H), 8.06 (d, 4H). |

APPLICATION EXAMPLES

The following examples are performed in a blue flexo ink with the following composition:

15.0 wt.-% hexafunctional polyester acrylate (Ebecryl 450, provided by Cytec)

20.0 wt.-% tetrafunctional polyester acrylate (Ebecryl 812, provided by Cytec)

15.0 wt.-% amine modified polyether acrylate (Ebecryl 83, provided by Cytec)

33.3 wt.-% monofunctional acrylate (Ebecryl 160, provided by Cytec)

0.7 wt.-% silicone additive (DC57, provided by Dow Corning)

16.0 wt.-% pigment (IRGALITE® Blue GLO, provided by Ciba Inc.)

The formulations to be tested are applied using a Prufbau machine onto a corona treated polymeric white foil. The samples are exposed to a medium pressure mercury lamp or a gallium-doted lamp with a power ranging from 80 to 200 W/cm under air or nitrogen at different belt speeds.

Polymerization efficiency is assessed using:
either a REL complete curing tester immediately after the irradiation. In this test, an aluminum cylinder over which a fabric is stretched is placed on the printed sample and rotated once around its own axis under a pressure of 220 g/cm² in the course of 10 seconds. If visible damage to the sample is caused by this procedure, the printing ink has not been sufficiently through cured;
or by rubbing the surface with a Tela tissue. In this test, the transfer of the ink from the exposed surface to the tissue characterizes a poor curing of the ink surface.

Reactivity is measured by the cure speed defined as the maximum belt speed required to get a proper cure at a constant light intensity.

The following compounds are used in the examples:

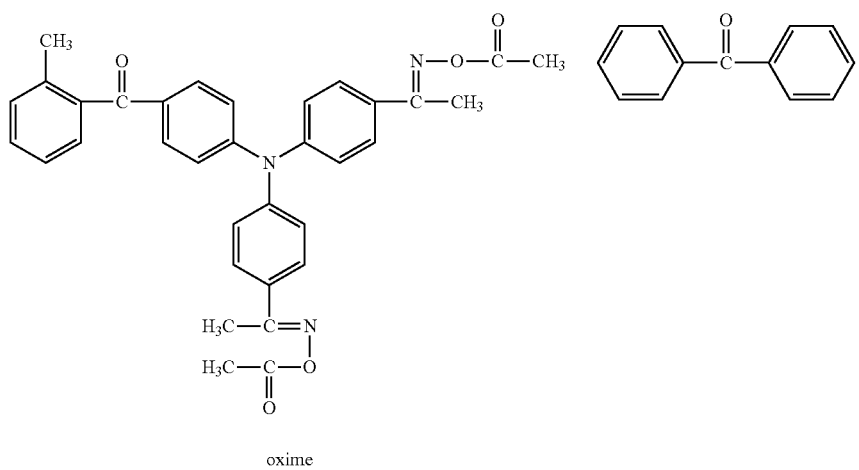
oxime

BP-1

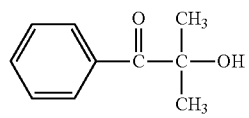

HK-1

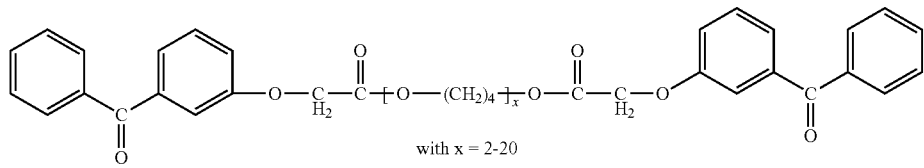
with x = 2-20

BP-2

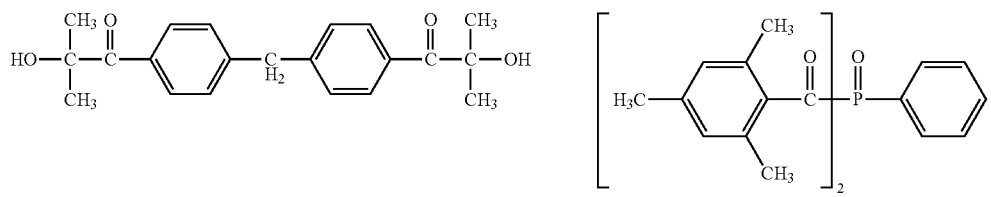

HK-2

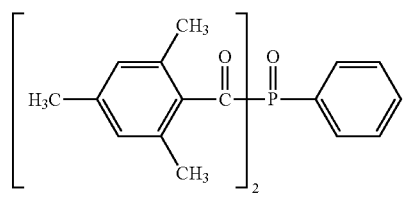

BPO-1

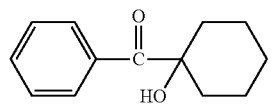

HK-3

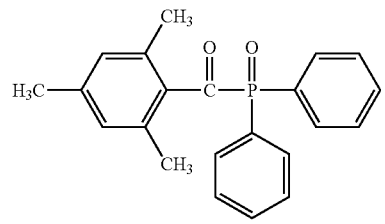

MPO-1

KS-1

[Chemical structure: benzophenone-thioether-ketone-sulfonyl-tolyl compound with formula containing C(=O), S, C(CH3)2, SO2, CH3 groups]

EDB

[Chemical structure: C2H5O—C(=O)—phenyl—N(CH3)2, ethyl 4-(dimethylamino)benzoate]

mixture-1: 5 parts BPO-1
17 parts MPO-1
78 parts HK-1 mixture-2: liquid blend of
2,4,6-trimethylbenzoylphenylphosphine oxide
alpha hydroxyketone
2,4,6-trimethylbenzophenone
4-methylbenzophenone
(= ESACURE® KTO 46)

Example A1

Mixtures with Compounds of the Formula (HK)

TABLE A1

Cure speed measured by REL of HK-2 and blend HK-2/oxime in the presence of HK-1 in a blue flexo ink; Gallium lamp, cold mirrors, 150 W/cm under nitrogen, white PEC foil corona treated

| 4% HK-1 + Photoinitiator | Cure speed (m/min) |
|---|---|
| 4% HK-2 | 140 |
| 4% blend HK-2/oxime (ratio 92:8) | 160 |

Example A2

Mixture with Compounds of the Formula (HK) and (BP)

TABLE A2

Cure speed measured by REL of HK-3/BP-1 and a blend HK-3/BP-1/oxime in a blue flexo ink; Hg lamp, cold mirrors, 200 W/cm under nitrogen 700 ppm $O_2$, white PEC foil corona treated

| Photoinitiator | Cure speed (m/min) |
|---|---|
| 5% HK-3/BP-1 (ratio 1:1) | 80 |
| 5% blend [HK-3/BP-1 (ratio 1:1)]/oxime (ratio [92]:8) | 150 |

Example A3

Mixture with Compounds of the Formula (BP)

TABLE A3

Cure speed measured by REL and rubbing of BP-2 and blend BP-2/oxime with 2% EDB in a blue flexo ink; Hg lamp, cold mirrors, 200 W/cm under air, white PEC foil

| Photoinitiator | Cure speed (m/min) REL | Cure speed (m/min) Tissue Rub |
|---|---|---|
| 10% BP-2 and 2% EDB | 50 | 30 |
| 10% of a blend BP-2/oxime (92/8) and 2% EDB | 100-110 | 50 |

Example A4

Mixture with Compound of the Formula (BPO)

TABLE A4

Cure speed measured by REL of BPO-1 and blend BPO-1/oxime in a blue flexo ink; Hg lamp, cold mirrors, 80 W/cm under air, white PEC foil

| Photoinitiator | Curing speed (m/min) |
|---|---|
| 4% BPO-1 | 90 |
| 4% Blend BPO-1/oxime (ratio 92:8) | 120 |

Example A5

Mixture with Compound of the Formula (HK) and (MPO)

TABLE A5

Cure speed measured by REL of MPO-1 and blend MPO-1/oxime in a blue flexo ink; Ga lamp, cold mirrors, 150 W/cm under nitrogen, white PEC foil corona treated

| 4% HK-1 + Photoinitiator | Cure speed (m/min) |
|---|---|
| 4% MPO-1 | 40 |
| 4% Blend MPO-1/oxime (ratio 92:8) | 60 |

Example A6

Mixture with Compound of the Formula (HK) and (BPO)

TABLE A6

Cure speed measured by REL of BPO-1 and blend BPO-1/oxime with HK-1 in a blue flexo ink; Ga lamp, cold mirrors, 200 W/cm under inert atmosphere

| 4% HK-1 + Photoinitiator | Cure speed (m/min) |
|---|---|
| 4% BPO-1 | 80 |
| 4% Blend BPO-1/oxime (ratio 92.5:7.5) | 120 |

Example A7

Mixture with Compound of the Formula (KS)

TABLE A7

Cure speed measured by REL of KS-1 and blend KS-1/oxime with and without EDB in a blue flexo ink; Hg lamp, cold mirrors, 200 W/cm under air, white PEC

| Photoinitiator | Curing speed (m/min) REL |
|---|---|
| 4% KS-1 | 50 |
| 4% Blend KS-1/oxime (ratio 92:8) | 70 |
| 4% KS-1 + 2% EDB | 110 |
| 4% of a blend KS-1/oxime (ratio 92:8) + 2% EDB | 140-150 |

Example A8

Mixture with Compound of the Formula (BPO), Curing Via LED

TABLE A8

Cure speed measured by rubbing of BPO-1 and BPO-1/oxime (92:8) in a blue flexo ink; LED characteristics: Loctite ® CureJet ™ 405 LED, Typical Output: 1.1 Watt/cm$^2$, substrate placed at 23 mm distance from the lamp. Spectral Output Range is 390-420 nm with primary peak at 405 nm, white PVC foil.

| Photoinitiator | Curing time (s) |
|---|---|
| 3% BPO-1 | 35 |
| 3% Blend BPO-1/oxime, ratio 92/8 | 30 |
| 2% Blend BPO-1/oxime, ratio 92/8 | 35 |

Example A9

Curing of an Adhesive Formulation

A UV curable acrylic adhesive formulation is prepared comprising
50% aliphatic urethane acrylate (Ebecryl 270 from Cytec),
25% isobornyl acrylate (IBOA),
25% trimethylolpropane triacrylate (TMPTA), and
photoinitiator as indicated in the table A9

One drop of adhesive is applied to a glass slide, then covered at an angle of approx 45° with a second glass slide and subsequently irradiated with the UV LED source at a constant distance of 150 mm. Determined is the fixture time. The fixture time is defined as the time of UV exposure needed to prevent two bonded glass slides from relative movement under light shear pressure.

TABLE A9

LED characteristics: Loctite ® CureJet ™ 405 LED, Typical Output: 1.1 Watt/cm2, substrate placed at 23 mm distance from the lamp. Spectral Output Range is 390-420 nm with primary peak at 405 nm

| Photoinitiator | UV Fixture time (s) |
|---|---|
| 1.0% mixture-1 | 7.0 |
| 1.0% mixture-1 0.1% oxime | 5.0 |
| 1.0% mixture-2 | 4.5 |
| 1.0% mixture-2 0.1% oxime | 3.0 |

As all examples clearly demonstrate, the addition of a small amount of the oxime ester compound of formula I enhances the performance of the photoinitiators of the formulae (HK), (MPO), (BPO), (BP) and (KS) considerably.

The invention claimed is:
1. Photoinitiator mixture comprising
    (i) at least one compound selected from the group consisting of alpha-hydroxy ketones, monoacylphosphine oxides, bisacylphosphine oxides, ketosulfones, benzil ketals, benzoin ether, phenylglyoxylates, borates and titanocenes; and
    (ii) at least one compound of the formula (I) and (I')

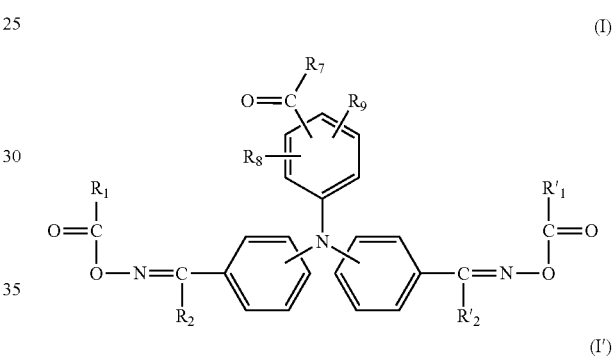

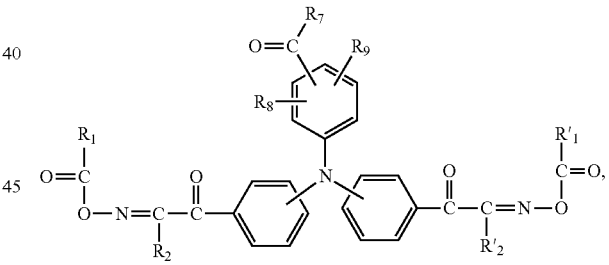

wherein
$R_1$ and $R'_1$ independently of one another are hydrogen, $C_3$-$C_8$cycloalkyl or $C_1$-$C_{12}$alkyl which is unsubstituted or substituted by one or more halogen, phenyl and/or CN; or
$R_1$ and $R'_1$ are $C_2$-$C_5$alkenyl; or
$R_1$ and $R'_1$ are phenyl which is unsubstituted or substituted by one or more $C_1$-$C_6$alkyl, halogen, CN, $OR_3$, $SR_4$ and/or $NR_5R_6$; or
$R_1$ and $R'_1$ are $C_1$-$C_8$alkoxy, benzyloxy; or phenoxy which is unsubstituted or substituted by one or more $C_1$-$C_6$alkyl and/or halogen;
$R_2$ and $R_2'$ independently of one another are hydrogen; unsubstituted $C_1$-$C_{20}$alkyl or $C_1$-$C_{20}$alkyl substituted by one or more halogen, $OR_3$, $SR_4$, $C_1$-$C_{20}$heteroaryl, $C_8$-$C_{20}$phenoxycarbonyl, $C_1$-$C_{20}$heteroaryloxycarbonyl, $NR_5R_6$, $COOR_3$, $CONR_5R_6$,

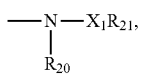

phenyl and/or by phenyl which is substituted by $OR_3$, $SR_4$ and/or $NR_5R_6$, wherein the unsubstituted or substituted $C_1$-$C_{20}$alkyl optionally contains one or more C—C multiple bonds; or $R_2$ and $R_2'$ are $NR_5R_6$,

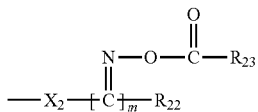

or $C_3$-$C_{20}$cycloalkyl;

or are $C_2$-$C_{20}$alkyl which is interrupted by one or more O and which optionally is substituted by one or more halogen, $OR_3$, phenyl and/or phenyl substituted by $OR_3$, $SR_4$ and/or $NR_5R_6$; or $R_2$ and $R_2'$ are phenyl which is unsubstituted or substituted by one or more $C_1$-$C_6$alkyl, phenyl, halogen, $OR_3$, $SR_4$ and/or $NR_5R_6$; or $R_2$ and $R_2'$ are $C_2$-$C_{20}$alkanoyl or benzoyl which is unsubstituted or substituted by one or more $C_1$-$C_6$alkyl, phenyl, $OR_3$, $SR_4$ and/or $NR_5R_6$; or $R_2$ and $R_2'$ are $C_2$-$C_{12}$alkoxycarbonyl which is optionally interrupted by one or more O and/or optionally substituted by one or more hydroxyl groups; or $R_2$ and $R_2'$ are phenoxycarbonyl which is unsubstituted or substituted by $C_1$-$C_6$alkyl, halogen, phenyl, $OR_3$, $SR_4$ and/or $NR_5R_6$; or $R_2$ and $R_2'$ are CN, $CONR_5R_6$, $NO_2$, $S(O)_m$—$C_1$-$C_6$alkyl; $S(O)_m$-phenyl which optionally is substituted by $C_1$-$C_{12}$alkyl or $SO_2$—$C_1$-$C_6$alkyl; or are $SO_2O$-phenyl which optionally is substituted by $C_1$-$C_{12}$alkyl;

or are diphenyl phosphinoyl or di-($C_1$-$C_4$alkoxy)-phosphinoyl; or $R_2$ and $R_2'$ are

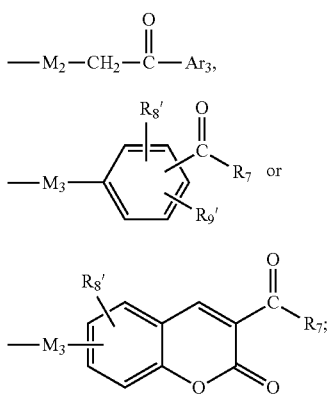

m is 1 or 2;

$Ar_3$ is phenyl, naphthyl or coumarinyl, each of which is substituted once or more times by halogen, $C_1$-$C_{12}$alkyl, $C_3$-$C_8$cycloalkyl, benzyl and/or phenoxycarbonyl; or each of which is substituted by phenyl or by phenyl which is substituted by one or more $OR_3$, $SR_4$ and/or $NR_5R_6$;

or each of which is substituted by $C_2$-$C_{12}$alkoxycarbonyl optionally interrupted by one or more O and/or optionally substituted by one or more hydroxyl groups; or each of which is substituted by $OR_3$, $SR_4$, $SOR_4$, $SO_2R_4$ and/or $NR_5R_6$;

$M_2$ is a direct bond, cyclohexylene or $C_1$-$C_{10}$alkylene or $C_1$-$C_{10}$alkylene-X—, which $C_1$-$C_{10}$alkylene or $C_1$-$C_{10}$alkylene-X— is optionally interrupted by one or more O and/or optionally substituted by one or more halogen, $OR_3$, phenyl or phenyl substituted by $OR_3$, $SR_4$ and/or $NR_5R_6$; or $M_2$ is phenylene, naphthylene or phenylene-X—, each of which is unsubstituted or substituted by one or more $C_1$-$C_6$alkyl, phenyl, halogen, $OR_3$, $SR_4$ and/or $NR_5R_6$; or $M_2$ is $C_1$-$C_{10}$alkylene-C(O)—X—, $C_1$-$C_{10}$alkylene-X—C(O)—, phenylene-C(O)—X— or $C_1$-$C_{10}$alkylene-phenylene-X—;

$M_3$ is a direct bond, cyclohexylene, $C_1$-$C_{10}$alkylene or $C_1$-$C_{10}$alkylene-X—, which $C_1$-$C_{10}$alkylene or $C_1$-$C_{10}$alkylene-X— is optionally interrupted by one or more O and/or optionally substituted by one or more halogen, $OR_3$, phenyl or phenyl substituted by $OR_3$, $SR_4$ and/or $NR_5R_6$; or $M_3$ is phenylene, naphthylene or phenylene-X—, each of which is unsubstituted or substituted by one or more $C_1$-$C_6$alkyl, phenyl, halogen, $OR_3$, $SR_4$ and/or $NR_5R_6$; or $M_3$ is $C_1$-$C_{10}$alkylene-C(O)—X—, $C_1$-$C_{10}$alkylene-X—C(O)—, phenylene-C(O)—X—, $C_1$-$C_{10}$alkylene-phenylene-X— or phenylene-(CO)-phenylene;

X is O, S or $NR_5$;

$X_1$ is O, S, SO or $SO_2$;

$X_2$ is a direct bond, $C_1$-$C_{20}$alkylene which optionally is interrupted by O, CO or $NR_5$, and which uninterrupted or interrupted $C_1$-$C_{20}$alkylene is unsubstituted or substituted by one or more halogen, $OR_3$, $COOR_3$, $NR_5R_6$, $C_1$-$C_{20}$heteroaryl, $C_1$-$C_{20}$heteroaryl-(CO)O, $C_1$-$C_{20}$heteroaryl-S, $CONR_5R_6$,

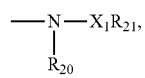

phenyl or by phenyl substituted by halogen, $C_1$-$C_{20}$alkyl, $C_1$-$C_4$haloalkyl, $SR_4$, $OR_3$, or $NR_5R_6$, and which unsubstituted or substituted, interrupted or non-interrupted $C_1$-$C_{20}$alkylene optionally contains one or more C—C multiple bonds;

$R_3$ is hydrogen, $C_1$-$C_{20}$alkyl or phenyl-$C_1$-$C_3$alkyl; or $R_3$ is $C_1$-$C_{20}$alkyl which is substituted by OH, SH, —CN, $C_3$-$C_6$alkenoxy, $OCH_2CH_2CN$, $OCH_2CH_2(CO)O(C_1$-$C_4$alkyl), $O(CO)$—$(C_1$-$C_4$alkyl), $O(CO)$-phenyl, $(CO)OH$ and/or $(CO)O(C_1$-$C_4$alkyl); or $R_3$ is $C_2$-$C_{20}$alkyl which is interrupted by one or more O; or $R_3$ is $(CH_2CH_2O)_{n+1}H$, $(CH_2CH_2O)_n(CO)$—$(C_1$-$C_8$alkyl), $C_1$-$C_8$alkanoyl, $C_2$-$C_{12}$alkenyl, $C_3$-$C_6$alkenoyl or $C_3$-$C_{20}$cycloalkyl which optionally is interrupted by O, S, CO, $NR_5$; or $R_3$ is benzoyl which is unsubstituted or substituted by one or more $C_1$-$C_6$alkyl, halogen, OH and/or $C_1$-$C_4$alkoxy; or $R_3$ is phenyl, naphthyl or $C_1$-$C_{20}$heteroaryl, each of which is unsubstituted or substituted by halogen, OH, $C_1$-$C_{12}$alkyl, $C_1$-$C_{12}$alkoxy, CN, $NO_2$, phenyl-$C_1$-$C_3$alkyloxy, phenoxy, $C_1$-$C_{12}$alkylsulfanyl, phenylsulfanyl, $N(C_1$-$C_{12}$alkyl$)_2$, diphenylamino and/or

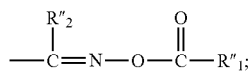

n is 1-20;

$R_4$ is hydrogen, $C_1$-$C_{20}$alkyl, $C_2$-$C_{12}$alkenyl, $C_3$-$C_{20}$cycloalkyl, phenyl-$C_1$-$C_3$alkyl, wherein the $C_1$-$C_{20}$alkyl, $C_2$-$C_{12}$alkenyl, $C_3$-$C_{20}$cycloalkyl, phenyl-$C_1$-$C_3$alkyl optionally is interrupted by O, S, CO, $NR_5$; or $R_4$ is $C_1$-$C_8$alkyl which is substituted by OH, SH, CN, $C_3$-$C_6$alkenoxy, $OCH_2CH_2CN$, $OCH_2CH_2(CO)O(C_1$-$C_4$alkyl), $O(CO)$—($C_1$-$C_4$alkyl), $O(CO)$-phenyl, $(CO)OH$ or $(CO)O(C_1$-$C_4$alkyl); or $R_4$ is $(CH_2CH_2O)_{n+1}H$, $(CH_2CH_2O)_n(CO)$—($C_1$-$C_8$alkyl), $C_1$-$C_8$alkanoyl, $C_2$-$C_{12}$alkenyl, $C_3$-$C_6$alkenoyl; or $R_4$ is benzoyl which is unsubstituted or substituted by one or more $C_1$-$C_6$alkyl, halogen, —OH, $C_1$-$C_4$alkoxy or $C_1$-$C_4$alkylsulfanyl; or $R_4$ is phenyl, naphthyl or $C_1$-$C_{20}$heteroaryl, each of which is unsubstituted or substituted by halogen, $C_1$-$C_{12}$alkyl, $C_1$-$C_{12}$alkoxy, CN, $NO_2$, phenyl-$C_1$-$C_3$alkyloxy, phenoxy, $C_1$-$C_{12}$alkylsulfanyl, phenylsulfanyl, $N(C_1$-$C_{12}$alkyl)$_2$, diphenylamino, $(CO)O(C_1$-$C_8$alkyl), $(CO)$—$C_1$-$C_8$alkyl, $(CO)N(C_1$-$C_8$alkyl)$_2$ or

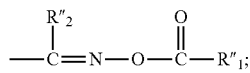

$R_5$ and $R_6$ independently of each other are hydrogen, $C_1$-$C_{20}$alkyl, $C_2$-$C_4$hydroxyalkyl, $C_2$-$C_{10}$alkoxyalkyl, $C_2$-$C_5$alkenyl, $C_3$-$C_{20}$cycloalkyl, phenyl-$C_1$-$C_3$alkyl, $C_1$-$C_8$alkanoyl, $C_3$-$C_{12}$alkenoyl, benzoyl; or $R_5$ and $R_6$ are phenyl, naphthyl or $C_1$-$C_{20}$heteroaryl, each of which is unsubstituted or substituted by $C_1$-$C_{12}$alkyl, benzoyl or $C_1$-$C_{12}$alkoxy; or $R_5$ and $R_6$ together with the N-atom to which they are attached form a 5- or 6-membered saturated or unsaturated ring which optionally is interrupted by O, S or $NR_3$, and which ring is unsubstituted or substituted by one or more $C_1$-$C_{20}$alkyl, $C_1$-$C_{20}$alkoxy, =O, $SR_4$, $OR_3$ or $NR_{17}R_{18}$, $(CO)R_{19}$, $NO_2$, halogen, $C_1$-$C_4$haloalkyl, CN, phenyl,

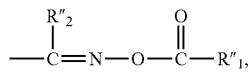

or by $C_3$-$C_{20}$cycloalkyl which optionally is interrupted by O, S, CO or $NR_3$; or $R_5$ and $R_6$ together with the N-atom to which they are attached form a heteroaromatic ring system, which heteroaromatic ring system is unsubstituted or substituted by one or more $C_1$-$C_{20}$alkyl, $C_1$-$C_4$haloalkyl, $C_1$-$C_{20}$alkoxy, =O, $SR_4$, $OR_3$, $NR_{17}R_{18}$, $(CO)R_{19}$,

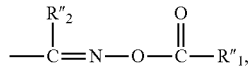

halogen, $NO_2$, CN, phenyl or by $C_3$-$C_{20}$cycloalkyl which optionally is interrupted by O, S, CO or $NR_3$;

$R''_1$ has one of the meanings as given for $R_1$;

$R''_2$ has one of the meanings as given for $R_2$;

$R_7$ is hydrogen, $C_1$-$C_{20}$alkyl; $C_1$-$C_8$alkyl which is substituted by halogen, phenyl, OH, SH, CN, $C_3$-$C_6$alkenoxy, $OCH_2CH_2CN$, $OCH_2CH_2(CO)O(C_1$-$C_4$alkyl), $O(CO)$—($C_1$-$C_4$alkyl), $O(CO)$-phenyl, $(CO)OH$ or $(CO)O(C_1$-$C_4$alkyl); or $R_7$ is $C_2$-$C_{12}$alkyl which is interrupted by one or more O; or $R_7$ is $(CH_2CH_2O)_{n+1}H$, $(CH_2CH_2O)_n(CO)$—($C_1$-$C_8$alkyl), $C_2$-$C_{12}$alkenyl or $C_3$-$C_8$cycloalkyl; or $R_7$ is phenyl, biphenylyl, naphthyl or $C_1$-$C_{20}$heteroaryl, each of which optionally is substituted by one or more $C_1$-$C_{20}$alkyl, halogen, $C_1$-$C_{12}$haloalkyl, CN, $NO_2$, $OR_3$, $SR_4$, $SOR_4$, $SO_2R_4$ or $NR_5R_6$, wherein the substituents $OR_3$, $SR_4$ or $NR_5R_6$ optionally form 5- or 6-membered rings via the radicals $R_3$, $R_4$, $R_5$ and/or $R_6$ with one of the carbon atoms of the phenyl, biphenylyl, naphthyl or $C_1$-$C_{20}$heteroaryl ring;

$R_8$ and $R_9$ and $R'_8$ and $R'_9$ independently of each other are hydrogen, $C_1$-$C_{12}$alkyl which optionally is substituted by one or more halogen, phenyl, CN, OH, SH, $C_1$-$C_4$alkoxy, $(CO)OH$ or $(CO)O(C_1$-$C_4$alkyl); or $R_8$ and $R_9$ and $R'_8$ and $R'_9$ are phenyl which optionally is substituted by one or more $C_1$-$C_6$alkyl, halogen, CN, $OR_3$, $SR_4$ or $NR_5R_6$; or $R_8$ and $R_9$ and $R'_8$ and $R'_9$ are halogen, CN, $OR_3$, $SR_4$, $SOR_4$, $SO_2R_4$ or $NR_5R_6$, wherein the substituents $OR_3$, $SR_4$ or $NR_5R_6$ optionally form 5- or 6-membered rings via the radicals $R_3$, $R_4$, $R_5$ and/or $R_6$ with one of the carbon atoms of the phenyl or with the substituent $R_7$ or one of the carbon atoms of the naphthylene or phenylene group of $M_3$; or $R_8$ and $R_9$ and $R'_8$ and $R'_9$ together are

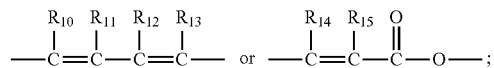

$R_{10}$, $R_{11}$, $R_{12}$ and $R_{13}$ independently of one another are hydrogen, $C_1$-$C_{12}$alkyl which optionally is substituted by one or more halogen, phenyl, CN, OH, SH, $C_1$-$C_4$alkoxy, $(CO)OH$ or $(CO)O(C_1$-$C_4$alkyl); or $R_{10}$, $R_{11}$, $R_{12}$ and $R_{13}$ are phenyl which optionally is substituted by one or more $C_1$-$C_6$alkyl, halogen, CN, $OR_3$, $SR_4$ or $NR_5R_6$; or $R_{10}$, $R_{11}$, $R_{12}$ and $R_{13}$ are halogen, CN, $OR_3$, $SR_4$ or $NR_5R_6$;

$R_{14}$ and $R_{15}$ independently of each other are hydrogen, $C_1$-$C_{12}$alkyl which optionally is substituted by one or more halogen, phenyl, CN, OH, SH, $C_1$-$C_4$alkoxy, $(CO)OH$ or $(CO)O(C_1$-$C_4$alkyl); or $R_{14}$ and $R_{15}$ are phenyl which optionally is substituted by one or more $C_1$-$C_6$alkyl, halogen, CN, $OR_3$, $SR_4$ or $NR_5R_6$;

$R_{17}$ and $R_{18}$ independently of each other are hydrogen, $C_1$-$C_{20}$alkyl, $C_1$-$C_4$haloalkyl, $C_3$-$C_{10}$cycloalkyl or phenyl; or $R_{17}$ and $R_{18}$ together with N-atom to which they are attached form a 5- or 6-membered saturated or unsaturated ring, which optionally is interrupted by O, S or $NR_{24}$;

or $R_{17}$ and $R_{18}$ independently of one another are $C_2$-$C_5$alkylene or $C_2$-$C_5$alkenylene which is attached to one of the C-atoms of the phenyl or naphthyl ring to which the $NR_{17}R_{18}$ is attached, wherein said $C_2$-$C_5$alkylene or $C_2$-$C_5$alkenylene optionally is interrupted by O, CO or $NR_{24}$, and to which $C_2$-$C_5$alkylene or $C_2$-$C_5$alkenylene optionally a benzene ring is condensed;

$R_{19}$ is hydrogen, OH, $C_1$-$C_{20}$alkyl, $C_1$-$C_4$haloalkyl, $C_2$-$C_{20}$alkyl which is interrupted by O, CO or $NR_{24}$, $C_3$-$C_{20}$cycloalkyl which optionally is interrupted by O, S, CO or $NR_{24}$, or is phenyl, naphthyl, phenyl-$C_1$-$C_4$alkyl, $SR_4$, $OR_3$ or $NR_{17}R_{18}$;

$R_{20}$ is $COOR_3$, $CONR_5R_6$, $(CO)R_1$;

or $R_{20}$ has one of the meanings as given for $R_5$ and $R_6$;

$R_{21}$ is $COOR_3$, $CONR_5R_6$, $(CO)R_1$;

or $R_{21}$ has one of the meanings as given for $R_3$;

$R_{22}$ is hydrogen, $C_1$-$C_{20}$alkyl; $C_2$-$C_{20}$alkenyl; $C_3$-$C_{20}$cycloalkyl which optionally is interrupted by O, S, CO or $NR_5$, or is $C_3$-$C_{10}$cycloalkenyl; or is $C_1$-$C_{20}$alkyl which is substituted by one or more halogen, $SR_4$, $OR_3$, $COOR_3$, $NR_5R_6$, $C_1$-$C_{20}$heteroaryl, $C_1$-$C_{20}$heteroaryl-(CO)O, $CONR_5R_6$,

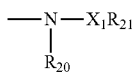

or phenyl; or $R_{22}$ is $C_2$-$C_{20}$alkyl which is interrupted by one or more O and/or optionally is substituted by one or more halogen, $SR_4$, $OR_3$, $COOR_3$, $NR_5R_6$, $C_1$-$C_{20}$heteroaryl, $C_1$-$C_{20}$heteroaryl-(CO)O, $CONR_5R_6$,

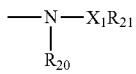

or phenyl;

or $R_{22}$ is phenyl, naphthyl, coumarinyl or $C_1$-$C_{20}$heteroaryl, each of which optionally is substituted by one or more $C_1$-$C_{12}$alkyl, phenyl, halogen, $C_1$-$C_4$haloalkyl, CN, $NO_2$, $SR_4$, $OR_3$, $NR_5R_6$ or by $C_3$-$C_{20}$cycloalkyl which optionally is interrupted by O, CO or $NR_5$;

or $R_{22}$ is $C_2$-$C_{20}$alkanoyl, or benzoyl which is unsubstituted or substituted by one or more $C_1$-$C_6$alkyl, halogen, phenyl, $SR_4$, $OR_3$ or $NR_5R_6$;

or $R_{22}$ is $C_2$-$C_{12}$alkoxycarbonyl which optionally is interrupted by one or more O and/or optionally is substituted by one or more OH;

or $R_{22}$ is phenoxycarbonyl which is unsubstituted or substituted by one or more $C_1$-$C_6$alkyl, $C_1$-$C_4$haloalkyl, halogen, phenyl, $SR_4$, $OR_3$ or $NR_5R_6$;

or $R_{22}$ is $NR_5R_6$;

or $R_{22}$ forms a ring with one of the C-atoms of the phenyl ring to which the group

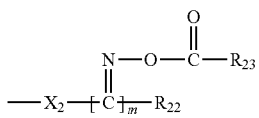

is attached, wherein said formed ring is unsubstituted or substituted;

$R_{23}$ has one of the meanings as given for $R_1$; and $R_{24}$ is hydrogen, $C_1$-$C_{20}$alkyl, $C_1$-$C_4$haloalkyl, $C_2$-$C_{20}$alkyl which is interrupted by O, S or CO, or is phenyl-$C_1$-$C_4$alkyl, $C_3$-$C_{20}$cycloalkyl which optionally is interrupted by O, S or CO, or is phenyl.

2. A photoinititator mixture according to claim 1, wherein the component (i) comprises an alpha-hydroxy ketone, monoacylphosphine oxide, bisacylphosphine oxide, ketosulfone or benzil ketal.

3. Photoinitiator mixture according to claim 1, wherein the compounds of the formula I and (I')

$R_1$ and $R'_1$ are $C_1$-$C_{12}$alkyl;

$R_2$ and $R_2'$ independently of one another are unsubstituted $C_1$-$C_{20}$alkyl or $C_1$-$C_{20}$alkyl substituted by $COOR_3$ or

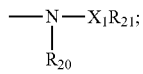

$X_1$ is O;

$R_3$ is $C_1$-$C_{20}$alkyl, $C_1$-$C_8$alkanoyl or phenyl-$C_1$-$C_3$alkyl; or $R_3$ is $C_3$-$C_{20}$cycloalkyl which optionally is interrupted by O;

$R_4$ is $C_1$-$C_{20}$alkyl, $C_1$-$C_8$alkanoyl, phenyl-$C_1$-$C_3$alkyl or $C_1$-$C_{20}$heteroaryl; or $R_4$ is phenyl which is unsubstituted or substituted by $C_1$-$C_{20}$alkyl, halogen or

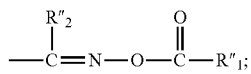

$R_5$ and $R_6$ independently one another are hydrogen, phenyl or $C_1$-$C_{20}$alkyl; or $R_5$ and $R_6$ together with the N-atom to which they are attached form a heteroaromatic ring system, in particular carbazolyl;

$R_7$ is phenyl, naphthyl or $C_1$-$C_{20}$heteroaryl, each of which optionally is substituted by one or more $C_1$-$C_6$alkyl, halogen, CN, $OR_3$, $SR_4$, or $NR_5R_6$;

$R_8$ and $R_9$ are hydrogen;

$R_{20}$ is $(CO)R_1$; and $R_{21}$ is $(CO)R_1$.

4. A photopolymerizable composition comprising
(a) at least one ethylenically unsaturated photopolymerizable compound and
(b) a photoinitiator mixture as defined in claim 1.

5. A photopolymerizable composition comprising
(a) at least one ethylenically unsaturated photopolymerizable aminoacrylate compound or at least one ethylenically unsaturated photopolymerizable acrylate and a H-donor and
(b1) a photoinitiator mixture consisting of at least one compound of the formula I or I' as defined in claim 1 and a benzophenone compound or a thioxanthone compound; and optionally
(d) other additives.

6. A photopolymerizable composition according to claim 4, wherein the component (a) is a resin obtained by the reaction of a saturated or unsaturated polybasic acid anhydride with a product of the reaction of an epoxy resin and an unsaturated monocarboxylic acid.

7. A photopolymerizable composition according to claim 4, additionally to the photoinitiator (b) comprising at least one further photoinitiator (c), and/or other additives (d).

8. A photopolymerizable composition according to claim 5 as further additive (d) comprising a pigment or a mixture of pigments.

9. A photopolymerizable composition according to claim 5 as further additive (d) comprising a dispersant or a mixture of dispersants.

10. A photopolymerizable composition according to claim 4, comprising 0.01 to 25% by weight of the photoinitiator (b), or the photoinitiators (b) and (c), based on the solid composition.

11. A photopolymerizable composition according to claim 4, which is a printing ink.

12. A process for the photopolymerization of compounds containing ethylenically unsaturated double bonds, which comprises irradiating a composition according to claim 4 with electromagnetic radiation in the range from 150 to 600 nm, or with electron beam or with X-rays.

13. A process according to claim 12 for producing pigmented and nonpigmented paints and varnishes, powder coatings, printing inks, printing plates, adhesives, pressure sensitive adhesives, dental compositions, gel coats, photoresists for electronics, electroplating resists, etch resists, both liquid and dry films, solder resists, resists to manufacture color filters for a variety of display applications, resists to generate structures in the manufacturing processes of plasma-display panels, electroluminescence displays and LCD, spacers for LCD, for holographic data storage (HDS), as composition for encapsulating electrical and electronic components, for producing magnetic recording materials, micromechanical parts, waveguides, optical switches, plating masks, etch masks, colour proofing systems, glass fibre cable coatings, screen printing stencils, for producing three-dimensional objects by means of stereolithography, as image recording material, for holographic recordings, microelectronic circuits, decolorizing materials, decolorizing materials for image recording materials, for image recording materials using microcapsules, as a photoresist material for a UV and visible laser direct imaging system, as a photoresist material used for forming dielectric layers in a sequential build-up layer of a printed circuit board.

14. A method of using a composition according to claim 4 for producing pigmented and nonpigmented paints and varnishes, powder coatings, printing inks, printing plates, adhesives, pressure sensitive adhesives, dental compositions, gel coats, photoresists for electronics, electroplating resists, etch resists, both liquid and dry films, solder resists, resists to manufacture color filters for a variety of display applications, resists to generate structures in the manufacturing processes of plasma-display panels, electroluminescence displays and LCD, spacers for LCD, for holographic data storage (HDS), as composition for encapsulating electrical and electronic components, for producing magnetic recording materials, micromechanical parts, waveguides, optical switches, plating masks, etch masks, colour proofing systems, glass fibre cable coatings, screen printing stencils, for producing three-dimensional objects by means of stereolithography, as image recording material, for holographic recordings, microelectronic circuits, decolorizing materials, decolorizing materials for image recording materials, for image recording materials using microcapsules, as a photoresist material for a UV and visible laser direct imaging system, as a photoresist material used for forming dielectric layers in a sequential build-up layer of a printed circuit board.

15. A coated substrate which is coated on at least one surface with a composition according to claim 4.

16. Cured coating obtained by applying a composition according to claim 4 to a substrate and irradiating said coated substrate with electromagnetic radiation in the range from 150 to 600 nm, or with electron beam or with X-rays.

\* \* \* \* \*